United States Patent
Brack et al.

(10) Patent No.: US 9,593,314 B2
(45) Date of Patent: Mar. 14, 2017

(54) BINDING MOLECULES WITH ANTITUMORAL ACTIVITY

(71) Applicant: Covagen AG, Zurich-Schlieren (CH)

(72) Inventors: Simon Brack, Winterthur (CH); Frédéric Mourlane, Olten (CH); Isabella Toller, Zurich (CH); Richard Woods, Zurich (CH); Julian Bertschinger, Hombrechtikon (CH); Dragan Grabulovski, Zurich (CH); Babette Schade, Zurich (CH); Kristina Klupsch, Zurich (CH); Helen Hachemi, Basel (CH)

(73) Assignee: Covagen AG, Schlieren (CH)

( * ) Notice: Subject to any disclaimer, the term of this patent is extended or adjusted under 35 U.S.C. 154(b) by 0 days.

(21) Appl. No.: 14/385,729

(22) PCT Filed: Mar. 8, 2013

(86) PCT No.: PCT/EP2013/054768
§ 371 (c)(1),
(2) Date: Sep. 16, 2014

(87) PCT Pub. No.: WO2013/135588
PCT Pub. Date: Sep. 19, 2013

(65) Prior Publication Data
US 2015/0047065 A1    Feb. 12, 2015

(30) Foreign Application Priority Data
Mar. 16, 2012  (EP) .................... 12159938

(51) Int. Cl.
| | |
|---|---|
| C07K 19/00 | (2006.01) |
| C07K 16/40 | (2006.01) |
| C07K 16/30 | (2006.01) |
| C12N 9/12 | (2006.01) |
| A61K 39/395 | (2006.01) |
| C07K 16/32 | (2006.01) |
| A01K 67/027 | (2006.01) |
| A61K 39/00 | (2006.01) |

(52) U.S. Cl.
CPC ............ *C12N 9/12* (2013.01); *A01K 67/0278* (2013.01); *A61K 39/39591* (2013.01); *C07K 16/30* (2013.01); *C07K 16/32* (2013.01); *A01K 2227/105* (2013.01); *A01K 2267/01* (2013.01); *A61K 2039/505* (2013.01); *C07K 2317/31* (2013.01); *C07K 2317/73* (2013.01); *C07K 2317/77* (2013.01); *C07K 2317/90* (2013.01); *C07K 2318/20* (2013.01); *C07K 2319/00* (2013.01); *C07K 2319/30* (2013.01); *C12Y 207/10002* (2013.01)

(58) Field of Classification Search
None
See application file for complete search history.

(56) References Cited

U.S. PATENT DOCUMENTS

| | | | |
|---|---|---|---|
| 2006/0013819 A1* | 1/2006 | Kelsey | A61K 31/4745 424/155.1 |
| 2006/0099205 A1 | 5/2006 | Adams et al. | |
| 2009/1155275 | 6/2009 | Wu et al. | |
| 2012/0100166 A1* | 4/2012 | Roschke | C07K 16/241 424/185.1 |
| 2015/0105285 A1 | 4/2015 | Grabulovski | |

FOREIGN PATENT DOCUMENTS

| | | |
|---|---|---|
| CN | 1230198 | 9/1999 |
| RU | 2404991 | 10/2008 |
| WO | WO 97/30074 | 8/1997 |
| WO | WO 98/02463 | 1/1998 |
| WO | WO 2006/007398 | 1/2006 |
| WO | WO 2006/028956 | 3/2006 |

(Continued)

OTHER PUBLICATIONS

Robert et al, Tumor Targeting With Newly Designed Biparatopic Antibodies Directed Against Two Different Epitopes of the Carcinoembryonic Antigen (CEA), Int. J. Cancer: 81, 285-291 (1999).*

Grabulovski et al, A Novel, Non-immunogenic Fyn SH3-derived Binding Protein with Tumor Vascular Targeting Properties, Biological Chemistry vol. 282, No. 5, pp. 3196-3204, Feb. 2, 2007.*

Volkel et al, Optimized linker sequences for the expression fo monomeric and dimeric bispecific single-chain diabodies, 2001, vol. 14(10), pp. 815-823.*

J. Bertschinger, et al. *Protein Engineering, Design & Selection*; vol. 20, No. 2, pp. 57-68; 2007.

(Continued)

*Primary Examiner* — Maria Marvich
(74) *Attorney, Agent, or Firm* — Hunton & Williams LLP

(57) ABSTRACT

The present invention relates to a binding molecule that specifically binds to two different epitopes of an antigen expressed on tumor cells, wherein the binding molecule comprises: (a) a first binding (poly)peptide that specifically binds to a first epitope of said antigen expressed on tumor cells, wherein said first binding (poly)peptide is a Fyn SH3-derived polypeptide; and (b) a second binding (poly) peptide that specifically binds to a second epitope of said antigen expressed on tumor cells. The present invention further relates to a nucleic acid molecule encoding the binding molecule of the invention, a vector comprising said nucleic acid molecule as well as a host cell or a non-human host transformed with said vector. The invention further relates to a method of producing a binding molecule of the invention as well as to pharmaceutical and diagnostic composition. Moreover, the present invention also relates to the binding molecule, the nucleic acid molecule, the vector or the host cell of the invention for use in the treatment of tumors.

10 Claims, 13 Drawing Sheets

(56) References Cited

FOREIGN PATENT DOCUMENTS

Figure 1:
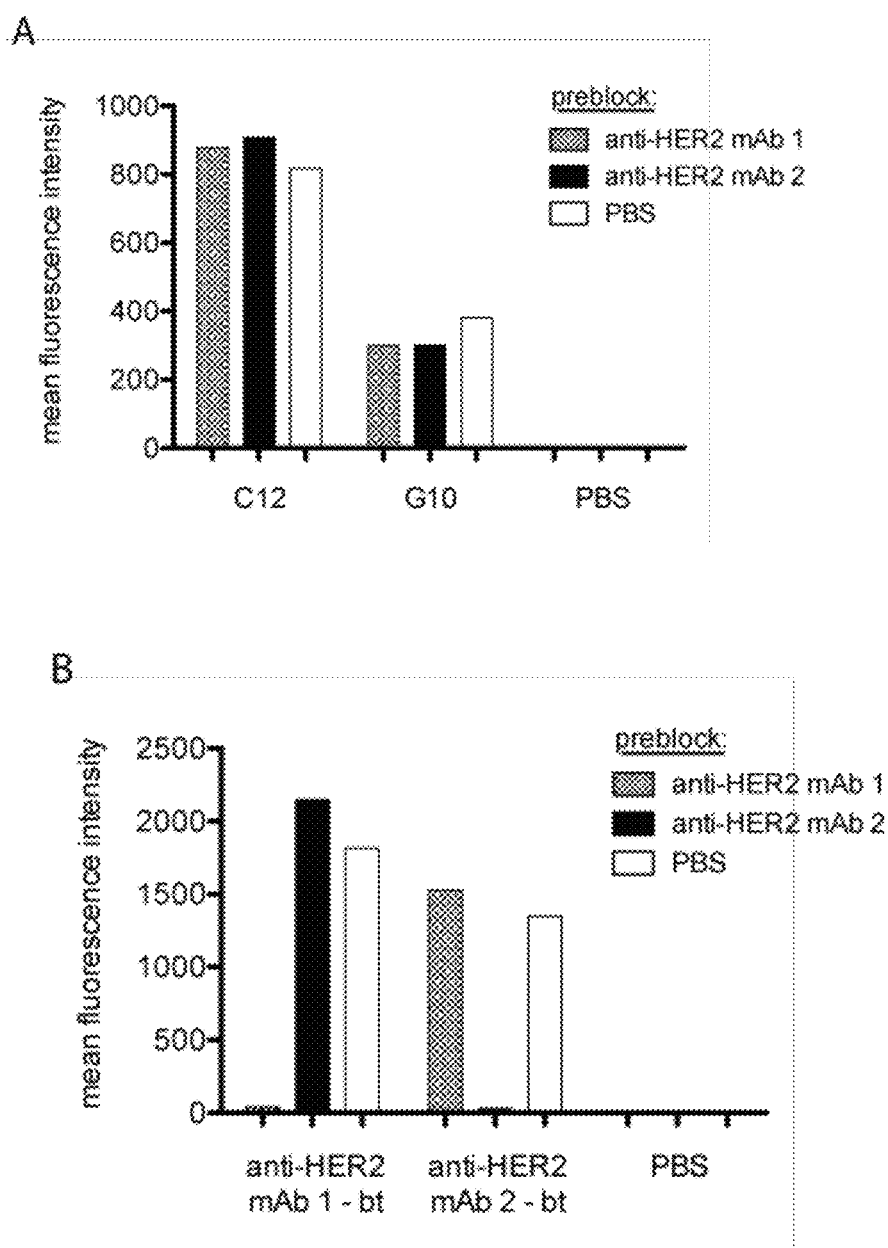

| WO | WO 2008/022759 | 2/2008 |
| WO | WO 2009/052249 | 4/2009 |
| WO | WO 2011/020033 | 2/2011 |
| WO | WO 2011/023685 | 3/2011 |
| WO | WO 2011/069104 | 6/2011 |
| WO | WO 2011/073208 | 6/2011 |
| WO | WO 2011/147986 | 12/2011 |

OTHER PUBLICATIONS

E. Dhimolea et al. "World Bispecific Antibody Summit"; Sep. 27-28, 2011, *Mabs, Landes Bioscience*, vol. 4, No. 1.

D. Grabulovski, et al., "A Novel, Non-immunogenic Fyn SH-3derived Binding Protein with Tumor Vascular Targeting Properties" *Journal of Biological Chemistry* Feb. 2, 2007; pp. 3196-3204; vol. 282, No. 5.

R. Perera, et al., "Treatment of Human Tumor Xenografts with Monoclonal antibody 806 in Combination with a prototypical Epidermal Growth Factor Receptor—Specific Antibody Generates Enhanced Antitumor Activity"; *Clin Cancer Res*; 2005, pp. 6390-6399; vol. 11, No. (17).

\* cited by examiner

A

B

BINDING MOLECULES WITH ANTITUMORAL ACTIVITY

CROSS-REFERENCE TO RELATED APPLICATIONS

This patent application is the U.S. National Stage filing of International Patent Application No. PCT/EP2013/054768, filed Mar. 8, 2013, which claims priority to EP Patent Application No. 12159938.5, filed Mar. 16, 2012, the disclosure of each of which are hereby incorporated by reference.

The present invention relates to a binding molecule that specifically binds to two different epitopes of an antigen expressed on tumor cells, wherein the binding molecule comprises: (a) a first binding (poly)peptide that specifically binds to a first epitope of said antigen expressed on tumor cells, wherein said first binding (poly)peptide is a Fyn SH3-derived polypeptide; and (b) a second binding (poly) peptide that specifically binds to a second epitope of said antigen expressed on tumor cells. The present invention further relates to a nucleic acid molecule encoding the binding molecule of the invention, a vector comprising said nucleic acid molecule as well as a host cell or a non-human host transformed with said vector. The invention also relates to a method of producing a binding molecule of the invention as well as to pharmaceutical and diagnostic composition. Moreover, the present invention also relates to the binding molecule, the nucleic acid molecule, the vector or the host cell of the invention for use in the treatment of tumors.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Non-immunoglobulin-derived binding reagents (collectively designated "scaffolds"; see, for example, Skerra (2000) J. Mol. Recognit. 13, 167-187) have been suggested for use as diagnostic and therapeutic agents. More than 50 different protein scaffolds have been proposed over the past 10 to 15 years, the most advanced approaches in this field being (as summarized in Gebauer and Skerra (2009) Curr Opinion in Chemical Biology 13:245-255): affibodies (based on the Z-domain of staphylococcal protein A), Kunitz type domains, adnectins (based on the 10th domain of human fibronectin), anticalins (derived from lipocalins), DARPins (derived from ankyrin repeat proteins), avimers (based on multimerized LDLR-A), and Fynomers, which are derived from the human Fyn SH3 domain.

In general, SH3 domains are present in a large variety of proteins participating in cellular signal transduction (Musacchio et al. (1994) Prog. Biophys. Mol. Biol. 61; 283-297). These domains do not occupy a fixed position within proteins and can be expressed and purified independently. More than 1000 occurrences of the domain are presently known including about 300 human SH3 domains (Musacchio (2003) Advances in Protein Chemistry. 61; 211-268). Although there is great sequence diversity among SH3 domains, they all share a conserved fold: a compact beta barrel formed by two anti-parallel beta-sheets (Musacchio (2003) Advances in Protein Chemistry. 61; 211-268). Typically, SH3 domains bind to proline-rich peptides containing a PXXP core-binding motif (Ren et al. (1993) Science 259; 1157-1161), but examples of unconventional SH3 binding sites have also been described (Karkkainen et al. (2006) EMBO Rep. 7; 186-191). Most of the SH3 domains sequenced so far have an overall length of approximately 60 to 65 amino acids, but some of them may feature as many as 85 amino acids due to inserts into the loops connecting the main conservative elements of the secondary structure (Koyama et al. (1993) Cell 72(6); 945-952). An alignment of different SH3 domains revealed conserved amino acid residues responsible for the proper structure formation as well as for the canonical proline-rich motif recognition (Larson et al. (2000) Protein Science 9; 2170-2180).

The treatment of tumors with conventional chemotherapeutic agents relies on the expectation that the drugs will preferentially kill rapidly dividing tumor cells rather than normal cells. However, the lack of selectivity towards tumor cells leads to toxicities in normal tissues with enhanced proliferation rates, such as the bone marrow, gastrointestinal tract and hair follicles. Chemotherapeutic agents exhibit poor accumulation in the tumor mass owing to poor blood perfusion, irregular vasculature and high interstitial pressure in the tumor environment (Bosslet et al (1998) Cancer Res 58:1195-1201). Moreover, multidrug resistance proteins may decrease drug uptake (Ramachandran et al (1999) Mol Diagn 4:81-94). As a consequence, the development of therapeutic agents which target preferentially tumor cells represents a main focus of modern anti-cancer research. In this context, the targeted delivery of therapeutic agents to the tumor site by binding to tumor associated antigens is an emerging field of modern anti-cancer research, which promises to concentrate bioactive molecules onto neoplastic lesions while sparing normal tissues (Pfaffen et al (2010) Exp Cell Res 316(5) 836-847). For example, upregulation of the HER2 protein is observed in breast and ovarian cancers and correlates with a poor prognosis (Slamon et al. (1987) Science, 235:177-182; Slamon et al. (1989) Science 244: 707-712). Overexpression of HER2 (frequently but not uniformly due to gene amplification) has also been observed in a range of other tumor types including carcinomas of the bladder, salivary gland, endometrium, pancreas, thyroid, kidney, lung, upper gastrointestinal tract and colon (Scholl et al. (2001) Ann Oncol, 12 Suppl 1:S81-87; Ross J S (2011) Biomark Med 3:307-318; Fukushige et al. (1986) Mol Cell Biol 3:955-958; Cohen et al. (1989) Oncogene 1:81-88; Weiner et al (1990) Cancer Res 50:421-425; Park et al (1989) Cancer Res 23:6605-6609; Zhau et al (1990) Mol. Carcinog. 5:254-257; Aasland et al. (1988) Br J Cancer 4:358-363; Seliger et al (2000) Int J Cancer 87(3):349-359). In addition, HER2 has been found to be overexpressed in prostate cancer, although at lower levels compared to breast cancer tissues (Minner et al. (2010) Clin Cancer Res 16(5): 1553-1560).

In the past, several HER2 binding proteins have been described, such as affibodies and DARPins (Wikman et al (2004) Protein Eng Des Sel 17(5): 455-462; Zahnd et al (2007) 369(4):1015-1028). Moreover, Hudziak et al. describe the generation of a panel of murine anti-HER2 antibodies (including the antibodies 4D5 and 2C4) which were characterized using a human breast tumor cell line (Hudziak et al. (1989) Mol Cell Biol 9(3):1165-1172; see also U.S. Pat. No. 5,677,171). Relative cell proliferation of the cells following exposure to the antibodies was determined. The authors demonstrated that the antibody 4D5 most effectively inhibited cellular proliferation. A recombinant humanized version of the murine anti-HER2 antibody 4D5 (huMAb4D5-8, trastuzumab, Herceptin®, see also U.S.

Pat. No. 5,821,337) was approved by the US Food and Drug Administration in 1998 for the management of HER2-positive metastatic breast cancer (MBC) in combination with chemotherapy. Currently, trastuzumab is recommended as first-line treatment for patients with metastatic HER2-positive tumors, either as a single agent (limited group of patients) or in combination with endocrine therapy or chemotherapy, as well as in the adjuvant setting (Awada et al. (2012) Cancer Treat Rev, 106(1):6-13). However, primary (intrinsic) or secondary (acquired while under treatment) resistance is frequently encountered during treatment with trastuzumab (Tsang et al. (2012) Br J Cancer 106:6-13). For example, it has been observed that the rate of primary resistance to single-agent trastuzumab for HER2-overexpressing metastatic breast cancer is 66-89%. In addition, the majority of patients who achieve an initial response to trastuzumab-based regimens develop resistance within 1 year (Nahta et al (2006) Nat Clin Pract Oncol 3(5):269-280). Several strategies to overcome resistance to trastuzumab therapy have been described in the literature (see review Tsang et al. (2012) Br J Cancer 106:6-13; Awada et al. (2012) Cancer Treat Rev 106(1):6-13).

One attractive avenue to overcome resistance is represented by using combinations of HER2 binding agents. In this context, several groups showed that the combination of two anti-HER2 antibodies inhibited the growth of human tumor cell lines in vitro and/or in vivo better than the treatment with either single antibody alone (Yamashita-Kashima et al (2011) Clin Cancer Res 17(15):5060-5070; Scheuer et al. (2009) Cancer Res 69(24):9330-9336; Lee-Hoeflich et al (2008) Cancer Res 68(14):5878-5887; Kasprzyk et al (1992) Cancer Res 52:2771-2776; Ben-Kasus et al. (2009) Proc Natl Acad Sci USA 106(9):3294-3299). Notably, increased efficacy was observed in preclinical studies where trastuzumab was combined with pertuzumab (pertuzumab is the humanized form of the mouse antibody 2C4 described in Hudziak et al. (Hudziak et al. (1989) Mol Cell Biol 9(3):1165-1172; U.S. Pat. No. 5,677,171); Adams C. W. et al. (2006) Cancer Immunol Immunother, 55:717-727; WO2001/00245)), and Phase 2 clinical trials showed that the co-administration of trastuzumab and pertuzumab produced anti-tumor responses in patients who had previously experienced disease progression while receiving trastuzumab-based therapy (Baselga et al. (2010) J Clin Oncol 28:1138-1144). Pertuzumab binds to domain II of the extracellular part of HER2, whereas trastuzumab binds to a site in domain IV of HER2, which is proximal to the membrane. Due to its binding specificity, pertuzumab was shown to prevent HER2 to form active heterodimers with other HER receptors (such as HER1, HER3 and HER4) (Agus et al (2002) Cancer Cell 2:127-137; Fendly et al (1990) Cancer Res 50(5):1550-1558).

Recently, it has been shown in a Phase III clinical study that the combination of pertuzumab plus trastuzumab plus docetaxel, as compared with placebo plus trastuzumab plus docetaxel, significantly prolonged progression-free survival when used as first-line treatment for HER2-positive metastatic breast cancer patients (Baselga et al (2012) N Engl J Med 366(2):109-119). However, the median independently assessed progression-free survival was prolonged by only 6.1 months (from 12.4 months in the control group to 18.5 months in the pertuzumab group). Moreover, the combination of two or more biological compounds necessitates the dosing of two molecules which usually renders regulatory and clinical procedures more difficult. Furthermore, differences in pharmacokinetics and in tissue concentrations could reduce efficacy of the two antibodies.

Based on the improved therapeutic efficacy of antibody combinations targeting different epitopes on HER2 or EGFR (HER1) (Perera et al. (2005) Clin. Cancer Res. 11:6390-6399), efforts have been undertaken to engineer multispecific EGFR and HER2 targeting proteins, which bind to different epitopes of either EGFR (WO2011/020033) or HER2 (oral presentation of Woisetschläger M., Bispecific Antibody Summit 2011, Sep. 27, 2011, Boston, USA; slides number 5 & 15).

In WO2011/020033, fibronectin domain-based EGFR binding proteins were isolated and fused to the C- or N-terminus of either the heavy and/or light chain of the anti-EGFR monoclonal antibody 225 (also known as cetuximab (Erbitux®)). The EGFR binding fibronectin domains were shown to recognize a different epitope than the antibody 225. Some of the resulting fibronectin-antibody fusions were found to induce EGFR clustering and downregulation more effectively than the antibody 225 on its own.

In the presentation of Woisetschläger M. (oral presentation of Woisetschläger M., Bispecific Antibody Summit 2011, Sep. 27, 2011, Boston, USA; slides number 5 & 15), the bispecific trastuzumab-based HER2-targeting antibody trastuzumab-Her2-1 binding to two different epitopes on HER2 was described. However, no enhanced activity of the bispecific trastuzumab-based antibody as compared to unmodified trastuzumab was observed.

Thus, despite the fact that a lot of effort has been invested into improving antitumor-therapies, there is still a need to identify novel therapeutic compounds for an improved treatment of cancer that overcome the above described disadvantages.

This need is addressed by the provision of the embodiments characterized in the claims.

Accordingly, the present invention relates to a binding molecule that specifically binds to two different epitopes of an antigen expressed on tumor cells, wherein the binding molecule comprises: (a) a first binding (poly)peptide that specifically binds to a first epitope of said antigen expressed on tumor cells, wherein said first binding (poly)peptide is a Fyn SH3-derived polypeptide; and (b) a second binding (poly)peptide that specifically binds to a second epitope of said antigen expressed on tumor cells.

The term "binding molecule that specifically binds to two different epitopes of an antigen" relates to a binding molecule having two different binding specificities for one antigen expressed on tumor cells. In other words, the binding molecule of the present invention is capable of specifically binding to two distinct binding sites (i.e. epitopes) within said one antigen. Moreover, the bispecific binding molecule of the present invention is capable of binding to said two different epitopes at the same time.

In accordance with the present invention, a molecule is considered to bind specifically (also referred to herein as interacting specifically) when the respective molecule does not or essentially does not cross-react with an epitope of similar structure. Cross-reactivity of a panel of molecules under investigation may be tested, for example, by assessing binding of said panel of molecules under conventional conditions to the epitope of interest as well as to a number of more or less (structurally and/or functionally) closely related epitopes. Only those molecules that bind to the epitope of interest in its relevant context (e.g. a specific motif in the structure of a protein) but do not or do not essentially bind to any of the other epitope are considered specific for the epitope of interest. Corresponding methods are described e.g. in Harlow and Lane, Antibodies: A Laboratory Manual, Cold Spring Harbor Laboratory Press, 1988 or Harlow and Lane, Using Antibodies: A Laboratory Manual, Cold Spring Harbor Laboratory Press, 1999). The term "a molecule that essentially does not cross-react with an epitope of similar structure", as used herein, refers to a molecule that binds to the target antigen with at least 5-times higher affinity than to an epitope of similar structure, more preferably at least 10-times higher affinity, such as e.g. at least 50-times higher affinity, more preferably at least 100-times higher affinity, such as e.g. at least 500-times higher affinity. Even more preferably, it binds with at least 1.000-times higher affinity to the target antigen than to an epitope of similar structure, such as e.g. at least 10.000-times higher affinity and most preferably at least 100.000-times higher affinity.

The term "antigen expressed on tumor cells" refers to an antigen that is either not expressed on non-tumor cells or is expressed on tumor cells in a higher amount than on non-tumor cells. Preferably, the antigen is expressed on tumor cells in an at least two times higher amount as on non-tumor cells, more preferably an least five times higher amount, such as e.g. an at least 10-times higher amount, even more preferably an at least 100-time higher amount, such as e.g. an at least 1000-times higher amount and most preferably an at least 10.000-times higher amount. Suitable target antigens include any such antigen that is expressed more strongly on tumor cells, preferably the antigen is one of the antigens defined herein below.

The term "(poly)peptide", as used in accordance with the present invention, describes linear molecular chains of amino acids, including single chain proteins or their fragments. The term refers to a group of molecules which comprises the group of peptides, consisting of up to 30 amino acids, as well as the group of polypeptides (also referred to herein as proteins), consisting of more than 30 amino acids.

Furthermore, peptidomimetics of such (poly)peptide are also encompassed by the present invention, wherein amino acid(s) and/or peptide bond(s) have been replaced by functional analogues. Such functional analogues include all known amino acids other than the 20 gene-encoded amino acids, such as selenocysteine. The term (poly)peptide also refers to naturally modified (poly)peptides, where the modification is effected e.g. by glycosylation, acetylation, phosphorylation and similar modifications which are well known in the art.

In accordance with the present invention, the binding molecule comprises two binding (poly)peptides as defined in (a) and (b).

The first binding (poly)peptide specifically binds to a first epitope of said antigen expressed on tumor cells and is a Fyn SH3-derived polypeptide. It will be appreciated that one or more copies of said first binding (poly)peptide may be present in the binding molecule of the invention, such as e.g. two, three or four copes of the first binding (poly)peptide.

An epitope may be a conformational or a continuous epitope. In polypeptide antigens, a conformational (or discontinuous) epitope is characterized by the presence of two or more discrete amino acid residues which are separated in the primary sequence, but are located near each other on the surface of the molecule when the polypeptide folds into the native three-dimensional structure to constitute the epitope (Sela, (1969) Science 166, 1365 and Laver, (1990) Cell 61, 553-6). The two or more discrete amino acid residues contributing to the epitope are present in separate sections or even in one or more (poly)peptide chain(s) of the antigen. In contrast, a linear or continuous epitope consist of two or more discrete amino acid residues which are located near each other in a single linear segment of a (poly)peptide chain.

The term "Fyn SH3-derived polypeptide", used interchangeably herein with the term "Fynomer", refers to a non-immunoglobulin-derived binding (poly)peptide (e.g. a so-called scaffold as described above) derived from the human Fyn SH3 domain. Fyn SH3-derived polypeptides are well known in the art and have been described e.g. in Grabulovski et al. (2007) JBC, 282, p. 3196-3204 or WO 2008/022759, Bertschinger et al (2007) Protein Eng Des Sel 20(2):57-68, Gebauer and Skerra (2009) Curr Opinion in Chemical Biology 13:245-255).

The SH3 domain of the Fyn kinase (Fyn SH3) comprises 63 residues, namely amino acids 83 to 145 of the sequence reported by Semba et al. (1986) (Proc. Natl. Acad. Sci. USA 83(15): 5459-63) and Kawakami et al. (1986) (Mol Cell Biol. 6(12): 4195-201), with the sequence GVTLFVALYDY EARTEDDLSFHKGEKFQILNSSEGDWWEARSLTTG-ETGYIP SNYVAPVDSIQ, as shown in SEQ ID NO: 164. Fyn is a 59 kDa member of the Src family of tyrosine kinases. As a result of alternative splicing, the Fyn protein exists in two different isoforms differing in their kinase domains: one form is found in thymocytes, splenocytes and some hematolymphoid cell lines, while a second form accumulates principally in brain (Cooke and Perlmutter (1989), New Biol. 1(1): 66-74). The biological functions of Fyn, which is an intracellular protein, are diverse and include signalling via the T cell receptor, regulation of brain function as well as adhesion mediated signalling (Resh (1998) Int. J. Biochem. Cell Biol. 30(11): 1159-62). Just as other SH3 domains, the Fyn SH3 is composed of two antiparallel β-sheets and contains two flexible loops (the RT-Src and n-Src-loops) in order to interact with other proteins. The sequences of the two flexible loops (called RT-Src and n-Src-loops) are underlined and double-underlined, respectively. The amino acid sequence of Fyn SH3 is fully conserved among man, mouse, rat and monkey (gibbon).

As has been shown in the art (WO 2008/022759; Grabulovski et al. (2007) JBC, 282, p. 3196-3204), the Fyn SH3 domain is a particularly attractive scaffold for the generation of binding proteins, i.e. Fynomers. The reason for this is because Fynomers (i) can be expressed in bacteria in soluble form in high amounts, (ii) do not aggregate when stored in solution, (iii) are very stable ($T_m$ 70.5° C.), (iv) lack cysteine residues, and (v) are originally derived from human featuring an amino acid sequence completely conserved from mouse to man, thereby reducing unwanted immunogenic reactions.

The derivation of a specifically binding Fyn SH3-derived polypeptide for a particular target antigen has been described in the art. For example, a library of different Fyn SH3 can be created in which the sequence as shown in SEQ ID NO: 164 above has been altered. Preferably, the alteration is carried out (i) in the sequence representing the RT-loop or optionally in a position up to two amino acids adjacent to said sequence (i.e. the sequence DYEARTEDDL (SEQ ID NO: 173) as shown above in SEQ ID NO: 164), or (ii) in the Scr loop or optionally in a position up to two amino acids adjacent to said sequence (i.e. the sequence LNSSEG (SEQ ID NO: 174) as shown double-underlined above in SEQ ID NO: 164) or (iii) in both sequences simultaneously. Preferably, the alteration is a substitution, deletion or addition as described in the art (see e.g. WO 2008/022759; Grabulovski et al. (2007) JBC, 282, p. 3196-3204). Means and methods for altering an amino acid sequence are well known in the art and are described in the art, e.g. in Grabulovski et al. (2007) JBC, 282, p. 3196-3204.

Subsequently, this Fyn SH3 library can be cloned into a phagemid vector, such as e.g. pHEN1 (Hoogenboom et al. "Multi-subunit proteins on the surface of filamentous phage: methodologies for displaying antibody (Fab) heavy and light chains", Nucleic Acids Res, 19(15):4133-7, 1991) and the library is subsequently displayed on phages and subjected to of panning, preferably repeated rounds of panning such as e.g. at least two, more preferably at least three rounds of panning against the respective antigen. Subsequently, screening for binding (poly)peptides can be performed by established techniques, such as e.g. monoclonal phage-ELISA. Sequencing of the thus identified clones may then be employed to reveal the enriched sequences. The thus identified binding (poly)peptide may further be subjected to further maturation steps, such as e.g. by generating additional libraries based on alterations of the identified sequences and repeated phage display and panning steps. Finally, cross-reactivity and immunogenicity of the resulting Fyn SH3-derived polypeptide may be analysed and a Fyn SH3-derived polypeptide specific for the target antigen can be selected.

These methods of phage display screening and optimization of binding (poly)peptides are generally known in the art.

The second binding (poly)peptide as defined in (b) specifically binds to a second epitope of said antigen expressed on tumor cells. Accordingly, and as described herein above, this means that the same antigen is bound by this second binding (poly)peptide, however a different epitope on said antigen is bound. The term "different" epitope refers to an epitope that does not overlap with the epitope to which the first binding (poly)peptide specifically binds. Accordingly, binding of one of the binding (poly)peptide in accordance with the invention does not block the binding of the second binding (poly)peptide, thus enabling the simultaneous binding of both binding (poly)peptides. The second binding (poly)peptide may be any (poly)peptide capable of specifically binding to a target epitope, such as e.g. an antibody or any of the above described non-immunoglobulin-derived binding reagents or scaffolds, preferably a scaffold selected from the group consisting of affibodies (based on the Z-domain of staphylococcal protein A), Kunitz type domains, adnectins (based on the 10th domain of human fibronectin), anticalins (derived from lipocalins), DARPins (derived from ankyrin repeat proteins), avimers (based on multimerized LDLR-A). All these scaffolds are well known in the art and have been described in the references cited herein above.

The binding (poly)peptides comprised in the binding molecule of the invention may form a single polypeptide chain or may be present in the binding molecule of the invention as several polypeptide chains, which may be covalently or non-covalently bound to each other. Where the binding (poly)peptides form a single polypeptide chain, they may be arranged in any order within said molecule, such as for example (a)-(b) or (b)-(a). More preferably, the binding (poly)peptides of (a) and (b) are arranged in the recited order, e.g. in the order (a) to (b) in the N-terminus to C-terminus direction. Where the binding (poly)peptides do not form a single polypeptide chain, they may still form a linear chain in which they are bound to each other. In that case, they may also be arranged in any order within said linear chain, such as for example (a)-(b) or (b)-(a). More preferably, the binding (poly)peptides of (a) and (b) are arranged in the recited order, e.g. in the order (a) to (b). The binding (poly)peptides may be arranged towards each other in a head-to-tail order, i.e. one binding (poly)peptide is (covalently or non-covalently) bound with its N-terminus to the C-terminus of the other binding (poly)peptide or they may be arranged in a head-to-head or a tail-to-tail order, i.e. one binding (poly)peptide is coupled (covalently or non-covalently) bound either with its N-terminus to the N-terminus of the other binding (poly)peptide or with its C-terminus to the C-terminus of the other binding (poly)peptide. It will be appreciated that the binding (poly)peptides may also form a non-linear arrangement. It will also be appreciated that it is a requirement for all the binding molecules described herein that the binding activity of the two binding (poly)peptides to their respective epitope is retained or essentially retained as defined herein below after formation of the binding molecules, i.e. by the covalent or non-covalent association of the two binding (poly)peptides. Where the binding molecule is formed of several (poly)peptide chains, it is preferred that these chains are covalently bound to each other.

The binding molecule of the invention may be produced by any of the methods of producing (poly)peptides known in the art. For example, as described in more detail herein below, one or more nucleic acid molecules encoding the binding molecule of the present invention may be expressed in a suitable host and the thus produced binding molecule can subsequently be isolated. An alternative method for producing the binding molecule of the invention is in vitro translation of mRNA. Suitable cell-free expression systems for use in accordance with the present invention include rabbit reticulocyte lysate, wheat germ extract, canine pancreatic microsomal membranes, *E. coli* S30 extract, and coupled transcription/translation systems such as the TNT-system (Promega). These systems allow the expression of recombinant (poly)peptides upon the addition of cloning vectors, DNA fragments, or RNA sequences containing coding regions and appropriate promoter elements.

In addition to recombinant production, the binding molecule of the invention may be produced synthetically, e.g. by direct peptide synthesis using solid-phase techniques (cf Stewart et al. (1969) Solid Phase Peptide Synthesis; Freeman Co, San Francisco; Merrifield, J. Am. Chem. Soc. 85 (1963), 2149-2154). Synthetic protein synthesis may be performed using manual techniques or by automation. Automated synthesis may be achieved, for example, using the Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule. As indicated above, chemical synthesis, such as the solid phase procedure described by Houghton Proc. Natl. Acad. Sci. USA (82) (1985), 5131-5135, can be used. Furthermore, the binding molecule of the invention may be produced semi-synthetically, for example by a combination of recombinant and synthetic production.

In accordance with the present invention, it was surprisingly found that a binding molecule comprising a Fyn SH3-derived polypeptide and a second binding (poly)peptide having binding specificity to the same antigen but a different epitope of said antigen resulted in a superior antiproliferative activity on tumor cells. This activity was higher than the activity of a monospecific Fyn SH3-derived polypeptide (in a bivalent format as Fc fusion) or the second binding (poly)peptide alone and, most surprisingly, was also higher than the antiproliferative effect of both compounds given in combination. Accordingly, the generation of the binding molecule of the present invention results in an improved effect as compared to the two separate binding (poly)peptides.

Accordingly, the present invention provides a binding molecule, wherein the binding of said binding molecule to tumor cells expressing the respective target antigen on their surface results in an improved inhibition of tumor activity that is higher than the inhibition of tumor activity obtained by the combined binding of two mono-specific binding proteins, wherein the first mono-specific binding protein comprises or consists of the Fyn SH3-derived polypeptide of (a) and the second mono-specific binding protein comprises or consists of the binding (poly)peptide of (b). Preferably, the improved inhibition of tumor activity is a synergistic, i.e. more than additive effect as compared to the inhibition of tumor activity obtained by the combined binding of two mono-specific binding proteins.

In a preferred embodiment of the binding molecule of the invention, the antigen expressed on tumor cells is selected from the group consisting of HER2, other EGFR family members including HER1, HER3 and HER4, other receptor tyrosine kinase families including the ALK, AXL, DDR, EPH, FGFR, EPH, FGFR, INSR, MET, MUSK, PDGFR, PTK7, RET, ROR, ROS, RYK, TIE, TRK, VEGFR, AATYK families, EpCAM, CD20, CD33, CD52 and CD30.

HER2 is defined in accordance with the pertinent art and relates to a human epidermal growth factor receptor type 2 (also referred to as HER2/neu or ErbB-2, see above), a 185-kDa receptor first described in 1984 (Schlechter et al (1984) Nature 312:513-516). Human HER2 (SEQ ID NO: 171) is represented by the NCBI reference: NP_004439 (publication date 26 Feb. 2012) and has been described in the art, for example in Robinson et al. (2000) Oncogene 19:5548-5557 as well as the references cited herein above. Other targets of the receptor tyrosine kinase families (EGFR, ALK, AXL, DDR, EPH, FGFR, EPH, FGFR, INSR, MET, MUSK, PDGFR, PTK7, RET, ROR, ROS, RYK, TIE, TRK, VEGFR, AATYK) are well known in the art and have been described including NCBI references in Robinson et al. (2000) Oncogene 19:5548-5557.

EpCAM is defined in accordance with the pertinent art and relates to the Epithelial cell adhesion molecule, which is a pan-epithelial differentiation antigen that is expressed on almost all carcinomas. Human EpCAM is represented by the UniProtKB/Swiss-Prot accession number: P16422.2 (publication date 22 Feb. 2012) and has been described in the art, for example in Strnad et al. (1989) Cancer Res. 49(2):314-317.

CD20 is defined in accordance with the pertinent art and relates to the B-lymphocyte antigen CD20. Human CD20 is represented by the NCBI Reference Sequence: NP_690605.1 (publication date 8 Jan. 2012) and has been described in the art, for example in Dawidowicz et al (2011) Clin Exp Rheumatol 29(5):839-842.

CD33 is defined in accordance with the pertinent art and relates to the CD33 antigen. Human CD33 is represented by the NCBI Reference Sequence: NP_001763.3 (publication date 18 Dec. 2011) and has been described in the art, for example in Raponi et al. (2011) Leuk. Lymphoma 52(6): 1098-1107.

CD52 is defined in accordance with the pertinent art and relates to the CD52 antigen (CAMPATH-1 antigen). Human CD33 is represented by the GenBank accession number: EAX07822.1 (publication date 4 Feb. 2010) and has been described in the art, for example in Venter et al (2001) Science 291(5507):1304-1351.

CD30 is defined in accordance with the pertinent art and relates to the CD30 antigen. Human CD30 is represented by the GenBank accession number: AAA51947.1 (publication date 1 Nov. 1994) and has been described in the art, for example in Durkop, H et al. (1992) Cell 68(3):421-427.

In a preferred embodiment of the bi-specific binding molecule of the invention, the antigen is HER2.

In a further preferred embodiment of the binding molecule of the invention, the second binding (poly)peptide is an antibody.

The antibody may be a monoclonal or a polyclonal antibody of any class of antibodies. The term "antibody" also comprises antibody fragments or derivatives thereof which still retain the binding specificity of the respective full length or non-modified antibody. The antibody of the invention also includes embodiments such as synthetic, chimeric, single chain and humanized antibodies.

The term "antibody fragment" relates to fragments, such as a (i) Fab fragment, (ii) F(ab')$_2$ fragment, (iii) Fd fragment (consisting of the VHC and CH1 domains), (iv) a Fv fragment and (v) an isolated complementary determining region (CDR) having sufficient framework to specifically bind, e.g., an antigen binding portion of a variable region. The term "antibody derivative" defines in the context of the invention chemically modified antibodies and antibody fragments. This includes scFv fragments, single domain antibodies etc. Accordingly, antibody derivatives are often (poly)peptides derived from antibody molecules and/or (poly)peptides which are modified by chemical/biochemical or molecular biological methods. The minimal requirement for the specific interaction of an antibody fragment with its specific epitope is the presence of one or more CDRs from the variable heavy chain ($V_H$) and/or the variable light chain ($V_L$) of the parent antibody in a context which allows for the fitting of the antibody fragment and the epitope. Such a context can be provided by the use of a suitable framework of an antibody. As known in the art the term "framework" defines in the context of an antibody or antibody derivative the amino acid sequence which functions as a spacer between the CDRs as well as extends N-terminally and C-terminally thereof and provides for a structure which allows the formation of the antigen binding site by the CDRs. A modification of the framework or CDR sequences, e.g. to improve the binding affinity by molecular biological methods may comprise modification of the (poly)peptides using conventional techniques known in the art, for example, by using amino acid deletion(s), insertion(s), substitution(s), addition(s), and/or recombination(s) and/or any other modification(s) (e.g. posttranslational and chemical modifications, such as glycosylation and phosphorylation) known in the art either alone or in combination. Methods for introducing such modifications in the DNA sequence underlying the amino acid sequence of an immunoglobulin chain are well known to the person skilled in the art; see, e.g., Sambrook et al., Molecular Cloning: A Laboratory Manual, Cold Spring Harbor Laboratory Press, 2nd edition 1989 and 3rd edition 2001; Gerhardt et al., Methods for General and Molecular Bacteriology, ASM Press, 1994; Lefkovits, Immunology Methods Manual: The Comprehensive Sourcebook of Techniques, Academic Press, 1997; or Golemis, Protein-Protein Interactions: A Molecular Cloning Manual, Cold Spring Harbor Laboratory Press, 2002.

An antibody in accordance with the invention is capable of specifically binding/interacting with an epitope. The epitope may be a polypeptide structure as well as compounds which do not comprise amino acids, such as e.g.

polysaccharides. The term "specifically binding/interacting with" is as defined herein above.

Preferably, the antibody is a monoclonal antibody. Even more preferably, the (monoclonal) antibody is of the IgG, IgA, IgE, IgD or IgM class (as well as subtypes thereof (e.g., IgG1, IgG2, IgG3 and IgG4)).

It will be appreciated that the Fyn SH3-derived polypeptide representing the first binding (poly)peptide may be coupled to the antibody in any possible position, as long as the binding capabilities of the two binding (poly)peptides is retained or essentially retained, as defined herein below. For example, the Fyn SH3-derived polypeptide representing the first binding (poly)peptide may be coupled to the antibody at the N- or C-terminal end of either the heavy chain or light chain where a complete antibody is employed. Preferably, the Fyn SH3-derived polypeptide is coupled to the N-terminal end of the light chain of an antibody.

In another preferred embodiment of the binding molecule of the present invention, the first and second binding (poly)peptide are linked by a linker.

The term "linker" as used in accordance with the present invention relates to a sequel of amino acids (i.e. peptide linkers) as well as to non-peptide linkers, which separate the binding (poly)peptides of the binding molecule of the invention. It will be appreciated that where the binding molecule of the present is a single polypeptide chain, the linker is a peptide linker.

The nature, i.e. the length and/or composition (such as e.g. amino acid sequence) of the linker may modify or enhance the stability and/or solubility of the molecule, it may enhance the flexibility of the resulting binding molecule and/or may improve the binding to the target antigen by reducing sterical hindrance. The length and composition of a linker depends on the composition of the respective binding (poly)peptides of the binding molecule of the invention. The skilled person is well aware of methods to test the suitability of different linkers. For example, the properties of the binding molecule can easily be tested by analysing its binding affinity when using different types of linkers. In addition, the respective measurements for each binding (poly)peptide alone may be carried out and compared to the binding affinity of the binding molecule. The stability of the resulting molecule can be measured by methods known in the art, such as e.g. using an ELISA method to determine the residual binding capacity of the molecule after incubation in human serum at 37° C. for several time periods.

Peptide linkers as envisaged by the present invention are (poly)peptide linkers composed of amino acids. Preferably, the linker is 1 to 100 amino acids in length. More preferably, the linker is 5 to 50 amino acids in length and even more preferably, the linker is 10 to 20 amino acids in length. Most preferably, the linker is 15 amino acid in length. In a preferred embodiment, the linker is a flexible linker using e.g. the amino acids alanine and serine or glycine and serine. Preferably the linker sequences are $(Gly_4Ser)_1$, $(Gly_4Ser)_2$, or $(Gly_4Ser)_3$. Most preferably, the linker is $(Gly_4Ser)_3$.

The term "non-peptide linker", as used in accordance with the present invention, refers to linkage groups having two or more reactive groups but excluding peptide linkers as defined above. For example, the non-peptide linker may be a polymer, such as e.g. polyethylene glycol, having reactive groups at both ends, which individually bind to reactive groups of the binding portions of the molecule of the invention, for example, an amino terminus, a lysine residue, a histidine residue or a cysteine residue. The reactive groups of the polymer include a hydroxyl group, an aldehyde group, a propionic aldehyde group, a butyl aldehyde group, a maleimide group, a ketone group, a vinyl sulfone group, a thiol group, a hydrazide group, a carbonyldimidazole (CD) group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at both ends of the non-peptide polymer may be the same or different. For example, the non-peptide polymer may have a maleimide group at one end and an aldehyde group at another end. Preferably, the polymer is polyethylene glycol.

Most preferably, the linker is a peptide linker.

In another preferred embodiment, the binding molecule of the invention further comprises at least one additional (poly)peptide.

Non-limiting examples of such additional (poly)peptides are e.g. pharmaceutically and/or diagnostically active components, including tags or functional (poly)peptides suitable to improve the performance of the binding molecule of the invention.

Pharmaceutically and/or diagnostically active components may for example be selected from cytokines, toxic compounds, chemokines, enzymes, fluorescent dyes and photosensitizers, pro-coagulant factor, preferably a tissue factor, radionuclides or components that modulate the serum half-life of the binding molecule of the invention.

Non-limiting examples of cytokines include e.g. IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1alpha and IL-1beta.

Examples of toxic compounds include, without being limiting, calicheamicin, maytansinoid, neocarzinostatin, esperamicin, dynemicin, kedarcidin, maduropeptin, doxorubicin, daunorubicin, auristatin, Ricin-A chain, modeccin, truncated Pseudomonas exotoxin A, diphtheria toxin and recombinant gelonin.

Non-limiting examples of chemokines include IL-8, GRO alpha, GRO beta, GRO gamma, ENA-78, LDGF-PBP, GCP-2, PF4, Mig, IP-10, SDF-1alpha/beta, BUNZO/STRC33, I-TAC, BLC/BCA-1, MIP-1alpha, MIP-1 beta, MDC, TECK, TARC, RANTES, HCC-1, HCC-4, DC-CK1, MIP-3 alpha, MIP-3 beta, MCP-1-5, Eotaxin, Eotaxin-2, I-309, MPIF-1, 6Ckine, CTACK, MEC, Lymphotactin and Fractalkine.

Fluorescent dyes include e.g. Alexa Fluor or Cy dyes and photosensitizers include for example phototoxic red fluorescent protein KillerRed or haematoporphyrin.

Non-limiting examples of enzymes include enzymes for pro-drug activation, preferably enzymes selected from the group consisting of carboxy-peptidases, glucuronidases and glucosidases.

Radionuclides may be selected from e.g. the group of gamma-emitting isotopes, preferably $^{99m}Tc$, $^{123}I$, $^{111}In$; from the group of positron emitters, preferably $^{18}F$, $^{64}Cu$, $^{68}Ga$, $^{86}Y$, $^{124}I$; from the group of beta-emitters, preferably $^{131}I$, $^{90}Y$, $^{177}Lu$, $^{67}Cu$; or from the group of alpha-emitters, preferably $^{213}Bi$, $^{211}At$.

Examples of components that modulate serum half-life include, without being limiting, polyethylene glycol (PEG), Fc domains of antibodies, albumin-binding proteins and conformationally disordered polypeptide sequences.

Non-limiting examples of tags include Strep-tags, His-tags, Myc-tags, TAP-tags or Flag-tags. Additional functional (poly)peptides are e.g. secretion peptides such as the kappa secretion leader or peptides providing N-glycosylation sites.

As outlined herein above, some of the additional (poly) peptides may have an additional pharmaceutical or diagnostic activity or may enhance stability of the binding molecule of the invention, thereby enhancing its antitumorigenic activity, while other additional (poly)peptides may instead facilitate the preparation and/or purification of the binding molecule.

Methods to add the above defined additional (poly)peptides to the binding molecule of the invention are well known to the skilled person and are described e.g. in Sambrook, 2001, loc cit. It will be appreciated that the additional (poly)peptides may be non-covalently bound to the binding molecule of the invention or may be covalently bound, for example they may form a fusion protein with binding molecule, e.g. they may form a single polypeptide chain. Such a fusion protein may for example be encoded by a single nucleic acid molecule.

Also encompassed by the present invention are multimers, such as e.g. dimers, trimers, tetramers etc., formed of the binding molecule of the invention, optionally including additional (poly)peptides as defined herein above. Such multimers may be formed by covalent or non-covalent association, preferably by covalent association. Preferably, multimers are formed via linkers as defined herein above, preferably the above defined peptide linkers. More preferably, the linker is $(Gly_4Ser)_1$, $(Gly_4Ser)_2$, or $(Gly_4Ser)_3$. Most preferably, the linker is $(Gly_4Ser)_3$.

In a further preferred embodiment of the binding molecule of the invention, the first binding (poly)peptide comprises or consists of (i) an amino acid sequence selected from the group consisting of SEQ ID NO: 1 to 152 or (ii) an amino acid sequence having at least 65% sequence identity to the amino acid sequence of SEQ ID NO: 1.

In those embodiments where a binding (poly)peptide comprises (rather than consists of) the recited amino acid sequence, additional amino acids extend over the specific sequence either at the N-terminal end or the C-terminal end or both. Preferably, no more than 50 additional amino acids are present at the N-terminal end and no more than 50 additional amino acids are present at the C-terminal end. More preferably no more than 40, such as no more than 30, more preferably no more than 20, such as no more than 10, no more than 9, no more than 8, no more than 7, no more than 6, no more than 5, no more than 4, no more than 3, no more than 2 and even more preferably no more than 1 additional amino acid(s) are/is independently present at either one or both of the N- or C-terminal end. It will be appreciated that it is a prerequisite that the binding capacity of the binding molecule to the two different epitopes of the target antigen is retained or essentially retained as defined herein below in the presence of these additional amino acids. Additional sequences may include for example sequences introduced e.g. for purification. Preferably, the first binding (poly)peptide consists of the amino acid sequence recited in (i) or (ii). More preferably, the first binding (poly)peptide consists of the amino acid sequence of SEQ ID NO:1.

In accordance with the present invention, the term "% sequence identity" describes the number of matches ("hits") of identical amino acids/nucleotides of two or more aligned amino acid or nucleic acid sequences as compared to the number of amino acid residues or nucleotides making up the overall length of the amino acid sequences or nucleic acid (or the overall compared part thereof). In other terms, using an alignment, for two or more sequences or sub-sequences the percentage of amino acid residues or nucleotides that are the same (e.g., 65% or 80% identity) may be determined, when the (sub)sequences are compared and aligned for maximum correspondence over a window of comparison, or over a designated region as measured using a sequence comparison algorithm as known in the art, or when manually aligned and visually inspected. Preferred (poly)peptides in accordance with the invention are those where the described identity exists over a region that is at least about 15 to 25 amino acids in length, more preferably, over a region that is at least about 30 to 50 amino acids in length. More preferred (poly)peptides in accordance with the present invention are those having the described sequence identity over the entire length of the (poly)peptides specifically recited herein. Those having skill in the art will know how to determine percent sequence identity between/among sequences using, for example, algorithms such as those based on the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402), CLUSTALW computer program (Thompson Nucl. Acids Res. 2 (1994), 4673-4680) or FASTA (Pearson and Lipman, Proc. Natl. Acad. Sci., 1988, 85; 2444).

The NCBI BLAST algorithm is preferably employed in accordance with this invention. For amino acid sequences, the BLASTP program uses as default a word length (W) of 3, and an expectation (E) of 10. The BLASTN program for nucleic acid sequences uses as default a word length (W) of 11, an expectation (E) of 10, M=5, N=4, and a comparison of both strands. The BLOSUM62 scoring matrix (Henikoff, Proc. Natl. Acad. Sci., 1989, 89:10915) uses alignments (B) of 50, expectation (E) of 10, M=5, N=4, and a comparison of both strands. Accordingly, all the (poly)peptides having a sequence identity of at least 80% as determined with the NCBI BLAST program fall under the scope of the invention.

In accordance with this embodiment of the present invention, also encompassed are sequences having at least 65% sequence identity, such as at least 70%, at least 80%, at least 85% and at least 90% sequence identity. Even more preferably, the identity is at least 95%, such as at least 98%, at least 99% and most preferably at least 99.5%.

The amino acid sequence having at least 65% sequence identity to the amino acid sequence of SEQ ID NO: 1 preferably has the following formula I:

(Formula I)                                    (SEQ ID NO: 175)
GVTLFVALYDYX$_1$ X$_2$ X$_3$ X$_4$ X$_5$ X$_6$ X$_7$ X$_8$ X$_9$ X$_{10}$LSFHKGEK FQIL X$_{11}$ X$_{12}$ X$_{13}$ X$_{14}$ X$_{15}$ X$_{16}$G X$_{17}$WW X$_{18}$ARSLTTGE

X$_{19}$G X$_{20}$IPS X$_{21}$YVAPVDSIQ wherein $X_1$ to $X_7$ and $X_{11}$ to $X_{13}$ and $X_{17}$ to $X_{21}$ are each independently selected from G, V, T, L, F, A, Y, D, S, H, K, E, Q, I, W, R, M, P, N and C; more preferably from G, V, T, L, F, A, Y, D, S, H, K, E, Q, I, W, R, M, P and N; and wherein $X_8$ to $X_{10}$ and $X_{14}$ to $X_{16}$ are each independently selected from G, V, T, L, F, A, Y, D, S, H, K, E, Q, I, W, R, M, P, N and C; more preferably from G, V, T, L, F, A, Y, D, S, H, K, E, Q, I, W, R, M, P and N;

or wherein one or more of $X_8$ to $X_{10}$ and $X_{14}$ to $X_{16}$ is absent.

More preferably, $X_1$ is selected from: T, E, D, Q, Y, V, W, N, S, F or K $X_2$ is selected from: S, A, R or T $X_3$ is selected from: Y, R, H, T, N, V, W or S $X_4$ is selected from: N, D, M, Y, R, P, E, L, H, T, G or F $X_5$ is selected from: T, S, P, Q, R, K, G, Q, A, D, M, N, L, F, Y or E $X_6$ is selected from: R, M, K, D, F, T, G, H, S, P, N, Q, Y, L, A or P $X_7$ is selected from: D, G, V, L, H, N, R, F, S or A $X_8$ is selected from: G, S, E, D, P, Y or is absent $X_9$ is selected from: Q, D, S, H or is absent $X_{10}$ is selected from: D, V or is absent $X_{11}$ is selected from: R, K, Q, N, S, G, W, M, H, L, F, E, T, P, A, D or V $X_{12}$ is selected from: M, R, E, G, N, D, S, A, Q, F, P, K, Y, T, H, V, L or W $X_{13}$ is selected from: E, W, P, R, K, S, V, N, D, H, G, T, Q, A, Y, L or M $X_{14}$ is selected from: D, R, Q, S, A, N, P, I, H, T, Y, E, L, K, M, V, I, W or is absent $X_{15}$ is selected from: G, S, I, L, A, V, T, E, D, Q, R, P, K, M, H, Y or is absent $X_{16}$ is selected from: K, G, R, A, T, V, S, I, E, Q, P, D, N, H or is absent $X_{17}$ is selected from: V, D, T, I or Y $X_{18}$ is selected from: E, A, R, T or Q $X_{19}$ is selected from: T, I or V $X_{20}$ is selected from: Y, L or F $X_{21}$ is selected from: N or S.

In a preferred embodiment, the residues X in formula I are independently selected from: $X_1$ to $X_{10}$ is TSYNTRD (i.e. wherein $X_8$ to $X_{10}$ are absent) (SEQ ID NO: 176); $X_{11}$ to $X_{16}$ is RMED (i.e. wherein $X_{14}$ to $X_{16}$ are absent) (SEQ ID NO: 177); $X_{17}$ is V; $X_{18}$ is E; $X_{19}$ is T; $X_{20}$ is Y and/or $X_{21}$ is N.

Preferably, the binding (poly)peptide comprising or consisting of an amino acid sequence having at least 65% sequence identity to the amino acid sequence of SEQ ID NO: 1 retains or essentially retains the binding capacity of the binding (poly)peptide consisting of SEQ ID NO:1, i.e. the strength of binding to the respective target epitope is retained or essentially retained.

The Fyn SH3-derived polypeptide C12 (SEQ ID NO: 1) has a dissociation constant for its specific epitope on HER2 of $7 \times 10^{-8}$ M when determined by surface plasmon resonance (SPR). For this, the Fyn SH3-derived polypeptide is captured, for example by a His-tag specific antibody, which has been immobilized on a BIAcore sensor chip. Upon injection of the antigen containing the specific epitope, formation of the complex is monitored and kinetic association ($k_{on}$) and kinetic dissociation constants ($k_{off}$), or dissociation constants ($K_D$), are obtained by curve fitting using the software BIAcore evaluation software. Accordingly, the binding capacity of the binding (poly)peptide comprising or consisting of an amino acid sequence having at least 65% sequence identity to the amino acid sequence of SEQ ID NO: 1 is essentially retained if a dissociation constant, preferably under the same conditions, for HER2-binding of at least $1 \times 10^{-4}$ M is retained, such as e.g. at least $1 \times 10^{-5}$ M, more preferably at least at least $1 \times 10^{-6}$ M and most preferably at least $1 \times 10^{-7}$ M. Also in accordance with the invention are binding (poly)peptides having an increased binding capacity compared to the binding (poly)peptide consisting of SEQ ID NO:1, i.e. more than 100% activity. For example, envisaged herein are binding (poly)peptides having a dissociation constant of at least $1 \times 10^{-8}$ M, such as e.g. at least $1 \times 10^{-9}$ M, more preferably at least at least $1 \times 10^{-10}$ M, such as e.g. at least $1 \times 10^{-11}$ M, even more preferably at least at least $1 \times 10^{-12}$ M and most preferably at least $1 \times 10^{-13}$ M. Methods of assessing the binding capacity are well known in the art and include, without being limiting, surface Plasmon resonance (SPR) techniques or ELISA.

As is shown in the appended examples, binding molecules comprising the Fyn SH3-derived polypeptide C12 (SEQ ID NO: 1) and a second binding specificity specifically bind to the tumor antigen HER2 and produce an improved inhibitory effect with the second binding (poly)peptide. Accordingly, it is preferred that the binding molecule of the invention comprises a Fyn SH3-derived polypeptide comprising or consisting of SEQ ID NO: 1.

As is evident from Example 14 herein below, the Fyn SH3-derived polypeptide C12 (SEQ ID NO: 1) binds to an epitope of HER2 which is located within domain I of HER2 (SEQ ID NO: 172). The involved residues of the HER2 protein were determined using an alanine scanning approach and amino acid positions T166, R188, P197, S202 and R203 of domain I of HER2 were found to be involved in binding between the Fyn SH3-derived polypeptide C12 and HER2.

Consequently in another preferred embodiment of the binding molecule of the invention, the first binding (poly)peptide comprises or consists of an amino acid sequence which binds to an epitope within domain I of HER2 (SEQ ID NO: 172), and preferably an epitope within domain I of HER2 (SEQ ID NO: 172) comprising amino acid positions T166, R188, P197, S202 and R203 thereof.

In another preferred embodiment of the binding molecule of the invention, the second binding (poly)peptide is an antibody, wherein (i) the heavy chain of the antibody comprises or consists of the amino acid sequence of SEQ ID NO: 154 and the light chain of the antibody comprises or consists of the amino acid sequence of SEQ ID NO: 155; (ii) the heavy chain of the antibody comprises or consists of SEQ ID NO: 160 and the light chain of the antibody comprises or consists of the amino acid sequence of SEQ ID NO: 163; (iii) the heavy chain of the antibody comprises or consists of an amino acid sequence having at least 65% sequence identity to the amino acid sequence of SEQ ID NO: 154 and the light chain of the antibody comprises or consists of an amino acid sequence having at least 65% sequence identity to the amino acid sequence of SEQ ID NO: 155; or (iv) the heavy chain of the antibody comprises or consists of an amino acid sequence having at least 65% sequence identity to the amino acid sequence of SEQ ID NO: 160 and the light chain of the antibody comprises or consists of an amino acid sequence having at least 65% sequence identity to the amino acid sequence of SEQ ID NO: 163.

Exemplary nucleic acid molecules encoding the heavy and light chains of SEQ ID NOs: 154, 155, 160 and 163 are shown in SEQ ID NOs: 165, 166, 168 and 169, respectively.

In accordance with this embodiment of the present invention, also encompassed in (iii) and (iv) are sequences having at least 65% sequence identity, such as at least 70%, at least 80%, at least 85% and at least 90% sequence identity to the recited amino acid sequences. Even more preferably, the identity is at least 95%, such as at least 98%, at least 99% and most preferably at least 99.5% to the recited amino acid sequences.

More preferably, the antibody defined in (iii) or (iv) is an antibody wherein the variation in the sequence identity occurs solely in the variable domain of the antibodies, such that the constant region of the variant antibodies is identical to the constant region of the antibody as defined in (i) and (ii), respectively. The variable domains of the anti-HER2 antibody 1 used herein are located in amino acids 1 to 119 of SEQ ID NO:154 and amino acids 1 to 107 of SEQ ID NO:155 while the variable domains of the anti-HER2 antibody 2 used herein are located in amino acids 1 to 120 of SEQ ID NO:160 and amino acids 1 to 107 of SEQ ID NO:163. Even more preferably, the variation in the sequence identity occurs solely in the CDR domains of the antibodies, such that the remaining (non-CDR) regions of the variant antibodies is identical to the remaining (non-CDR) regions of the antibody as defined in (i) and (ii), respectively. The CDR domains of the anti-HER2 antibody 1 used herein are located in amino acids 31 to 35 (CDR1), 50 to 66 (CDR2) and 99 to 108 (CDR3) of SEQ ID NO:154 and amino acids 24 to 34 (CDR1), 50 to 56 (CDR2) and 89 to 97 (CDR3) of SEQ ID NO:155 while the CDR domains of the anti-HER2 antibody 2 used herein are located in amino acids 31 to 35 (CDR1), 50 to 66 (CDR2) and 99 to 109 (CDR3) of SEQ ID NO:160 and amino acids 24 to 34 (CDR1), 50 to 56 (CDR2) and 89 to 97 (CDR3) of SEQ ID NO:163.

All of the definition provided above with regard to the first binding (poly)peptide, for example with regard to the term "comprising" and the preferred amounts of sequence identity and methods of determining these, apply mutatis mutandis also to this second binding (poly)peptide of the binding molecule of the invention.

Furthermore, the second binding (poly)peptide defined in (iii) preferably retains or essentially retains the binding capacity of the binding (poly)peptide defined in (i) and the second binding (poly)peptide defined in (iv) preferably retains or essentially retains the binding capacity of the binding (poly)peptide defined in (ii). As defined herein above, the binding capacity of the binding (poly)peptide of (iii) or (iv) is essentially retained if at least 60% of its binding capacity is retained. Preferably, at least 75% or more preferably at least 80% of its binding capacity is retained. More preferred is that at least 90% such as at least 95%, even more preferred at least 98% such as at least 99% of the binding capacity of the binding (poly)peptide defined in (i) or (ii), respectively, is retained. Most preferred is that the binding capacity is fully, i.e. to 100%, retained. Also in accordance with the invention are binding (poly)peptides having an increased binding capacity compared to the binding (poly)peptides defined in (i) or (ii), respectively, i.e. more than 100% activity. Preferably, the binding capacity refers to the binding capacity of a binding (poly)peptide to HER2. Methods of assessing the binding capacity have been described herein above.

The antibodies as defined in (i) and (ii) of this embodiment have a dissociation constant for their specific epitope on HER2 of between $2\times10^{-9}$ M to $2\times10^{-10}$ M when determined by surface plasmon resonance (SPR). For this, the antibodies are captured by a human IgG-specific antibody which has been immobilized on a BIAcore sensor chip. Upon injection of the antigen containing the specific epitope, formation of the complex is monitored and kinetic association ($k_{on}$) and kinetic dissociation constants ($k_{off}$), or dissociation constants ($K_D$), are obtained by curve fitting using the software BIAcore evaluation software. Accordingly, the binding capacity of an antibody having at least 65% sequence identity to the antibody of (i) or (ii) is essentially retained if a dissociation constant, preferably measured under the same conditions, for HER2-binding of at least $1\times10^{-5}$ M is retained, such as e.g. at least $1\times10^{-6}$ M, more preferably at least at least $1\times10^{-7}$ M, even more preferably at least $1\times10^{-8}$ M and most preferably at least $1\times10^{-9}$ M. Also in accordance with the invention are antibodies having an increased binding capacity compared to the antibodies of (i) or (ii), i.e. more than 100% activity. For example, envisaged herein are antibodies having a dissociation constant of at least $1\times10^{-10}$ M, such as e.g. at least $1\times10^{-11}$ M, more preferably at least at least $1\times10^{-12}$ M and most preferably at least $1\times10^{-13}$ M.

Preferably, the second binding (poly)peptide is an antibody wherein the heavy chain of the antibody consists of the amino acid sequence of SEQ ID NO: 154 and the light chain of the antibody consists of the amino acid sequence of SEQ ID NO: 155.

Preferably, the first binding (poly)peptide consists of the amino acid sequence of SEQ ID NO: 1 and the second binding (poly)peptide is an antibody wherein the heavy chain of the antibody consists of the amino acid sequence of SEQ ID NO: 154 and the light chain of the antibody consists of the amino acid sequence of SEQ ID NO: 155. More preferred, the C-terminal end of SEQ ID NO: 1 is linked to the N-terminal end of the light chain of said antibody, i.e. to SEQ ID NO: 155. In an even more preferred embodiment of the binding molecule of the invention, the first binding (poly)peptide consists of the amino acid sequence of SEQ ID NO: 1 linked via a $(Gly_4Ser)_3$ linker to the second binding (poly)peptide, which is an antibody wherein the heavy chain of the antibody consists of the amino acid sequence of SEQ ID NO: 154 and the light chain of the antibody consists of the amino acid sequence of SEQ ID NO: 155 and wherein the linker connects the C-terminal end of SEQ ID NO: 1 with the N-terminal end of the light chain of the antibody, i.e. SEQ ID NO: 155. The amino acid sequence of this fusion protein of SEQ ID NO:1, the linker $(Gly_4Ser)_3$ and the light chain represented by SEQ ID NO:155 is shown in SEQ ID NO: 159 (an exemplary nucleic acid molecule encoding this amino acid sequence is shown in SEQ ID NO: 167). It will be appreciated that where an antibody comprising e.g. two light and two heavy chains is employed as the second binding (poly)peptide and wherein the first binding (poly)peptide is fused to either the light or heavy chain of said antibody, the resulting binding molecule in accordance with the present invention may comprise said one antibody and two first binding (poly)peptides, fused to each one of the two (either light or heavy) chains of the antibody. Examples of such binding molecules of the invention are described in the appended examples and are shown for example in FIG. 8 below.

As is shown in the appended examples, a binding molecule as defined above (also referred to herein as COVA208) provides superior antitumor activities on HER2-expressing tumors. The antitumor activity observed using the binding molecule of the invention is significantly higher than the inhibition of tumor activity obtained by the combined binding of two mono-specific binding proteins, wherein the first mono-specific binding protein is the bivalent Fyn SH3-derived polypeptide having SEQ ID NO:153 (i.e. the Fc-fusion of C12 (SEQ ID NO: 1)) and the second mono-specific binding protein is the anti-HER2 antibody 1 wherein the heavy chain of the antibody consists of the amino acid sequence of SEQ ID NO: 154 and the light chain of the antibody consists of the amino acid sequence of SEQ ID NO: 155.

The present invention further relates to a nucleic acid molecule encoding the binding molecule of the invention.

In accordance with the present invention the term "nucleic acid molecule", also referred to as "polynucleotide" or "nucleic acid sequence" herein, defines a linear molecular chain consisting of more than 30 nucleotides. "Nucleic acid molecules", in accordance with the present invention, include DNA, such as for example cDNA or genomic DNA, and RNA, for example mRNA. Further included are nucleic acid mimicking molecules known in the art such as for example synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA) and locked nucleic acid (LNA) (see Braasch and Corey, Chem Biol 2001, 8: 1). LNA is an RNA derivative in which the ribose ring is constrained by a methylene linkage between the 2'-oxygen and the 4'-carbon. They may contain additional non-natural or derivative nucleotide bases, as will be readily appreciated by those skilled in the art.

It will be appreciated that the binding molecule of the present invention may be encoded by a single nucleic acid molecule or a plurality of nucleic acid molecules encoding parts of the binding molecule, such as e.g. the individual binding (poly)peptides or different chains of an antibody. Upon expression of these nucleic acid molecules, they form the binding molecule of the invention via non-covalent bonds such as for example hydrogen bonds, ionic bonds, van der Waals forces or hydrophobic interacts or via covalent bonds such as for example disulfide bonds.

For example, where the binding molecule is a Fyn SH3-derived polypeptide bound to an antibody-fragment comprising e.g. of only the scFv fragment or dAb, then the binding molecule may be encoded by a single nucleic acid molecule. Where the binding molecule comprises a Fyn SH3-derived polypeptide bound to a full-length antibody as shown in the appended examples, a first nucleic acid molecule may encode the Fyn SH3-derived polypeptide and the chain of the antibody to which the Fyn SH3-derived polypeptide is bound and a second nucleic acid molecule may encode the remaining chain of the antibody. Alternatively, a single nucleic acid molecule may encode also these separate polypeptide chains, for example when the encoding nucleic acid sequences are included in a vector comprising the respective regulatory elements for each of the encoding sequences. It will be appreciated that where several nucleic acid sequences (or vectors as described below) are employed to encode the binding molecule of the invention, the resulting expressed polypeptides may need to be brought into contact in order to form the binding molecules of the invention.

In accordance with the present invention, the term "nucleic acid molecule of the invention" encompasses both a single nucleic acid molecule as well as a plurality of nucleic acid molecules, as long as all the components of the binding molecule of the invention are encoded thereby.

The present invention further relates to a vector comprising the nucleic acid molecule of the invention.

Preferably, the vector is a plasmid, cosmid, virus, bacteriophage or another vector used conventionally e.g. in genetic engineering.

The nucleic acid molecule of the present invention may be inserted into several commercially available vectors. Non-limiting examples include prokaryotic plasmid vectors, such as pQE-12, the pUC-series, pBluescript (Stratagene), the pET-series of expression vectors (Novagen) or pCRTOPO (Invitrogen), lambda gt11, pJOE, the pBBR1-MCS series, pJB861, pBSMuL, pBC2, pUCPKS, pTACT1 and vectors compatible with expression in mammalian cells like E-027 pCAG Kosak-Cherry (L45a) vector system, pREP (Invitrogen), pCEP4 (Invitrogen), pMC1neo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Invitrogen). Another vector suitable for expressing proteins in *Xenopus* embryos, zebrafish embryos as well as a wide variety of mammalian and avian cells is the multipurpose expression vector pCS2+.

The nucleic acid molecule of the present invention referred to above may also be inserted into vectors such that a translational fusion with another nucleic acid molecule is generated. The other nucleic acid molecules may e.g. encode a protein that increases the solubility and/or facilitates the purification of the binding molecule encoded by the nucleic acid molecule of the invention or a protein of interest that is to be observed by fluorescence imaging. Non-limiting examples of such vectors include pET32, pET41, pET43. The vectors may also contain an additional expressible polynucleotide coding for one or more chaperones to facilitate correct protein folding. Suitable bacterial expression hosts comprise e. g. strains derived from TG1, BL21 (such as BL21(DE3), BL21(DE3)PlysS, BL21(DE3)RIL, BL21 (DE3)PRARE) or Rosettaâ.

For vector modification techniques, see Sambrook and Russel, 2001. Generally, vectors can contain one or more origins of replication (ori) and inheritance systems for cloning or expression, one or more markers for selection in the host, e.g., antibiotic resistance, and one or more expression cassettes. Suitable origins of replication include, for example, the Col E1, the SV40 viral and the M 13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Such regulatory sequences are well known to those skilled in the art and include, without being limiting, regulatory sequences ensuring the initiation of transcription, internal ribosomal entry sites (IRES) (Owens, Proc. Natl. Acad. Sci. USA 98 (2001), 1471-1476) and optionally regulatory elements ensuring termination of transcription and stabilization of the transcript. Non-limiting examples for regulatory elements ensuring the initiation of transcription comprise a translation initiation codon, enhancers such as e.g. the SV40-enhancer, insulators and/or promoters, such as for example the cytomegalovirus (CMV) promoter, SV40-promoter, RSV-promoter (Rous sarcome virus), the lacZ promoter, chicken beta-actin promoter, CAG-promoter (a combination of chicken beta-actin promoter and cytomegalovirus immediate-early enhancer), the gai10 promoter, human elongation factor 1α-promoter, AOX1 promoter, GAL1 promoter CaM-kinase promoter, the lac, trp or tac promoter, the lacUV5 promoter, the autographa californica multiple nuclear polyhedrosis virus (AcMNPV) polyhedral promoter or a globin intron in mammalian and other animal cells. The lac promoter is a typical inducible promoter, useful for prokaryotic cells, which can be induced using the lactose analogue isopropylthiol-b-D-galactoside ("IPTG"). Non-limiting examples for regulatory elements ensuring transcription termination include the V40-poly-A site, the tk-poly-A site or the SV40, lacZ or AcMNPV polyhedral polyadenylation signals, which are to be included downstream of the nucleic acid sequence of the invention. Additional regulatory elements may include translational enhancers, Kozak sequences and intervening sequences flanked by donor and acceptor sites for RNA splicing, nucleotide sequences encoding secretion signals or, depending on the expression system used, signal sequences capable of directing the expressed polypeptide to a cellular compartment. For example an N-terminal flanking sequence or "leader sequence", which is also referred to as "signal peptide" in the art, may be included. The skilled person can choose suitable leader sequences without further ado. A leader sequence is preferably employed for the expression of any antibody chain (including light chain, heavy chain) or domain but is no longer required in the expressed, mature construct. Moreover, elements such as origin of replication, drug resistance gene, regulators (as part of an inducible promoter) may also be included.

An expression vector according to this invention is capable of directing the replication, and the expression of the nucleic acid molecule of the invention and the binding molecule encoded thereby.

The co-transfection with a selectable marker such as dhfr, gpt, neomycin, hygromycin allows the identification and isolation of the transfected cells. The transfected nucleic acid can also be amplified to express large amounts of the encoded binding molecule. The DHFR (dihydrofolate reductase) marker is useful to develop cell lines that carry several hundred or even several thousand copies of the gene of interest. Another useful selection marker is the enzyme glutamine synthase (GS) (Murphy et al. 1991; Bebbington et al. 1992). Using these markers, the cells are grown in selective medium and the cells with the highest resistance are selected. Expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria.

The nucleic acid molecules of the invention as described herein above may be designed for direct introduction or for introduction via electroporation (using for example Multiporator (Eppendorf) or Genepulser (BioRad)), PEI (Polysciences Inc. Warrington, Eppelheim), $Ca^{2+}$-mediated transfection or via liposomes (for example: "Lipofectamine" (Invitrogen)), non-liposomal compounds (for example: "Fugene" (Roche)), liposomes, phage vectors or viral vectors (e.g. adenoviral, retroviral, lentiviral) into cells. Additionally, baculoviral systems or systems based on Vaccinia Virus or Semliki Forest Virus can also be used as vector in eukaryotic expression system for the nucleic acid molecules of the invention. Expression vectors derived from viruses such as retroviruses, vaccinia virus, adeno-associated virus, herpes viruses, or bovine papilloma virus, may be used for delivery of the nucleic acid molecules or vector into targeted cell population. Methods which are well known to those skilled in the art can be used to construct recombinant viral vectors; see, for example, the techniques described in Sambrook, 2001 and Ausubel, 2001.

It will be appreciated that where the binding molecule of the invention is encoded by more than one nucleic acid molecule, said plurality of nucleic acid molecules may be comprised in one or in a plurality of vectors. The term "the vector of the invention" encompasses both a single vector as well as a plurality of vectors, as long as all the components of the binding molecule of the invention are encoded thereby.

The present invention further relates to a host cell or a non-human host transformed with the vector of the invention.

Said host or host cell may be produced by introducing the vector of the invention into a host or host cell, which upon its presence mediates the expression of the binding molecule encoded by the vector.

In accordance with the present invention, the host may be a transgenic non-human animal transfected with and/or expressing the vector of the present invention. In a preferred embodiment, the transgenic animal is a mammal, e.g. a hamster, cow, cat, pig, dog or horse.

In a preferred embodiment, the host is a cell, such as an isolated cell which may be part of a cell culture.

Suitable prokaryotic host cells comprise e.g. bacteria of the species *Escherichia*, *Bacillus*, *Streptomyces* and *Salmonella typhimurium*. Suitable eukaryotic host cells are e.g. fungal cells, inter alia, yeasts such as *Saccharomyces cerevisiae* or *Pichia pastoris* or insect cells such as *Drosophila* S2 and *Spodoptera* Sf9 cells and plant cells as well as mammalian cells. Appropriate culture mediums and conditions for the above-described host cells are known in the art.

Mammalian host cells include without being limiting human Hela, HEK293, H9 and Jurkat cells, mouse NIH3T3 and C127 cells, COS 1, COS 7 and CV1, quail QC1-3 cells, mouse L cells, Chinese hamster ovary (CHO) cells and Bowes melanoma cells. Alternatively, the binding molecule of the invention can be expressed in stable cell lines that contain the gene construct encompassing the nucleic acid molecule or the vector of the invention integrated into a chromosome.

In another preferred embodiment, said cell is a primary cell or primary cell line. Primary cells are cells which are directly obtained from an organism. Suitable primary cells are, for example, mouse embryonic fibroblasts, mouse primary hepatocytes, cardiomyocytes and neuronal cells as well as mouse muscle stem cells (satellite cells) and stable, immortalized cell lines derived thereof.

The present invention also relates to a method for the production of a binding molecule according to the invention comprising culture of the host cell of the invention under suitable conditions and isolation of the binding molecule produced by said host cell.

Suitable conditions for culturing a prokaryotic or eukaryotic host are well known to the person skilled in the art. For example, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be overexpressed. In general, the skilled person is also aware that these conditions may have to be adapted to the needs of the host and the requirements of the binding molecule expressed. In case an inducible promoter controls the nucleic acid molecule of the invention in the vector present in the host cell, expression of the binding molecule can be induced by addition of an appropriate inducing agent. Suitable expression protocols and strategies are known to the skilled person.

Depending on the cell type and its specific requirements, mammalian cell cultures can e.g. be carried out in RPMI or DMEM medium containing 10% (v/v) FCS, 2 mM L-glutamine and 100 U/ml penicillin/streptomycine. The cells can be kept at 37° C. in a 5% $CO_2$, water saturated atmosphere.

Suitable media for insect cell culture is e.g. TNM+10% FCS or SF900 medium. Insect cells are usually grown at 27° C. as adhesion or suspension culture.

Suitable expression protocols for eukaryotic cells are well known to the skilled person and can be retrieved e.g. from in Sambrook, 2001, loc cit.

Methods of isolating the binding molecule produced are well-known in the art and comprise without being limiting method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001, loc. cit.

The present invention also provides a composition comprising at least one of (i) the binding molecule of the invention, (ii) the nucleic acid molecule of the invention; (iii) the vector of the invention or (iv) the host cell of the invention.

The term "composition", as used in accordance with the present invention, relates to a composition which comprises at least one of the recited compounds. It may, optionally, comprise further molecules capable of altering the characteristics of the compounds of the invention thereby, for example, stabilizing, modulating and/or enhancing their function. The composition may be in solid or liquid form and may be, inter alia, in the form of (a) powder(s), (a) tablet(s) or (a) solution(s).

In a preferred embodiment, the composition is a pharmaceutical composition optionally further comprising a pharmaceutically acceptable carrier.

In accordance with the present invention, the term "pharmaceutical composition" relates to a composition for administration to a patient, preferably a human patient. The pharmaceutical composition of the invention comprises the compounds recited above. The pharmaceutical composition of the present invention may, optionally and additionally, comprise a pharmaceutically acceptable carrier. By "pharmaceutically acceptable carrier" is meant a non-toxic solid, semisolid or liquid filler, diluent, encapsulating material or formulation auxiliary of any type. Examples of suitable pharmaceutical carriers are well known in the art and include sodium chloride solutions, phosphate buffered sodium chloride solutions, water, emulsions, such as oil/water emulsions, various types of wetting agents, sterile solutions, organic solvents etc. Preferably the carrier is a parenteral carrier, more preferably a solution that is isotonic with the blood of the recipient. The term "parenteral" as used herein refers to modes of administration which include intravenous, intramuscular, intraperitoneal, intrasternal, subcutaneous and intraarticular injection and infusion. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or further immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

Compositions comprising such carriers can be formulated by well known conventional methods. Generally, the formulations are prepared by contacting the components of the pharmaceutical composition uniformly and intimately with liquid carriers or finely divided solid carriers or both. Then, if necessary, the product is shaped into the desired formulation.

These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The therapeutically effective amount for a given situation will readily be determined by routine experimentation and is within the skills and judgment of the ordinary clinician or physician. The pharmaceutical composition may be for administration once or for a regular administration over a prolonged period of time. Generally, the administration of the pharmaceutical composition should be in the range of for example 10 µg/kg of body weight to 2 g/kg of body weight for a single dose. However, a more preferred dosage might be in the range of 100 µg/kg to 1.5 g/kg of body weight, even more preferably 1 mg/kg to 1 g/kg of body weight and even more preferably 5 mg/kg to 500 mg/kg of body weight for a single dose.

Administration of pharmaceutical compositions of the invention may be effected by different ways, e.g., by intravenous, intraperitoneal, subcutaneous, intramuscular, intradermal, intranasal or intrabronchial administration.

The components of the pharmaceutical composition to be used for therapeutic administration must be sterile. Sterility is readily accomplished by filtration through sterile filtration membranes (e.g., 0.2 micron membranes).

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic water-for-injection. Preservatives and other additives may also be present such as, for example, antimicrobials, anti oxidants, chelating agents, and inert gases and the like. The pharmaceutical composition may comprise further agents depending on the intended use of the pharmaceutical composition.

The pharmaceutical composition may be particularly useful for the treatment of tumors, as disclosed below.

In another preferred embodiment, the composition of the invention is a diagnostic composition.

In accordance with the present invention, the term "diagnostic composition" relates to compositions for diagnosing individual patients for their potential response to or curability by the pharmaceutical compositions of the invention. The diagnostic composition of the invention comprises the compounds recited above. The diagnostic composition may further comprise appropriate buffer(s) etc. The diagnostic compositions may be packaged in a container or a plurality of containers.

The present invention further relates to the binding molecule of the invention, the nucleic acid molecule of the invention or the vector of the invention for use in the treatment of tumors.

The term "tumor", in accordance with the present invention refers to a class of diseases or disorders characterized by uncontrolled division of cells and encompasses all types of tumors, such as e.g. cancerous tumors and benign tumors as well as solid tumors and non-solid tumors. Cancerous tumors are further characterized by the ability of these tumors to spread, either by direct growth into adjacent tissue through invasion, or by implantation into distant sites by metastasis (where tumor cells are transported through the bloodstream or lymphatic system).

Preferably, the tumor is a cancerous tumor selected from the group consisting of breast cancer, ovarian cancer, bladder cancer, salivary gland cancer, endometrium cancer, pancreatic cancer, thyroid cancer, kidney cancer, lung cancer, cancer concerning the upper gastrointestinal tract, colon cancer, colorectal cancer, prostate cancer, squamous-cell carcinoma of the head and neck, cervical cancer, glioblastomas, malignant ascites, lymphomas and leukemias.

All of the cancer types described herein are well known to the skilled person and are defined in accordance with the pertinent art and the common general knowledge of the skilled person.

The figures show:

FIG. 1: FACS binding experiments using HER2 overexpressing BT-474 cells.

(A) Binding of Fyn SH3 derived polypeptides C12 (SEQ ID NO: 1) and G10 (SEQ ID NO: 2) on HER2 with or without pre-blocking of the epitope of the anti-HER2 antibody 1 (anti-HER2 mAb 1; wherein the heavy chain has the amino acid sequence of SEQ ID NO: 154 and the light chain has the amino acid sequence of SEQ ID NO: 155; exemplary nucleic acid molecules encoding the heavy and light chain are shown in SEQ ID NO: 165 and 166) and anti-HER2 antibody 2 (anti-HER2 mAb 2; wherein the heavy chain has the amino acid sequence of SEQ ID NO: 160 and the light chain has the amino acid sequence of SEQ ID NO: 163; exemplary nucleic acid molecules encoding the heavy and light chain are shown in SEQ ID NO: 168 and 169). PBS, phosphate buffered saline, represents the negative control.

(B) Binding of biotinylated anti-HER2 antibody 1 and biotinylated anti-HER2 antibody 2 (biotinylated antibodies are indicated with the abbreviation "bt") with or without pre-blocking of the epitope of the anti-HER2 antibody 1 and anti-HER2 antibody 2. PBS, phosphate buffered saline, represents the negative control.

Figure 2:
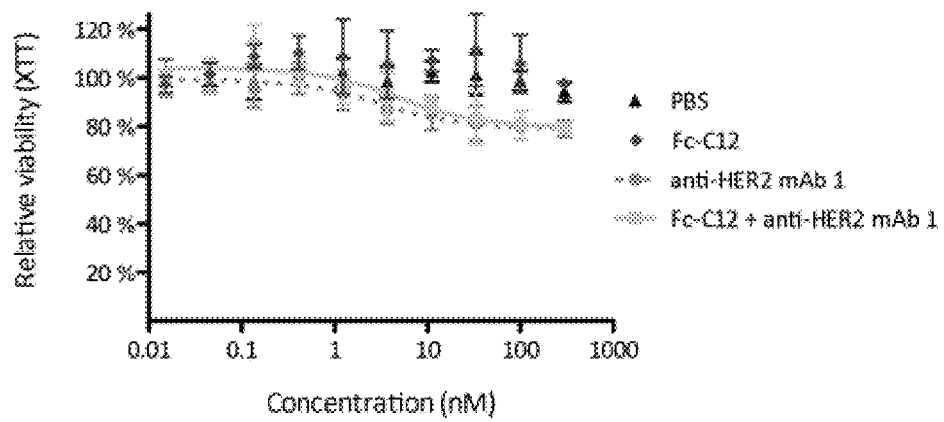
Figure 2:
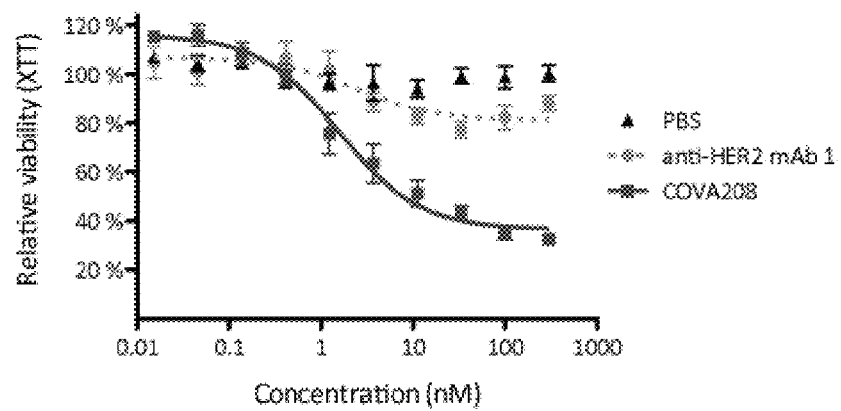
Figure 2:
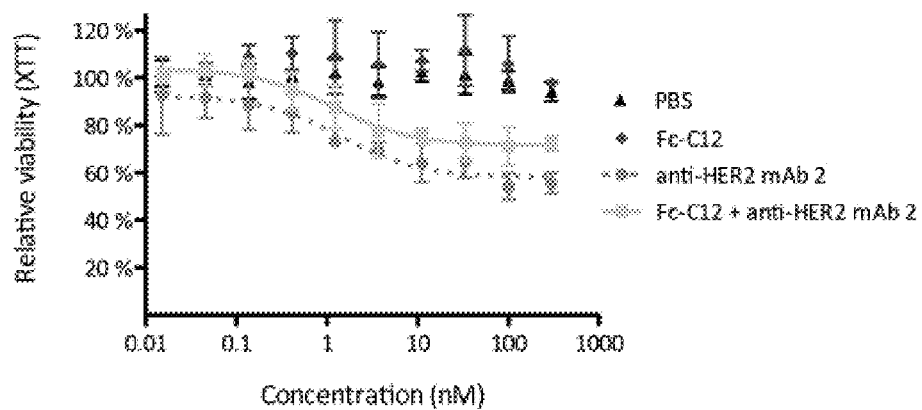
Figure 2:
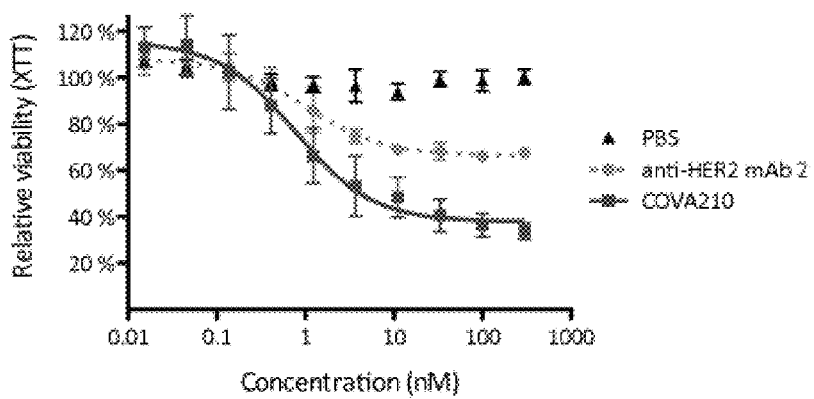

FIG. 2: In vitro proliferation assays with HER2 overexpressing gastric cancer cell line NCI-N87.

Fyn SH3-derived polypeptide C12 (SEQ ID NO:1) was fused to the Fc part of a human IgG1 to create the monospecific bivalent protein called Fc-C12 (SEQ ID NO: 153). The combination mixture of Fynomer C12-Fc with the anti-HER2 antibody 1 (anti-HER2 mAb 1) (shown in FIG. 2A) and with the anti-HER2 antibody 2 (anti-HER2 mAb 2) (shown in FIG. 2C) did not reduce proliferation rate of NCI-N87 cells more effectively than the corresponding anti-HER2 antibodies alone. However, the anti-proliferative activity of the binding molecules COVA208 (SEQ ID NO: 154 & 159) (shown in FIG. 2B) and COVA210 (SEQ ID NO: 160 & 161; an exemplary nucleic acid molecule encoding SEQ ID NO:161 is shown in SEQ ID NO: 170) (FIG. 2D) was higher than the activity of the corresponding unmodified antibody. COVA 208 consists of the fusion of C12 (SEQ ID NO:1) to the N-terminus of the light chain of antibody 1 (SEQ ID NO: 154 and 155)) and COVA210 consists of the fusion of C12 (SEQ ID NO:1) to the N-terminus of the light chain of antibody 2 (SEQ ID NO: 160 and 163), see also FIG. 8.

Figure 3:
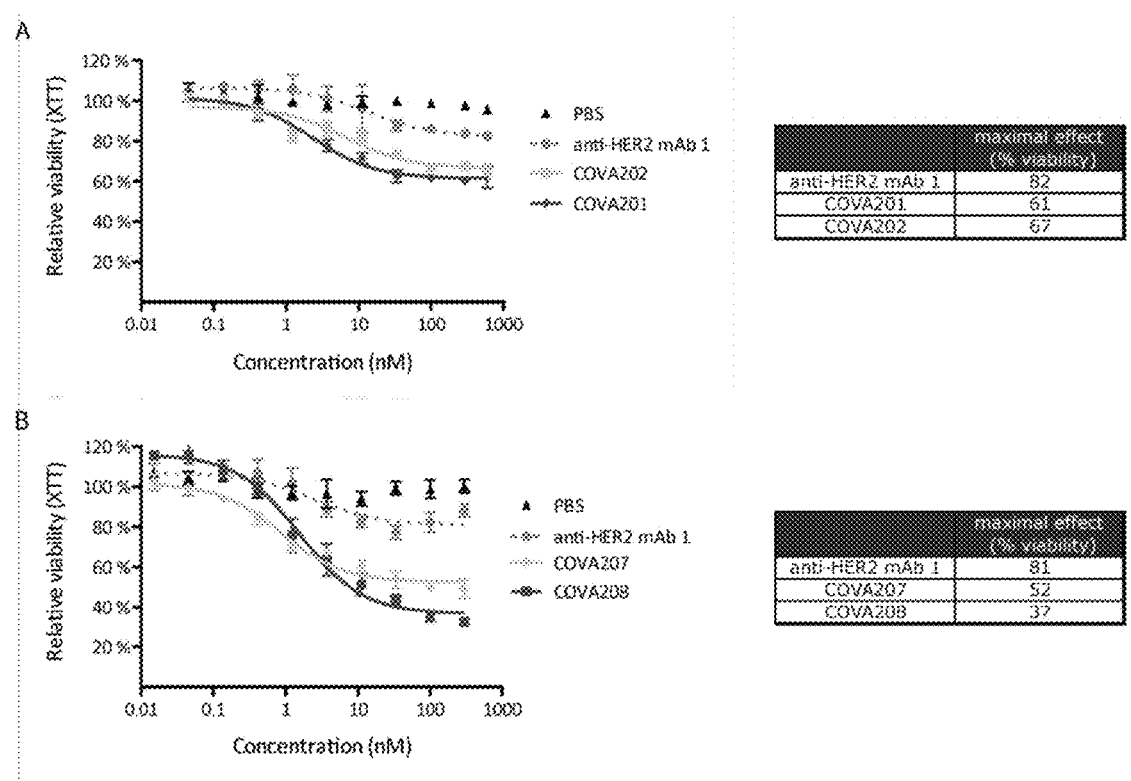

FIG. 3: The anti-proliferative activity of anti-HER2 Fynomer-antibody fusions varies depending on the relative orientation of the Fynomer and the binding site of the antibody. The anti-proliferative activities of the different Fynomer-antibody fusion proteins in a proliferation cell assay with NCI-N87 gastric cancer cells showed variations (A) and (B), and COVA208 showed the best anti-proliferative effects on this cell line (FIG. 3B). The maximal effects are indicated in the tables and given in percentage of viability. COVA201 (SEQ ID NOs: 156 and 155), COVA202 (SEQ ID NOs: 154 and 157), COVA207 (SEQ ID NOs: 158 and 155) and COVA208 (SEQ ID NOs: 154 and 159) are all fusion proteins of the Fyn SH3 derived polypeptide C12 (SEQ ID NO: 1) and anti-HER2 antibody 1 (anti-HER2 mAb 1) (SEQ ID NOs: 154 and 155). COVA201 consists of the C-terminal heavy chain fusion, COV202 represents the C-terminal light chain fusion, COVA 207 consists of the N-terminal heavy chain fusion and COVA208 represents the N-terminal light chain fusion, see also FIG. 8.

Figure 4:
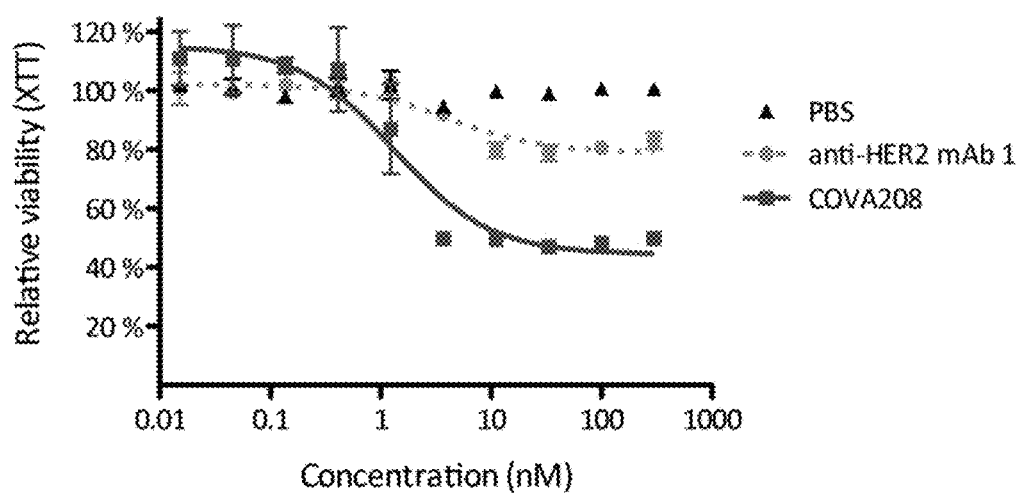

FIG. 4: The anti-proliferative activity of COVA208 (SEQ ID NOs: 154 and 159) (fusion of Fynomer C12 to the N-terminus of the light chain of anti-HER2 antibody 1 (anti-HER2 mAb 1, SEQ ID NOs: 154 and 155)) was determined in a cell assay with the HER2 overexpressing breast cancer cell line BT-474. COVA208 exhibited superior anti-proliferative activity as compared to the unmodified antibody.

Figure 5:
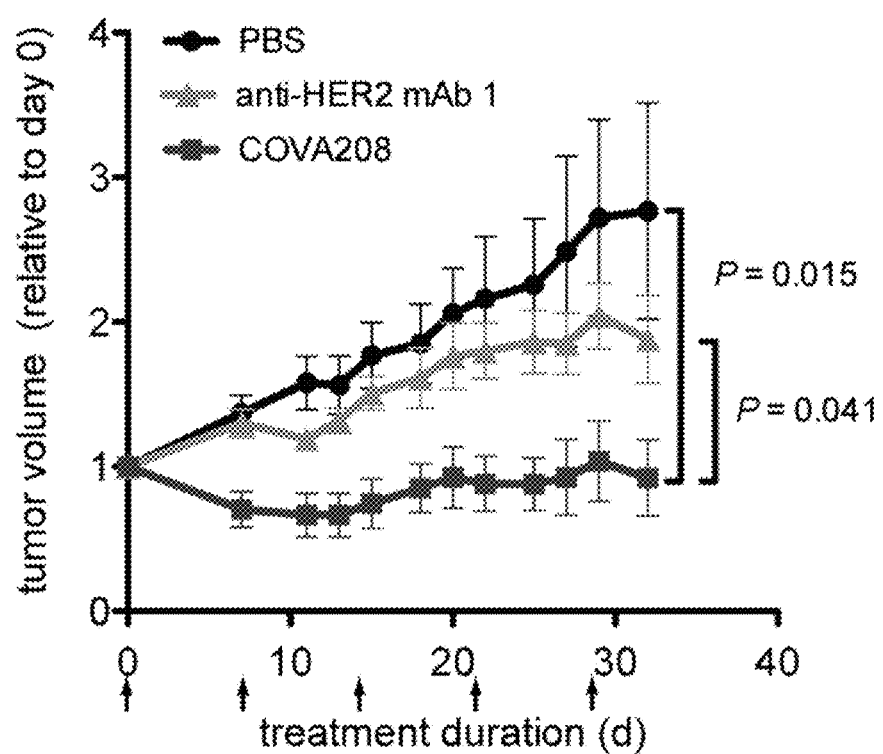

FIG. 5: depicts an animal study with a NCI-N87 gastric cancer xenograft mouse model. NCI-N87 gastric cancer cells were inoculated subcutaneously in CD1 Nude mice (n=6 per treatment group). When tumors reached a size of about 140 mm$^3$, animals were treated with a loading dose of 30 mg/kg COVA208 (SEQ ID NOs: 154 and 159), anti-HER2 antibody 1 (anti-HER2 mAb 1 (SEQ ID NOs: 154 and 155)) or placebo (PBS). Treatment was continued with four weekly i.p. injections (15 mg/kg) (indicated with the arrows) and size of tumors was measured with a caliper. COVA208 was found to inhibit tumor growth significantly better than the monospecific anti-HER2 antibody 1 or placebo (PBS). Mean tumor volumes of 6 mice are shown (relative to day 0 when the treatment was started)±standard error of the mean (SEM).

Figure 6:
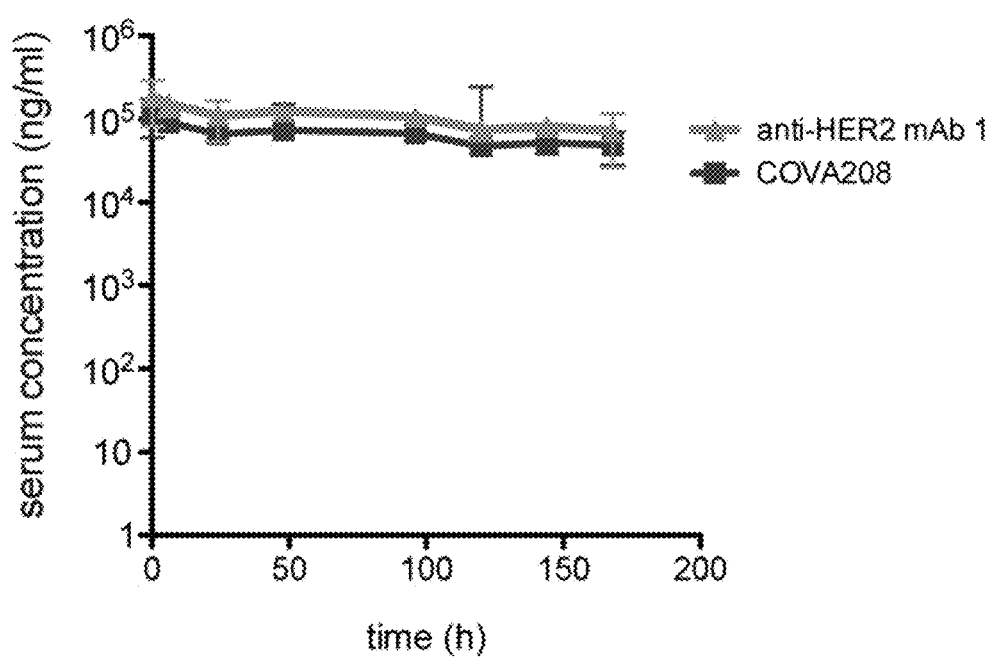

FIG. 6: Serum concentrations of COVA208 (SEQ ID NOs: 154 and 159) and the anti-HER2 antibody 1 (anti-HER2 mAb 1 (SEQ ID NOs: 154 and 155)) at different time-points after a single i.v. injection into C57Bl/6 mice. The six last time-points were used to calculate the terminal half-lives of 247 h (COVA208) and 187 h (anti-HER2 antibody 1). Mean serum concentrations are plotted versus time, error bars represent standard deviations (SD).

Figure 7:
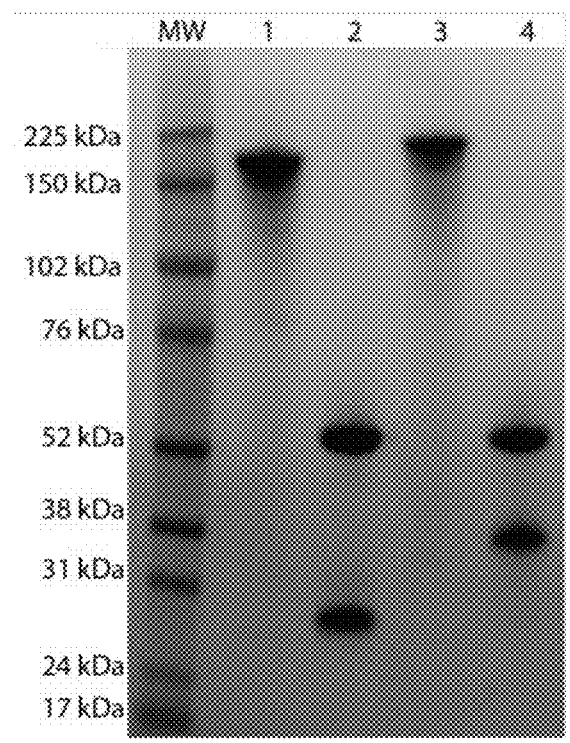
Figure 7:
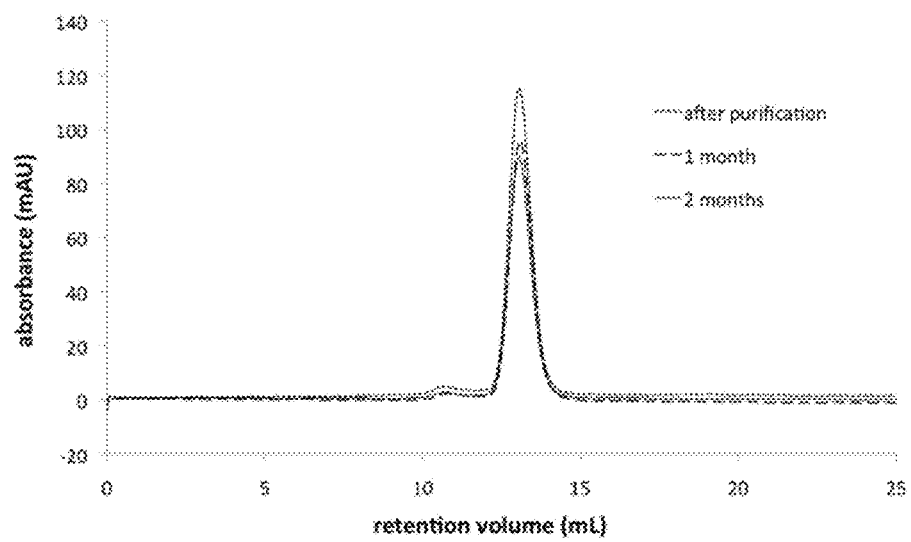

FIG. 7: SDS PAGE of COVA208 (SEQ ID NOs: 154 and 159) and anti-HER2 antibody 1 (anti-HER2 mAb 1 (SEQ ID NO: 154 and 155)) (top) and size exclusion chromatograms of COVA208 after purification and after a storage period of 1 and 2 months at 4° C. (bottom). Evidently, COVA208 did not form any aggregates.

Figure 8:
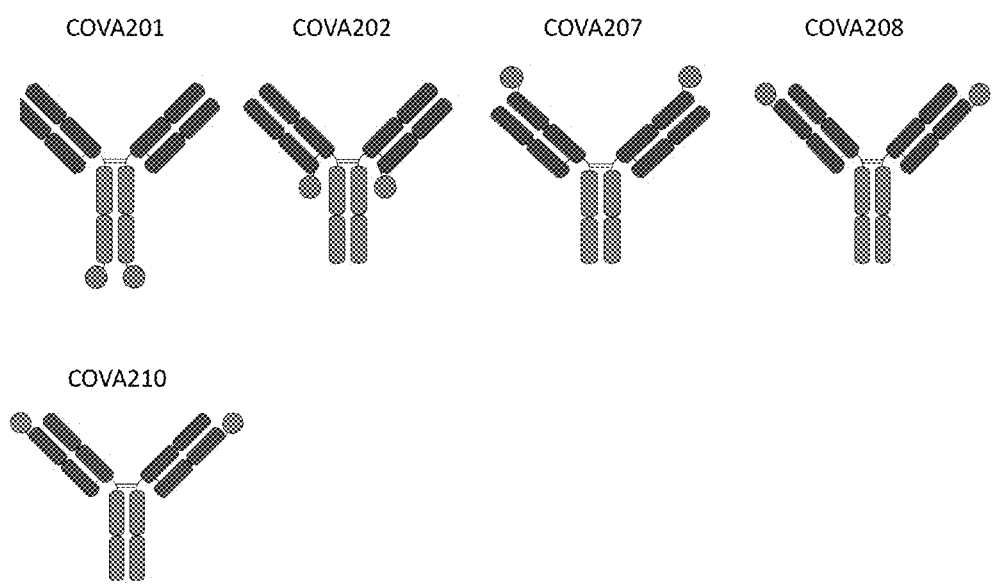

FIG. 8: Schematic overview of different formats of binding molecules that bind to two different epitopes on an antigen. COVA201 (SEQ ID NO: 156 & 155), COVA202 (SEQ ID NO: 154 & 157), COVA207 (SEQ ID NO: 158 & 155) and COVA208 (SEQ ID NO: 154 & 159) are all fusion proteins of the Fyn SH3 derived polypeptide C12 (SEQ ID NO: 1) and anti-HER2 antibody 1 (anti-HER2 mAb 1) (SEQ ID NO: 154 and 155). COVA201 consists of the C-terminal heavy chain fusion, COV202 represents the C-terminal light chain fusion, COVA 207 consists of the N-terminal heavy chain fusion and COVA208 represents the N-terminal light chain fusion. COVA210 (SEQ ID NO: 160 & 161) consists of the fusion of C12 (SEQ ID NO:1) to the N-terminus of the light chain of antibody 2 (SEQ ID NO: 160 and 163).

Figure 9:
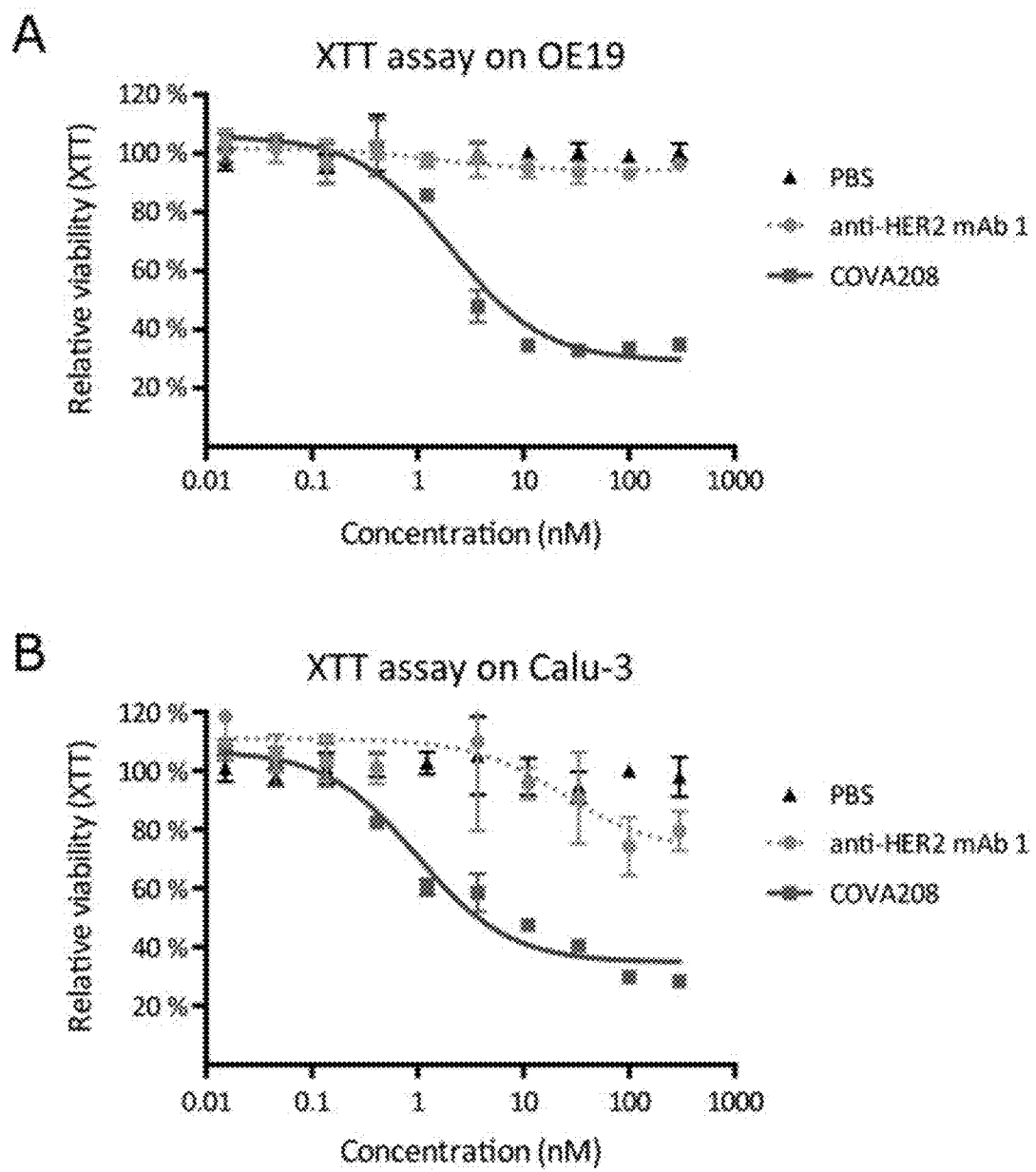
Figure 9:
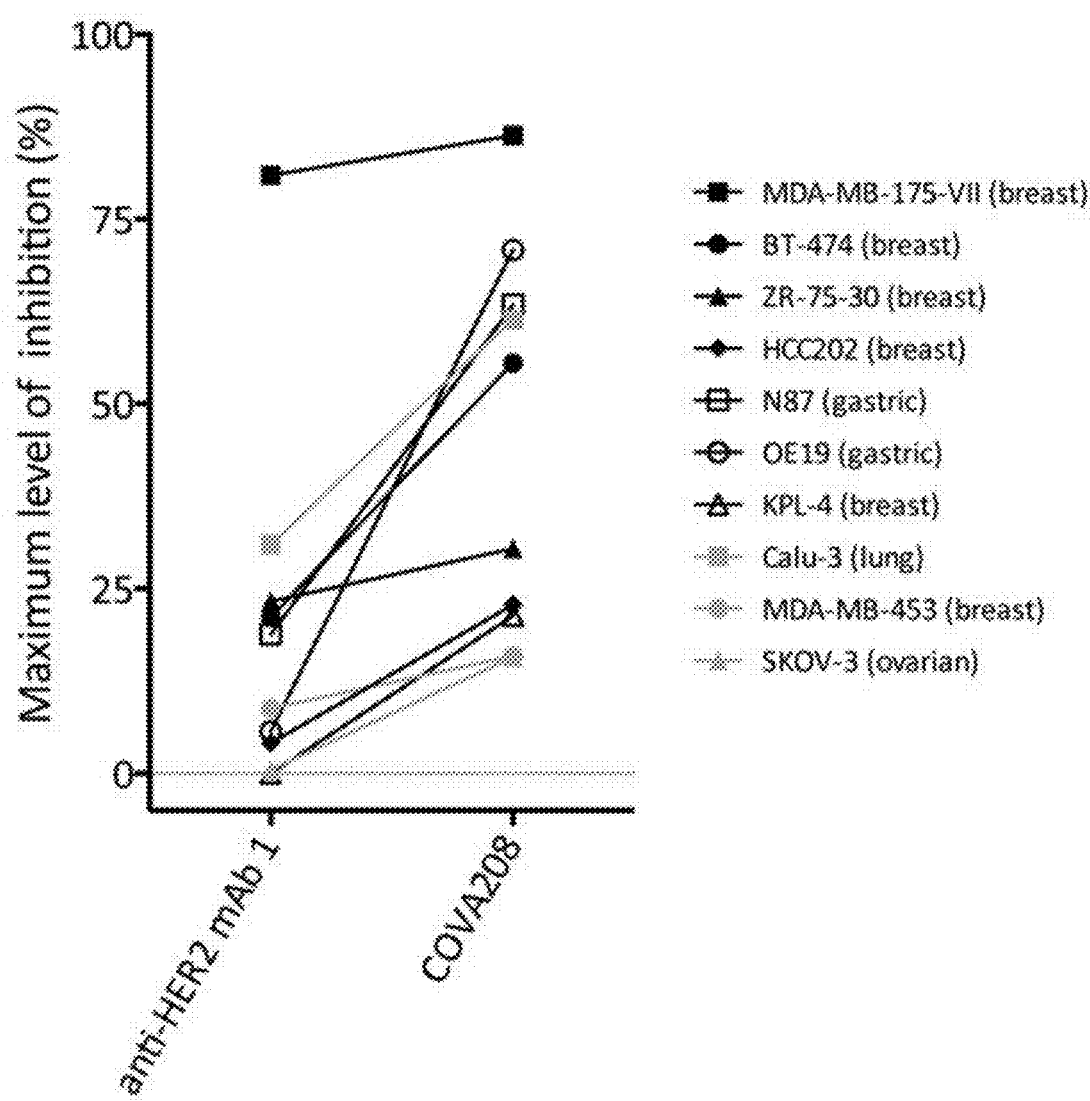

FIG. 9: In vitro proliferation assays with HER2 expressing cell lines. COVA208 (SEQ ID NOs: 154 and 159) inhibited the cell growth of OE19 (FIG. 9A) and of Calu-3 cells (FIG. 9B) more effectively than anti-HER2 antibody 1

(anti-HER2 mAb 1 (SEQ ID NOs: 154 and 155)). FIG. 9C summarizes the results of the in vitro proliferation assays performed on 10 different cell lines, for each of which the maximal level of inhibition has been plotted. The corresponding data points for COVA208 and anti-HER2 antibody 1 were connected to facilitate the comparison between the two compounds.

COVA208 shows improved inhibition of cell growth as compared to anti-HER2 antibody 1 on all 10 cell lines.

Figure 10:
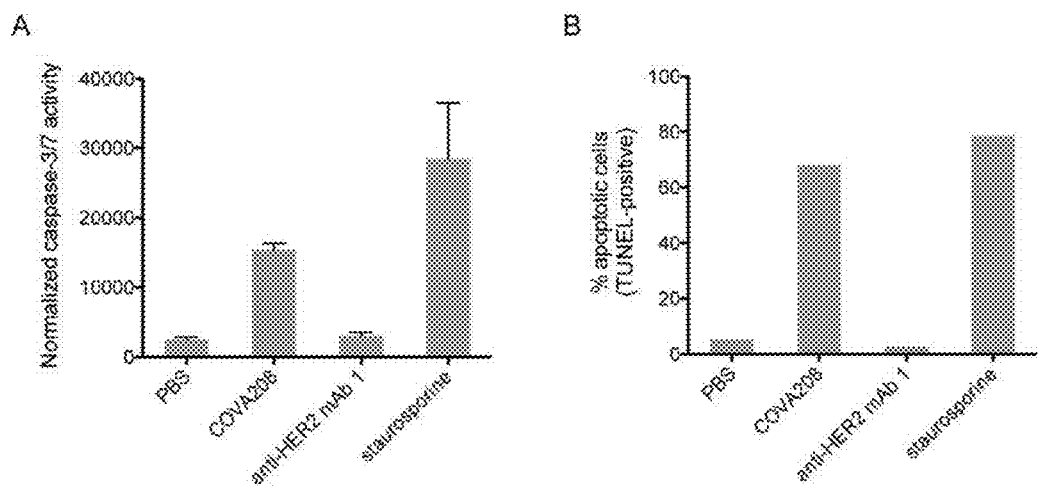

FIG. 10: COVA208 (SEQ ID NOs: 154 and 159) is capable of inducing apoptosis, as determined by caspase-3/7 activity (FIG. 10A) and by TUNEL staining (FIG. 10B). Anti-HER2 antibody 1 (anti-HER2 mAb 1 (SEQ ID NOs: 154 and 155)) did not increase caspase-3/7 activity nor the fraction of TUNEL-positive cells, indicating that the ability to induce apoptosis is unique to COVA208. Staurosporine was used as positive control. Error bars in FIG. 10A indicate standard deviation of triplicates.

Figure 11:
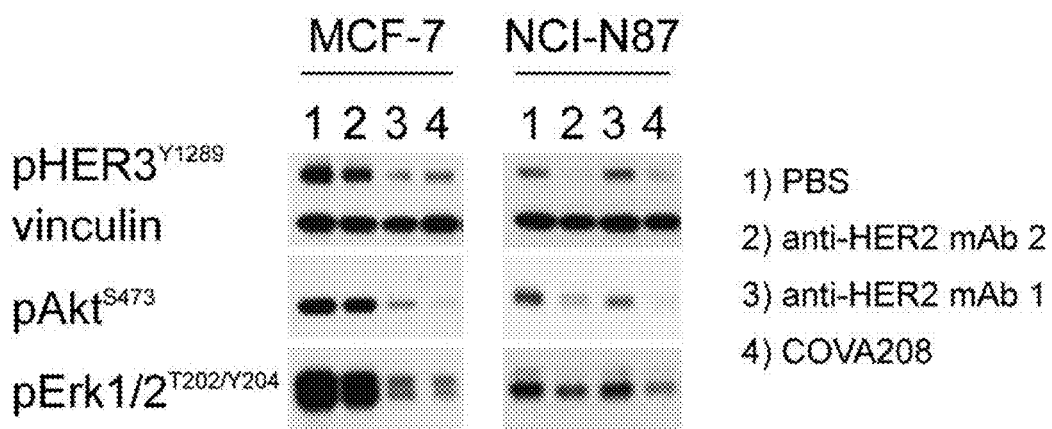

FIG. 11: COVA208 (SEQ ID NOs: 154 and 159) inhibits ligand-dependent activation of HER2 signaling on MCF-7 cells (left panel) as well as ligand-independent activation of HER2 signaling on NCI-N87 cells (right panel). Anti-HER2 antibody 1 (anti-HER2 mAb 1 (SEQ ID NOs: 154 and 155)) inhibits signaling only on MCF-7 cells, whereas anti-HER2 antibody 2 (anti-HER2 mAb 2 (SEQ ID NOs: 160 and 163)) is only active on NCI-N87 cells. Vinculin served as a loading control.

Figure 12:
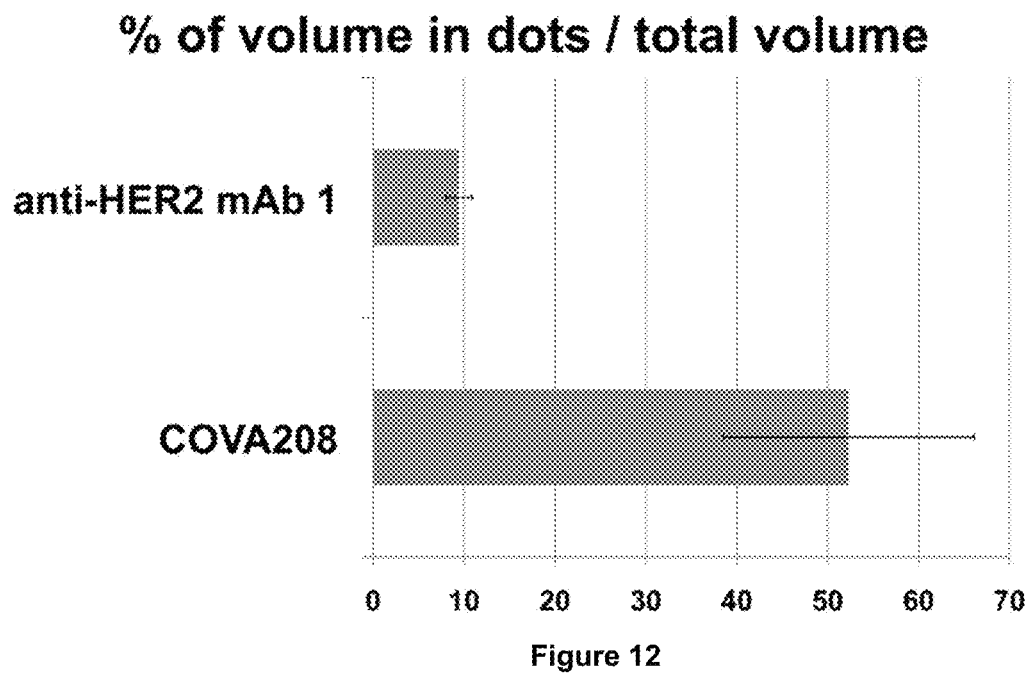

FIG. 12: COVA208 is internalized by NCI-N87 cells. After surface staining followed by 5 h incubation, 52% of COVA208 (SEQ ID NOs: 154 and 159) was found in spherical dots within the cytosol, as determined from confocal laser scanning images analyzed with Imaris software. Anti-HER2 antibody 1 (anti-HER2 mAb 1 (SEQ ID NOs: 154 and 155)) staining primarily remained membrane-associated, with only 9% of the staining localized in cytosolic spherical dots.

Figure 13:
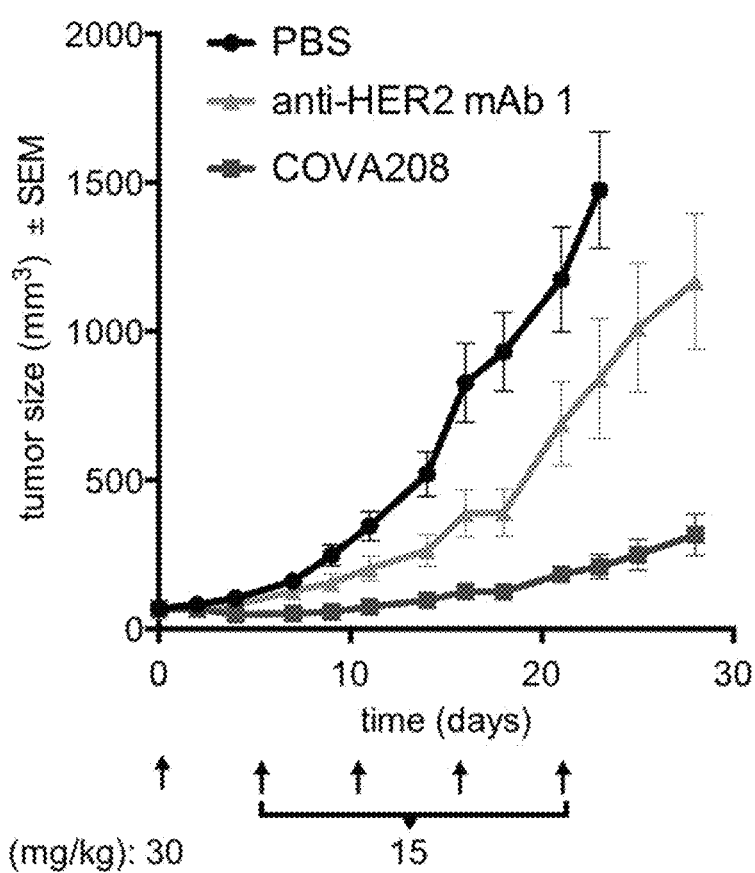

FIG. 13: depicts an animal study with a KPL-4 breast cancer xenograft mouse model. KPL-4 breast cancer cells were inoculated subcutaneously in SCID beige mice (n=8 per treatment group). When tumors reached a size of about 70 mm³, animals were treated with a loading dose of 30 mg/kg COVA208 (SEQ ID NOs: 154 and 159), anti-HER2 antibody 1 (anti-HER2 mAb 1 (SEQ ID NOs: 154 and 155)) or placebo (PBS). Treatment was continued with four weekly i.p. injections (15 mg/kg) (indicated with the arrows) and size of tumors was measured with a caliper. COVA208 was found to inhibit tumor growth significantly better than the monospecific anti-HER2 antibody 1 or placebo (PBS). Mean tumor volumes of 8 mice are shown±standard error of the mean (SEM).

The examples illustrate the invention:

Example 1

Fyn SH3 Derived Polypeptides Bind to HER2

Methods
1) Phage ELISA on Recombinant HER2 Protein
DNA encoding the amino acids shown in SEQ ID NOs: 9 to 121 were cloned into the phagemid vector pHEN1 as described for the Fyn SH3 library in Grabulovski et al. (Grabulovski et al. (2007) JBC, 282, p. 3196-3204). Phage production was performed according to standard protocols (Viti, F. et al. (2000) Methods Enzymol. 326, 480-505). Monoclonal bacterial supernatants containing phages were used for ELISA: biotinylated extracellular domain of HER2 comprising amino acids 23-652 of the full-length protein (purchased from Bender Medsystems, or from R&D as fusion to human Fcγ1; biotinylation was performed with sulfo-NHS-LC-biotin (Pierce) according to the manufacturer's instructions) was immobilized on streptavidin-coated wells (StreptaWells, High Bind, Roche), and after blocking with 2% milk (Rapilait, Migros, Switzerland) in PBS, 20 µl of 10% milk in PBS and 80 µl of phage supernatants were applied. After incubation for 1 hr, unbound phage were washed off, and bound phages were detected with anti-M13-HRP antibody conjugate (GE Healthcare). The detection of peroxidase activity was done by adding BM blue POD substrate (Roche) and the reaction was stopped by adding 1 M $H_2SO_4$. The phage ELISA positive clones were tested by phage ELISA for the absence of cross reactivity to Streptavidin (StreptaWells, High Bind, Roche) and to human IgG (Sigma).

The DNA sequence of the specific binders was verified by DNA sequencing.

2) FACS Experiment on HER2 Overexpressing SKOV-3 Cells

DNA encoding the polypeptides shown in SEQ ID NOs: 1 to 8 and SEQ ID NOs: 122-152 were subcloned into the bacterial expression vector pQE12 so that the resulting constructs carried a C-terminal myc-hexahistidine tag (SEQ ID NO: 162) as described in Grabulovski et al. (Grabulovski et al. (2007) JBC, 282, p. 3196-3204). The polypeptides were expressed in the cytosol of E. coli bacteria, and 1.8 ml of cleared lysate was prepared per ml original culture. 100 µl cleared lysate containing the polypeptides was mixed with 100 µl cell suspension containing $1.25 \times 10^5$ SKOV-3 cells in PBS/1% FCS/0.2% sodium azide. After 60 min incubation on ice, cells were washed, and bound sequences were detected by 10 µg/ml anti-myc mouse antibody 9E10 (Roche), followed by anti-mouse IgG-Alexa488 conjugate (Invitrogen). The stained cells were then analyzed in a FACS analyzer. The DNA sequence of the specific binders was verified by DNA sequencing.

Results:
The amino acid sequences of Fyn SH3 derived HER2 binders is presented in SEQ ID NOs: 1 to 152 as appended in the sequence listing.

Example 2

Fyn SH3 Derived Polypeptides Bind to Other Epitopes on HER2 Compared to Anti-HER2 Antibodies Methods:
The DNA sequences encoding FynSH3-derived clones 012 (SEQ ID NO: 1) and G10 (SEQ ID NO: 2) were subcloned into the bacterial expression vector pQE12 so that the resulting constructs carried a C-terminal myc-hexahistidine tag (SEQ ID NO: 162), and the two constructs were expressed and purified by means of the hexahistidine tag as described in Grabulovski et al. (Grabulovski et al. (2007) JBC, 282, p. 3196-3204).

The heavy and light chains (SEQ ID NO: 154 and SEQ ID NO: 155) of the anti-HER2 antibody 1 and the anti-HER2 antibody 2 (SEQ ID NO: 160 and SEQ ID NO: 163) were transiently co-expressed in CHO cells. The antibodies were purified from the culture supernatant by affinity chromatography on a MabSelect SuRe column (GE healthcare).

$10^5$ BT-474 cells (ATCC) were pre-incubated with an excess of 1 µM anti-HER2 antibody 1, anti-HER2 antibody 2, or PBS for 60 min on ice. Subsequently, 300 nM C12 or G10 plus 20 nM mouse anti-myc antibody 9E10 (Roche)

were added to the cells without washing off the blocking antibodies. After 45 min incubation, cells were washed and bound C12/9E10- and G10/9E10 complexes were detected with anti-mouse IgG-Alexa488 conjugate. The cells were analyzed by FACS. Binding of C12 and G10 to anti-HER2 antibody 1 or anti-HER2 antibody 2-blocked cell surface was compared against binding to non-blocked cells. In order to analyze the efficacy of the epitope blockade by anti-HER2 antibody 1 and 2, 25 nM biotinylated antibody (biotinylation was performed with sulfo-NHS-LC-biotin (Pierce) according to the manufacturer's instructions) was added to the pre-blocked cells, followed by detection with Streptavidin-allophycocyanin conjugate.

Results:

The results of the experiments are shown in FIG. 1. Preblocking with either of the antibodies drastically reduced binding of the corresponding biotinylated antibodies, indicating that the preblocking step efficiently and specifically blocked the epitopes of the two different antibodies (FIG. 1B).

Binding of C12 and of G10 was not affected by preblocking with anti-HER2 antibody 1 nor with anti-HER2 antibody 2, indicating that both clones bind to an epitope different to anti-HER2 antibody 1 and anti-HER2 antibody 2 (FIG. 1A).

Example 3

The Inventive Binding Molecules have a Stronger Antiproliferative Effect than the Combination of the Individual Binding Proteins HER2 targeting molecules with two different binding specificities were created by fusion of C12 via a glycine-serine $(Gly_4Ser)_3$ linker to the N-terminus of the light chain of anti-HER2 antibody 1 (resulting in the protein termed COVA208) or anti-HER2 antibody 2 (termed COVA210).

Methods:

Anti-HER2 antibody 1 (SEQ ID NO: 154 and SEQ ID NO:155), anti-HER2 antibody 2 (SEQ ID NO: 160 and SEQ ID NO: 163), COVA208 (SEQ ID NO: 154 and SEQ ID NO:159) and COVA210 (SEQ ID NO: 160, SEQ ID NO: 161) were transiently co-expressed in CHO cells and purified from the culture supernatant by affinity chromatography on a MabSelect SuRe column (GE healthcare). A bivalent monospecific format of clone C12 was created by fusion via a $(Gly_4Ser)_3$ to the C-terminus of human Fcγ1, resulting in Fc-C12 (SEQ ID NO: 153). The protein was expressed and purified as described above for anti-HER2 antibody 1, anti-HER2 antibody 2, COVA208 and COVA210.

The growth inhibitory effect of the HER2 targeting constructs was investigated in vitro on the NCI-N87 tumor cell line (purchased from ATCC). This human HER2 overexpressing gastric cell line was grown in RPMI1640 (Gibco) supplemented with 10% FBS (Gibco; heat inactivated at 56° C. for 45 min). 7000 cells in 100 µl growth medium per well were seeded into a 96-well plate. After incubation at 37° C./5% $CO_2$ for 24 h, 20 µl of the anti-HER2 constructs Fc-C12, COVA208, COVA210, anti-HER2 antibody 1 or anti-HER2 antibody 2, or combinations of the agents, were added. Each condition was performed in triplicate, and the agents were added in three-fold serial dilutions at concentrations between 300 nM and 0.015 nM. For combinations, each agent was used at the indicated concentration (e.g. 300 nM Fc-C12+300 nM anti-HER2 antibody 1). After 5 days, the viability of the treated cultures was analyzed with XTT (Roche). The XTT reagent is converted by metabolically active cells into a colored formazan product which absorbs light at 450 nm wavelength. The absorbance directly correlates with the live cell number. The % viability relative to PBS treated cells was calculated according to the formula:

$$\% \text{ viability} = \left( \frac{OD_{experimental} - OD_{blank}}{OD_{untreated} - OD_{blank}} \right) \times 100$$

The average % viability was plotted against $\log_{10}$(concentration), and the resulting dose-response curves were analyzed by nonlinear regression with the software Prism, using the three parameter equation:

$$\% \text{ viability} = \text{bottom} + \frac{\text{top} - \text{bottom}}{1 + 10^{x - LogIC_{50}}}$$

Results:

The fusion of Fyn SH3 derived binder C12 to the C-terminus of human Fcγ1, Fc-C12, did not have any effect on cell viability (FIGS. 2A and 2C). When added in combination with anti-HER2 antibody 1 or anti-HER2 antibody 2, Fc-C12 did not increase or decrease the activity of these two antibodies significantly (FIGS. 2A and 2C). However, when clone C12 was fused to the N-terminus of the light chain of the anti-HER2 antibody 1 (COVA208) or anti-HER2 antibody 2 (COVA210) to generate molecules with two different binding specificities for an antigen, it increased the antiproliferative effect of the unmodified corresponding antibodies (FIGS. 2B and 2D).

In summary, these results show that the molecules COVA208 and COVA210 are superior to the combination of the individual monospecific binding proteins.

Example 4

The Anti-Proliferative Activity of Anti-HER2 Fynomer-Antibody Fusions is Different Depending on the Relative Orientation of the Fynomer and the Binding Site of the Antibody Several different C12-antibody fusions were tested for their ability to inhibit growth of NCI-N87 tumor cells in order to investigate the influence of the fusion site where the Fyn SH3-derived sequence is attached to the antibody.

Methods:

COVA201 (SEQ ID NO:156; SEQ ID NO:155), COVA202 (SEQ ID NO:154; SEQ ID NO:157), COVA207 (SEQ ID NO:158; SEQ ID NO:155) and COVA208 (SEQ ID NO:154; SEQ ID NO:159) are all C12-anti-HER2 antibody 1 fusions in which the clone C12 is fused to either the C-terminus of the heavy chain (COVA201), C-terminus of the light chain (COVA202), N-terminus of the heavy chain (COVA207) and N-terminus of the light chain (COVA208). Expression and purification was performed as described for COVA208 in Example 3. The cell growth inhibition assay was performed on NCI-N87 cells as described in Example 3.

Results:

The different C12-anti-HER2 antibody 1 formats were found to exhibit different activities (FIGS. 3A and 3B). COVA208 was most efficacious at inhibiting tumor cell growth and reduced the relative viability to 37%. COVA207 and COVA201 showed intermediate activity (viability: 52% and 61%, respectively) while COVA202 was less active and reduced the viability to 67%, but was still better than anti-HER2 antibody 1 (81-82% viability).

These results show that fusions of one pair of a Fyn SH3-derived sequence and an antibody have different activities, depending on the site of fusion and that the N-terminal light chain fusion of C12 to anti-HER2 antibody 1 (=COVA208) showed the strongest anti-proliferative efficacy.

Example 5

COVA208 Inhibits the Growth of BT-474 Cells with Higher Efficacy than Anti-HER2 Antibody 1

Methods:

The tumor cell growth inhibition of COVA208 (SEQ ID NOs: 154 and 159) was compared to anti-HER2 antibody 1 (SEQ ID NO: 154 and 155) on the human breast tumor cell line BT-474 (purchased from ATCC). This HER2 overexpressing cell line is one of the best characterized models to study the activity of HER2 targeted agents. BT-474 cells were grown in DMEM/F12 medium (Gibco) supplemented with 10% heat-inactivated FBS (Gibco) and 10 µg/ml human recombinant insulin. The assay was performed as described in Example 3 for NCI-N87 cells.

Results:

COVA208 showed better antiproliferative activity than the anti-HER2 antibody 1 (FIG. 4).

Example 6

COVA208 Inhibits NCI-N87 Tumor Growth In Vivo More Efficiently than the Anti-HER2 Antibody 1

COVA208 was investigated in vivo for tumor growth inhibition and compared to anti-HER2 antibody 1.

Methods:

$5 \times 10^6$ human gastric tumor cells (ATCC; CRL-5822) were implanted s.c. into athymic CD-1 Nude mice (Charles River). Tumor dimensions and body weights were recorded three times weekly. The tumor volume was calculated according to the formula volume=(width)$^2$×length×π/6. When the average tumor size reached about 140 mm$^3$, which was 42 days after tumor inoculation, mice were randomized into three treatment groups comprising six mice each, and the treatment was initiated. COVA208 (SEQ ID NOs: 154 and 159) and anti-HER2 antibody 1 (SEQ ID NOs: 154 and 155) were administered i.p. once a week for four weeks (five injections in total). The first (loading) dose was 30 mg/kg, and each following (maintenance) dose was 15 mg/kg. Mice in the control group were injected with PBS.

Results:

Anti-HER2 antibody 1 treatment resulted in only weak tumor growth inhibition (FIG. 5). COVA208 showed improved tumor growth control for the duration of the treatment compared to anti-HER2 antibody 1. On day 32, the tumors in COVA208 treated mice were reduced in volume by 8% compared to the initial tumor size at the beginning of the treatment (d=0), whereas the anti-HER2 antibody 1-treated mice showed an increase in volume by 88%.

This result demonstrates that COVA208 shows significant superior efficacy in vivo compared to anti-HER2 antibody 1.

Example 7

COVA208 Exhibits an Antibody-Like PK Profile In Vivo

Methods:

The pharmacokinetic profile of COVA208 in C57BL/6 mice (Charles River) was investigated and compared to anti-HER2 antibody 1. Three C57BL/6 mice were injected i.v. with 200 µg COVA208 (SEQ ID NOs: 154 and 159) or anti-HER2 antibody 1 (SEQ ID NOs: 154 and 155). After 10 min, 6, 24, 48, 96, 120, 144 and 168 hours, blood was collected into EDTA coated microvettes (Sarstedt), centrifuged for 10 min at 9300 g and the serum levels of COVA208 or anti-HER2 antibody 1 were determined by ELISA. Black maxisorp microtiter plates (Nunc) were coated with 50 nM HER2 ECD (Bender MedSystems). After blocking with 4% milk (Rapilait, Migros, Switzerland) in PBS, 40 µl of PBS and 10 µl of serum at appropriate dilution were applied. After incubation for 1 hr, wells were washed with PBS, and bound COVA208 or anti-HER2 antibody 1 were detected with protein A-HRP conjugate (Sigma). The assay was developed with QuantaRed fluorogenic substrate (Pierce) and the fluorescence intensity was measured after 5 to 10 min at 544 nm (excitation) and 590 nm (emission). The serum levels of COVA208 and anti-HER2 antibody 1 were determined using a standard curve of COVA208 and anti-HER2 antibody 1 (diluted to 333-0.5 ng/ml each). From the concentrations of COVA208 and anti-HER2 antibody 1 determined in serum at different time points and the resulting slope k of the elimination phase (plotted in a semi-logarithmic scale), the half-lives were calculated using to the formula $t^{1/2}=\ln 2/-k$.

Results:

As shown in FIG. 6, the half-lives of COVA208 and the anti-HER2 antibody 1 as determined from the elimination phase (beta phase, time-points 24 h-168 h) were highly similar (247 and 187 h, respectively). These data demonstrate that COVA208 has drug-like in vivo PK properties.

Example 8

COVA208 is Stable and does not Aggregate

The integrity and stability of COVA208 was assessed by SDS-PAGE and by size exclusion chromatography.

Methods

Purified COVA208 (SEQ ID NOs: 154 and 159) and anti-HER2 antibody 1 (SEQ ID NOs: 154 and 155) were analyzed by SDS-PAGE. 4 µg protein were loaded either with reduced or with nonreduced disulphide bonds onto a 4-12% Bis/Tris Novex gel in 1×MOPS running buffer (Invitrogen), together with a molecular weight marker (RPN800e; GE healthcare). Protein bands were visualized by coomassie staining.

The size exclusion chromatography (SEC) profile of COVA208 was determined immediately after purification as well as after storage of the protein in PBS at 4° C. for one or two months. 100 µl COVA208 at a concentration of 1.75 mg/mL was loaded onto a Superdex 200 10/300 GL column in PBS (GE healthcare) at a flow rate of 0.5 ml/min, and the elution from the column was monitored by reading the OD$_{280}$.

Results:

The results of the SDS-PAGE and the SEC profiles of COVA208 are shown in FIG. 7. COVA208 runs in clearly defined bands at the expected molecular weight on an SDS-PAGE (top). Of particular interest is the finding that there is no native light chain detectable in COVA208 (MW around 30 kDa), indicating that there is no cleavage of the Fyn SH3-derived clone C12 from the antibody light chain.

COVA208 eluted in one main peak form the SEC column with a retention volume of 13.1 ml (bottom). Anti-HER2 antibody 1 eluted at 13.2 ml. Most importantly, no aggregates, which would elute at around 8 ml, were detectable in the COVA208 protein preparation.

The SEC profile of COVA208 did not change over two months of storage at 4° C. The elution peak remained narrow, symmetrical and appeared at the same retention volume. The protein preparation remained free of aggregates after 1 and 2 months of storage. This indicates that COVA208 remains stable over extended periods of storage at 4° C. In summary, these results support that COVA208 is a stable, monodisperse molecule with optimal biophysical properties.

Example 9

COVA208 has Superior Growth Inhibitory Activity as Compared to Anti-HER2 Antibody 1 on a Panel of Ten HER2-Expressing Tumor Cell Lines The anti-proliferative activity of COVA208 (SEQ ID NOs: 154 and 159) was compared to anti-HER2 antibody 1 (SEQ ID NOs: 154 and 155) on different HER2 positive cell lines. XTT assays were performed essentially as described in example 3. The cell lines used in this experiment and the experimental conditions are given in Table 1. Dose-response curves were fitted to the three parameter equation as described in example 3, and the maximal growth inhibition was calculated with the formula:

Maximum level of inhibition(%)=100%−bottom with the variable bottom derived from the nonlinear regression of the dose-response curves using the formula:

$$\% \text{ viability} = \text{bottom} + \frac{\text{top} - \text{bottom}}{1 + 10^{x - LogIC_{50}}}$$

The results of these assays are shown in FIG. 9. FIGS. 9A and 9B show dose-response curves obtained on the OE19 and on the Calu-3 cell lines, respectively. FIG. 9C represents the maximal growth inhibition obtained on each cell line with COVA208 and anti-HER2 antibody 1, including the results on NCI-N87 and BT-474 cell lines shown in FIGS. 2 and 4. COVA208 shows improved anti-proliferative activity as compared to anti-HER2 antibody 1 on all 10 cell lines.

Example 10

COVA208 Induces Apoptosis in NCI-N87 Gastric Cancer Cells

The ability of COVA208 to induce apoptosis was investigated on NCI-N87 cells by analyzing caspase 3/7 enzymatic activity and by detecting DNA fragmentation by TUNEL staining.

Methods

Caspase 3/7 assay: 45,000 NCI-N87 cells were seeded into the wells of a 96-well microtiter plate. One day later, 100 nM anti-HER2 antibody 1 (SEQ ID NOs: 154 and 155), COVA208 (SEQ ID NOs: 154 and 159) or PBS were added to the cells in triplicate. As positive control, 1 μM staurosporine was added. After two days incubation, the activity of caspase-3 and caspase-7 was determined using the fluorescence Apo-ONE® homogenous caspase-3/7 kit (Pierce).

The viability of the treated cultures was analyzed by XTT in parallel on replica plates, and the % viability relative to PBS treated samples was calculated as described in example 3. Caspase 3/7 activity was divided by % viability to obtain the normalized caspase 3/7 activity.

TUNEL assay: $0.8 \times 10^6$ NCI-N87 cells in 2 mL were distributed in 6-well plates. On the next day, 300 nM anti-HER2 antibody 1 (SEQ ID NOs: 154 and 155), COVA208 (SEQ ID NOs: 154 and 159) or PBS were added to the cells. As positive control, 1 μM staurosporine was added. After three days incubation, cells were detached, formalin-fixed, permeabilized in 70% ice-cold ethanol and the 3'-hydroxyl DNA ends labeled with fluorescein-deoxyuridine triphosphate (FITC-dUTP), using the APO-DIRECT kit (Phoenix flow systems). Labeled cells were analyzed by FACS, and the % TUNEL-positive cells determined by gating on the FITC-dUTP positive cell population.

Results

The results of the caspase 3/7 assay are shown in FIG. 10A. COVA208 resulted in increased caspase 3/7 activity, indicating that COVA208 induced apoptosis in NCI-N87 cells. Anti-HER2 antibody 1 did not result in induced caspase 3/7 activity.

The results of the TUNEL assay are shown in FIG. 10B. COVA208 induces DNA fragmentation in the majority of cells, further supporting that it is capable of inducing apoptosis, whereas anti-HER2 antibody 1 is not.

Example 11

COVA208 Inhibits Ligand-Dependent and Ligand-Independent HER2-Mediated Signalling Activation of HER2 downstream signaling leads to phosphorylation of HER3, resulting in the activation of the PI3K-Akt-mTOR pathway, or to the activation of the MAPK/Erk pathway. In tumor cell lines that display sufficiently high surface density of HER2, these downstream pathways are constitutively activated in the absence of HER3 ligands (ligand-independent signaling). In addition to ligand-independent activation of HER2 downstream signaling, the downstream pathways can also be activated by HER3 ligands which promote HER2-HER3 heterodimer formation (ligand-dependent signaling).

In order to investigate the effects of COVA208 on HER2 downstream signaling, HER2-overexpressing NCI-N87 cells were treated with COVA208 (SEQ ID NOs: 154 and 159), anti-HER2 antibody 1 (SEQ ID NOs: 154 and 155), anti-HER2 antibody 2 (SEQ ID NOs: 160 and 163), or PBS, and the cell lysates were analyzed for phospho-proteins by immunoblotting.

The assay was also performed on HER2 low-expressing MCF-7 cells, in which HER2 downstream phosphorylation is triggered only after addition of the HER3 ligand heregulin-1β.

Methods

NCI-N87 cells (ATCC; CRL-5822) were distributed in 6-well culture dishes in complete medium at $1 \times 10^6$ cells in 3 mL per well. After overnight incubation at 37° C./5% $CO_2$, 40 μg/mL anti-HER2 agents were added and the cells were incubated at 37° C./5% $CO_2$ for 72 h. Cells were subsequently lysed on ice in cell lysis buffer containing 1% Triton-X, protease inhibitor and phosphatase inhibitor cocktails (Roche Applied Sciences).

MCF-7 cells (ATCC; HTB-22) were cultured in MEM (Gibco)+10% FBS (Gibco). Cells were distributed in 6-well culture dishes at 0.5×10⁶ cells in 3 mL per well. After overnight incubation at 37° C./5% $CO_2$, cells were starved in medium without serum for 3 h. 40 µg/mL anti-HER2 agents were then added for 1 h during which the cells were kept at 37° C./5% $CO_2$. After 45 min, 2 nM human recombinant heregulin-1β (R&D systems) was added for 15 min. Cells were subsequently lysed on ice in cell lysis buffer containing 1% Triton-X, protease inhibitor and phosphatase inhibitor cocktails (Roche Applied Sciences).

Total cell lysates were cleared by centrifugation at 16,000×g for 10 min at 4° C. and the protein concentration in the cleared lysates was determined by Bradford assay (Bio-Rad). 10 µg of protein were separated on Novex® 4-12% Bis-Tris gels (Invitrogen) and transferred onto PVDF membrane.

Phospho-proteins were detected on PVDF membrane with antibodies against $pHER3^{Y1289}$ (Millipore), $pAkt^{S473}$ (CST) or $pErk1/2^{T202/Y204}$ (CST), followed by secondary HRP-conjugated antibodies (Jackson Immuno Research). Vinculin was detected with a vinculin-specific antibody (Millipore) and served as loading control. The immunoblots were developed with ECD prime chemiluminescent HRP substrate (GE healthcare) and exposed onto X-Ray film.

Results:

The results of this experiment are shown in FIG. 11. In MCF-7 cells, in which activation of HER2 downstream signaling requires HER3 ligands, COVA208 and anti-HER2 antibody 1 both block phosphorylation of HER3, Akt and Erk1/2 equally well, indicating that COVA208 retained the activity of its parental antibody. In contrast, anti-HER2 antibody 2 does not block ligand-induced phosphorylation of HER3, Akt or Erk1/2.

In NCI-N87 cells, where phosphorylation of HER2 downstream signaling proteins occurs independent of HER3 ligands, COVA208 efficiently blocks phosphorylation of HER3, Akt or Erk1/2, whereas anti-HER2 antibody 1 does not block phosphorylation. Anti-HER2 antibody 2 is also capable of efficiently blocking HER2 signaling under these conditions. These results indicate that COVA208 blocks ligand-dependent as well as ligand-independent HER2 downstream signalling events, in contrast to anti-HER2 antibodies 1 and 2, which block one but not the other.

Example 12

COVA208 is Internalized by NCI-N87 Cells

In order to investigate whether COVA208 promotes internalization of the HER2 receptor in vitro, NCI-N87 cells were cultured in the presence of COVA208 (SEQ ID NOs: 154 and 159) or with anti-HER2 antibody 1 (SEQ ID NOs: 154 and 155) followed by fixation and permeabilization of the cells and subsequent detection of the anti-HER2 agents by means of a fluorescent secondary antibody. Microscopic imaging was used to assess the sub-cellular distribution of the fluorescent signal.

Methods

NCI-N87 cells grown in Lab-Tek II $CC^2$ chamber slide wells were surface labelled on ice for 1 h with 100 nM COVA208 or anti-HER2 antibody 1. Unbound anti-HER2 agent was then washed off. As positive control, 1 µM geldanamycin (Hsp90 inhibitor) which causes rapid internalization of HER2 was added to some wells. The cells were transferred to 37° C./5% $CO_2$ for 0 h or 5 h to allow for internalization, then fixed with formalin and permeabilized with saponin. An Alexa488-labeled anti-human IgG antibody (Invitrogen) was used to detect anti-HER2 agents on permeabilized cells, and nuclei were stained with Hoechst 33342 dye. The stained cells were analyzed on a Leica TCS SP2-AOBS laser scanning confocal microscope. Optical sections (z-stacks, d=0.2 µm) were collected and three regions were analyzed. The amount of anti-HER2 agents which localized into distinct dots was quantified with the software Imaris 7.4.0 (Bitplane), using the surface tool of Imaris to detected spheroid dots, and expressing the percentage of anti-HER2 agents present in dots:

% anti-HER2 agents in dots=(volume of dots/volume of total anti-HER2 staining)×100

Results

After surface labelling and before incubation at 37° C., COVA208 and anti-HER2 antibody 1 localized to the cell membrane. After 5 hours incubation at 37° C., COVA208 was present in distinct dots within the cytosol, while the cell membrane was only very weakly stained. In contrast, the anti-HER2 antibody 1 was confined to the cell membrane after 5 h incubation at 37° C., and only very few dots in the cytosol were detected. If co-incubated with geldanamycin, anti-HER2 antibody 1 was also found in dots and the cell membrane was negative for the antibody. These results indicate that unlike anti-HER2 antibody 1, COVA208 rapidly internalizes into NCI-N87 cells.

The quantification of the % staining appearing within dots is shown in FIG. 12. The majority of COVA208 localizes into dots, whereas only a small fraction of anti-HER2 antibody 1 is found in dots.

Example 13

COVA208 Inhibits KPL-4 Breast Tumor Growth In Vivo More Efficiently than the Anti-HER2 Antibody 1

COVA208 was investigated in vivo in KPL-4 breast tumors for growth inhibition and compared to anti-HER2 antibody 1.

Methods:

3×10⁶ human KPL-4 breast tumor cells (Kurebayashi et al. (1999) Br. J. Cancer. 79; 707-717) were implanted into the mammary fat pad of female SCID beige mice (Charles River). Tumor dimensions and body weights were recorded three times weekly. The tumor volume was calculated according to the formula volume=(width)²×length×π/6. When the average tumor size reached 70 mm³, mice were randomized into three treatment groups comprising eight mice each, and the treatment was initiated. COVA208 (SEQ ID NOs: 154 and 159), anti-HER2 antibody 1 (SEQ ID NOs: 154 and 155) or PBS were administered i.p. once a week for four weeks (five injections in total). The first (loading) dose was 30 mg/kg, and each following (maintenance) dose was 15 mg/kg.

Results:

Anti-HER2 antibody 1 treatment resulted in very weak tumor growth inhibition only (FIG. 13). COVA208 showed significantly improved tumor growth control. This result further supports that COVA208 shows significantly superior efficacy in vivo compared to anti-HER2 antibody 1.

Example 14

Determination of the HER2 Epitope Bound by the Fyn SH3-Derived Polypeptide C12

The epitope bound by the Fyn SH3-derived clone C12 (SEQ ID NO: 1) on HER2 was identified by an alanine scanning mutation approach and was performed at Integral Molecular Inc. (Philadelphia, USA). A shotgun mutagenesis mutation library was created as described in Paes et al (2009) J Am Chem Soc 131(20): 6952-6954. Briefly, a eukaryotic expression plasmid encoding full-length human HER2 was constructed with a C-terminal V5His epitope tag. Using the parental cDNA construct as a template, alanine scanning mutations were introduced into the extracellular domain of HER2 (amino acids 23-652 of SEQ ID NO: 171) using PCR-based mutagenesis. Residues which were already alanine in the parental construct were mutated to methionine. Mutated constructs and the parental HER2 control construct were expressed in HEK-293T cells. Twenty-four hours post-transfection, cells were washed in PBS and fixed in 4% paraformaldehyde. Cells were incubated with control anti-HER2 monoclonal antibody (MAB1129, R&D Systems) or with Fyn SH3-derived clone C12 (expressed as N-terminal Fc fusion) in PBS with $Ca^{2+}/Mg^{2+}$ (PBS++) and 10% Normal Goat Serum (NGS) for 1 hour. After two washes in PBS, cells were incubated with goat anti-human Alexa Fluor 488-conjugated secondary antibodies (Jackson, West Grove, Pa.) in PBS++ and NGS for 1 hour, followed by 2 washes in PBS. Microplates were measured by flow cytometry using the Intellicyt HTFC Screening System and quantified using Forecyt software (Intellicyt Corporation, Albuquerque, N. Mex.).

It has been found that the Fyn SH3-derived polypeptide C12 (SEQ ID NO: 1) binds to an epitope of HER2 which is located within domain I of HER2 (SEQ ID NO: 172). In more detail, five alanine scanning mutations were identified which resulted in markedly reduced binding of the binding molecules comprising the Fyn SH3-derived polypeptide C12 (SEQ ID NO: 1) while binding of the control antibody MAB1129 was retained. These mutations included T166A, R188A, P197A, S202A and R203A as compared to the sequence of SEQ ID NO: 172. In other terms, at least amino acid positions T166, R188, P197, S202 and R203 of domain I of HER2 are involved in binding between the Fyn SH3-derived polypeptide C12 and HER2.

TABLE 1

HER2 expressing cell lines used in in vitro proliferation assays described in FIG. 9 and the conditions applied in the in vitro proliferation assays.

| Cell line | Description | Distributor | growth medium | XTT assay conditions | |
|---|---|---|---|---|---|
| | | | | cells/well seeded | incuation time with anti-HER2 agents |
| NCI-N87 | gastric carcinoma, liver metastasis | ATCC | RPMI1640 + 10% FBS | 7000 | 5 days |
| BT-474 | breast, ductal carcinoma | ATCC | DMEM/F12 + insulin + 10% FBS | 7000 | 5 days |
| KPL-4 | breast, malignant pleural effusion | Prof. Kurebayashi* | DMEM + 10% FBS | 2000 | 3 days |
| OE19 | gastric (oesophagal carcinoma) | hpa cultures | RPMI1640 + 10% FBS | 5000 | 5 days |
| Calu-3 | pleural effusion of lung adenocarcinoma | ATCC | MEM + 10% FBS | 5000 | 5 days |
| SKOV-3 | ovarian adenocarcinoma, ascites | ATCC | modified McCoy5a + 10% FBS | 2000 | 3 days |
| MDA-MB-453 | pericardial effusion of metastatic breast carc. | ATCC | DMEM + 10% FBS | 2000 | 5 days |
| HCC202 | primary ductal carcinoma | ATCC | RPMI1640 + 10% FBS | 5000 | 5 days |
| ZR-75-30 | breast, ductal carcinoma, malignant ascites | ATCC | RPMI1640 + 10% FBS | 5000 | 5 days |
| MDA-MB-175-VII | pleural effusion of ductal carcinoma | ATCC | DMEM + 10% FBS | 5000 | 5 days |

*Kurebayashi et al. (1999) Br. J. Cancer. 79; 707-717

The invention claimed is:

1. A fusion protein comprising two polypeptides:
   (a) a first polypeptide comprising the amino acid sequence of SEQ ID NO: 1 or an amino acid sequence at least 90% identical to the amino acid sequence of SEQ ID NO: 1, and
   (b) a second polypeptide that is an antibody comprising a heavy chain comprising or consisting of the amino acid sequence of SEQ ID NO: 154 or an amino acid sequence at least 95% identical thereto, and a light chain comprising or consisting of the amino acid sequence of SEQ ID NO: 155 or an amino acid sequence at least 95% identical thereto.

2. The fusion protein of claim 1, wherein the first and the second polypeptides are linked by a linker.

3. The fusion protein of claim 2, wherein the linker is a peptide-linker.

4. The fusion protein of claim 3, wherein the linker is $(Gly_4Ser)_3$.

5. The fusion protein of claim 1, wherein
   (a) the first polypeptide consists of the amino acid sequence of SEQ ID NO: 1, and
   (b) the antibody constituting the second polypeptide comprises the heavy chain consisting of the amino acid sequence of SEQ ID NO: 154 and the light chain consisting of the amino acid sequence of SEQ ID NO: 155.

6. The fusion protein of claim 5, wherein the C-terminal end of the amino acid sequence of SEQ ID NO: 1 is linked to the N-terminal end of the amino acid sequence of SEQ ID NO: 155.

7. The fusion protein of claim 6, wherein the C-terminal end of the amino acid sequence of SEQ ID NO: 1 is linked to the N-terminal end of the amino acid sequence of SEQ ID NO: 155 via a $(Gly_4Ser)_3$ linker.

8. The fusion protein of claim 1, wherein said fusion protein further comprises at least one additional polypeptide.

9. The fusion protein of claim 1, wherein the CDR domains of the heavy chain comprise amino acids 31 to 35 of the amino acid sequence of SEQ ID NO: 154 for CDR1, amino acids 50 to 66 of the amino acid sequence of SEQ ID NO: 154 for CDR2, and amino acids 99 to 108 of the amino acid sequence of SEQ ID NO: 154 for CDR3.

10. The fusion protein of claim 1, wherein the CDR domains of the light chain comprise amino acids 24 to 34 of the amino acid sequence of SEQ ID NO: 155 for CDR1, amino acids 50 to 56 of the amino acid sequence of SEQ ID NO: 155 for CDR2, and 89 to 97 of the amino acid sequence of SEQ ID NO: 155 for CDR3.

* * * * *

SEQUENCE LISTING

```
<160> NUMBER OF SEQ ID NOS: 177

<210> SEQ ID NO 1
<211> LENGTH: 63
<212> TYPE: PRT
<213> ORGANISM: Artificial sequence
<220> FEATURE:
<223> OTHER INFORMATION: Fynomer #1 C12

<400> SEQUENCE: 1

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45
```

```
Gly Tyr Ile Pro Ser Asn Tyr Val Ala Pro Val Asp Ser Ile Gln
        50                  55                  60
```

<210> SEQ ID NO 2
<211> LENGTH: 67
<212> TYPE: PRT
<213> ORGANISM: Artificial sequence
<220> FEATURE:
<223> OTHER INFORMATION: Fynomer #1 G10

<400> SEQUENCE: 2

```
Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
                20                  25                  30

Leu Lys Arg Trp Arg Gly Asp Trp Trp Glu Ala Arg Ser Leu Thr
            35                  40                  45

Thr Gly Glu Thr Gly Tyr Ile Pro Ser Asn Tyr Val Ala Pro Val Asp
        50                  55                  60

Ser Ile Gln
65
```

<210> SEQ ID NO 3
<211> LENGTH: 67
<212> TYPE: PRT
<213> ORGANISM: Artificial sequence
<220> FEATURE:
<223> OTHER INFORMATION: Fynomer #3

<400> SEQUENCE: 3

```
Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
                20                  25                  30

Leu Thr Arg Trp Ala Gln Gly Asp Trp Trp Glu Ala Arg Ser Leu Thr
            35                  40                  45

Thr Gly Glu Thr Gly Tyr Ile Pro Ser Asn Tyr Val Ala Pro Val Asp
        50                  55                  60

Ser Ile Gln
65
```

<210> SEQ ID NO 4
<211> LENGTH: 64
<212> TYPE: PRT
<213> ORGANISM: Artificial sequence
<220> FEATURE:
<223> OTHER INFORMATION: Fynomer #4

<400> SEQUENCE: 4

```
Gly Val Thr Leu Phe Val Ala Leu Tyr Asp Tyr Gln Ala Tyr Gly Met
1               5                   10                  15

Tyr Asp Leu Ser Phe His Lys Gly Glu Lys Phe Gln Ile Leu Ser Pro
                20                  25                  30

Lys Asp Thr Gly Tyr Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60
```

<210> SEQ ID NO 5
<211> LENGTH: 66

<212> TYPE: PRT
<213> ORGANISM: Artificial sequence
<220> FEATURE:
<223> OTHER INFORMATION: Fynomer #5

<400> SEQUENCE: 5

Gly Val Thr Leu Phe Val Ala Leu Tyr Asp Tyr Glu Ala Arg Glu Phe
1               5                   10                  15

Met Gly Gly Gln Asp Leu Ser Phe His Lys Gly Glu Lys Phe Gln Ile
            20                  25                  30

Leu Thr Met Trp Lys Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65

<210> SEQ ID NO 6
<211> LENGTH: 67
<212> TYPE: PRT
<213> ORGANISM: Artificial sequence
<220> FEATURE:
<223> OTHER INFORMATION: Fynomer #6

<400> SEQUENCE: 6

Gly Val Thr Leu Phe Val Ala Leu Tyr Asp Tyr Glu Ala Arg Pro Tyr
1               5                   10                  15

Leu Gly Gly Gln Asp Leu Ser Phe His Lys Gly Glu Lys Phe Gln Ile
            20                  25                  30

Leu His Ala Ser Met Leu Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65

<210> SEQ ID NO 7
<211> LENGTH: 63
<212> TYPE: PRT
<213> ORGANISM: Artificial sequence
<220> FEATURE:
<223> OTHER INFORMATION: Fynomer #7

<400> SEQUENCE: 7

Gly Val Thr Leu Phe Val Ala Leu Tyr Asp Tyr Thr Ser Tyr Asn Gln
1               5                   10                  15

His Asp Leu Ser Phe His Lys Gly Glu Lys Phe Gln Ile Leu Gly Asp
            20                  25                  30

Asn Ile Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 8
<211> LENGTH: 67
<212> TYPE: PRT
<213> ORGANISM: Artificial sequence
<220> FEATURE:
<223> OTHER INFORMATION: Fynomer #8

<400> SEQUENCE: 8

```
Gly Val Thr Leu Phe Val Ala Leu Tyr Asp Tyr Glu Ala Arg Leu Ser
1               5                   10                  15

Ser His Pro His Val Leu Ser Phe His Lys Gly Glu Lys Phe Gln Ile
                20                  25                  30

Leu Asn Arg Val Ser Ile Gly Asp Trp Trp Glu Ala Arg Ser Leu Thr
            35                  40                  45

Thr Gly Glu Thr Gly Tyr Ile Pro Ser Asn Tyr Val Ala Pro Val Asp
        50                  55                  60

Ser Ile Gln
65

<210> SEQ ID NO 9
<211> LENGTH: 67
<212> TYPE: PRT
<213> ORGANISM: Artificial sequence
<220> FEATURE:
<223> OTHER INFORMATION: Fynomer #9

<400> SEQUENCE: 9

Gly Val Thr Leu Phe Val Ala Leu Tyr Asp Tyr Glu Ala Arg Pro Tyr
1               5                   10                  15

Leu Gly Gly Gln Asp Leu Ser Phe His Lys Gly Glu Lys Phe Gln Ile
                20                  25                  30

Leu Asn His Pro Pro Thr Gly Asp Trp Trp Glu Ala Arg Ser Leu Thr
            35                  40                  45

Thr Gly Glu Thr Gly Tyr Ile Pro Ser Asn Tyr Val Ala Pro Val Asp
        50                  55                  60

Ser Ile Gln
65

<210> SEQ ID NO 10
<211> LENGTH: 65
<212> TYPE: PRT
<213> ORGANISM: Artificial sequence
<220> FEATURE:
<223> OTHER INFORMATION: Fynomer #10

<400> SEQUENCE: 10

Gly Val Thr Leu Phe Val Ala Leu Tyr Asp Tyr Glu Ala Tyr Asp Leu
1               5                   10                  15

Ser Arg Pro Asp Leu Ser Phe His Lys Gly Glu Lys Phe Gln Ile Leu
                20                  25                  30

Asn Ser Ser Glu Gly Thr Trp Trp Glu Ala Arg Ser Leu Thr Thr Gly
            35                  40                  45

Glu Thr Gly Phe Ile Pro Ser Asn Tyr Val Ala Pro Val Asp Ser Ile
        50                  55                  60

Gln
65

<210> SEQ ID NO 11
<211> LENGTH: 67
<212> TYPE: PRT
<213> ORGANISM: Artificial sequence
<220> FEATURE:
<223> OTHER INFORMATION: Fynomer #11

<400> SEQUENCE: 11

Gly Val Thr Leu Phe Val Ala Leu Tyr Asp Tyr Glu Ala Arg Met Pro
1               5                   10                  15

Lys Val Ser Asp Leu Ser Phe His Lys Gly Glu Lys Phe Gln Ile Leu
```

```
                    20                  25                  30

Gln Glu Pro Gln Ser Lys Gly Asp Trp Trp Glu Ala Arg Ser Leu Thr
                35                  40                  45

Thr Gly Glu Thr Gly Tyr Ile Pro Ser Asn Tyr Val Ala Pro Val Asp
    50                  55                  60

Ser Ile Gln
65

<210> SEQ ID NO 12
<211> LENGTH: 67
<212> TYPE: PRT
<213> ORGANISM: Artificial sequence
<220> FEATURE:
<223> OTHER INFORMATION: Fynomer #12

<400> SEQUENCE: 12

Gly Val Thr Leu Phe Val Ala Leu Tyr Asp Tyr Glu Ala Arg Pro Gly
1               5                   10                  15

Arg His Ser Ser Asp Leu Ser Phe His Lys Gly Glu Lys Phe Gln Ile
                20                  25                  30

Leu His Gln Ser Asn Val Gly Asp Trp Trp Glu Ala Arg Ser Leu Thr
                35                  40                  45

Thr Gly Glu Thr Gly Tyr Ile Pro Ser Asn Tyr Val Ala Pro Val Asp
    50                  55                  60

Ser Ile Gln
65

<210> SEQ ID NO 13
<211> LENGTH: 64
<212> TYPE: PRT
<213> ORGANISM: Artificial sequence
<220> FEATURE:
<223> OTHER INFORMATION: Fynomer #13

<400> SEQUENCE: 13

Gly Val Thr Leu Phe Val Ala Leu Tyr Asp Tyr Gln Thr Thr Arg Pro
1               5                   10                  15

His Asp Leu Ser Phe His Lys Gly Glu Lys Phe Gln Ile Leu Gly Arg
                20                  25                  30

Thr Gln Ile Gly Asp Trp Trp Glu Ala Arg Ser Leu Thr Thr Gly Glu
                35                  40                  45

Thr Gly Tyr Ile Pro Ser Asn Tyr Val Ala Pro Val Asp Ser Ile Gln
    50                  55                  60

<210> SEQ ID NO 14
<211> LENGTH: 63
<212> TYPE: PRT
<213> ORGANISM: Artificial sequence
<220> FEATURE:
<223> OTHER INFORMATION: Fynomer #14

<400> SEQUENCE: 14

Gly Val Thr Leu Phe Val Ala Leu Tyr Asp Tyr Gln Thr Asn Asn Ser
1               5                   10                  15

Arg Asp Leu Ser Phe His Lys Gly Glu Lys Phe Gln Ile Leu Gly Asn
                20                  25                  30

Thr Gln Gly Asp Trp Trp Glu Ala Arg Ser Leu Thr Thr Gly Glu Thr
                35                  40                  45

Gly Tyr Ile Pro Ser Asn Tyr Val Ala Pro Val Asp Ser Ile Gln
    50                  55                  60
```

```
<210> SEQ ID NO 15
<211> LENGTH: 63
<212> TYPE: PRT
<213> ORGANISM: Artificial sequence
<220> FEATURE:
<223> OTHER INFORMATION: Fynomer #15

<400> SEQUENCE: 15

Gly Val Thr Leu Phe Val Ala Leu Tyr Asp Tyr Tyr Ser Tyr Asn Thr
1               5                   10                  15

His Asp Leu Ser Phe His Lys Gly Glu Lys Phe Gln Ile Leu Ser Arg
            20                  25                  30

Ala Asn Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 16
<211> LENGTH: 63
<212> TYPE: PRT
<213> ORGANISM: Artificial sequence
<220> FEATURE:
<223> OTHER INFORMATION: Fynomer #16

<400> SEQUENCE: 16

Gly Val Thr Leu Phe Val Ala Leu Tyr Asp Tyr Tyr Ser Tyr Asn Asn
1               5                   10                  15

His Asp Leu Ser Phe His Lys Gly Glu Lys Phe Gln Ile Leu Gln Glu
            20                  25                  30

Leu Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 17
<211> LENGTH: 63
<212> TYPE: PRT
<213> ORGANISM: Artificial sequence
<220> FEATURE:
<223> OTHER INFORMATION: Fynomer #17

<400> SEQUENCE: 17

Gly Val Thr Leu Phe Val Ala Leu Tyr Asp Tyr Arg Ser Tyr Asn Thr
1               5                   10                  15

Arg Asp Leu Ser Phe His Lys Gly Glu Lys Phe Gln Ile Leu Thr Lys
            20                  25                  30

Ser Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 18
<211> LENGTH: 65
<212> TYPE: PRT
<213> ORGANISM: Artificial sequence
<220> FEATURE:
<223> OTHER INFORMATION: Fynomer #18

<400> SEQUENCE: 18

Gly Val Thr Leu Phe Val Ala Leu Tyr Asp Tyr Thr Ser Tyr Asn Thr
1               5                   10                  15
```

```
Arg Asp Leu Ser Phe His Lys Gly Glu Lys Phe Gln Ile Leu Lys Ala
            20                  25                  30

His Ser Leu Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
50                  55                  60

Gln
65

<210> SEQ ID NO 19
<211> LENGTH: 65
<212> TYPE: PRT
<213> ORGANISM: Artificial sequence
<220> FEATURE:
<223> OTHER INFORMATION: Fynomer #19

<400> SEQUENCE: 19

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Glu
            20                  25                  30

Gln Asp Leu Arg Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
50                  55                  60

Gln
65

<210> SEQ ID NO 20
<211> LENGTH: 63
<212> TYPE: PRT
<213> ORGANISM: Artificial sequence
<220> FEATURE:
<223> OTHER INFORMATION: Fynomer #20

<400> SEQUENCE: 20

Gly Val Thr Leu Phe Val Ala Leu Tyr Asp Tyr Thr Ser Tyr Asn Lys
1               5                   10                  15

Leu Asp Leu Ser Phe His Lys Gly Glu Lys Phe Gln Ile Leu Arg Thr
            20                  25                  30

Asp Ala Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
50                  55                  60

<210> SEQ ID NO 21
<211> LENGTH: 63
<212> TYPE: PRT
<213> ORGANISM: Artificial sequence
<220> FEATURE:
<223> OTHER INFORMATION: Fynomer #21

<400> SEQUENCE: 21

Gly Val Thr Leu Phe Val Ala Leu Tyr Asp Tyr Thr Ser Tyr Asn Gln
1               5                   10                  15

Arg Asp Leu Ser Phe His Lys Gly Glu Lys Phe Gln Ile Leu Gly Pro
            20                  25                  30

Lys Leu Gly Asp Trp Trp Glu Ala Arg Ser Leu Thr Thr Gly Glu Thr
        35                  40                  45
```

```
<210> SEQ ID NO 22
<211> LENGTH: 63
<212> TYPE: PRT
<213> ORGANISM: Artificial sequence
<220> FEATURE:
<223> OTHER INFORMATION: Fynomer #22

<400> SEQUENCE: 22

Gly Val Thr Leu Phe Val Ala Leu Tyr Asp Tyr Thr Ser Tyr Asn Asn
1               5                   10                  15

His Asp Leu Ser Phe His Lys Gly Glu Lys Phe Gln Ile Leu Asn Gln
            20                  25                  30

His Asn Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 23
<211> LENGTH: 63
<212> TYPE: PRT
<213> ORGANISM: Artificial sequence
<220> FEATURE:
<223> OTHER INFORMATION: Fynomer #23

<400> SEQUENCE: 23

Gly Val Thr Leu Phe Val Ala Leu Tyr Asp Tyr Thr Ser Tyr Asn Leu
1               5                   10                  15

Arg Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 24
<211> LENGTH: 65
<212> TYPE: PRT
<213> ORGANISM: Artificial sequence
<220> FEATURE:
<223> OTHER INFORMATION: Fynomer #24

<400> SEQUENCE: 24

Gly Val Thr Leu Phe Val Ala Leu Tyr Asp Tyr Thr Ser Tyr Asn Pro
1               5                   10                  15

Arg Asp Leu Ser Phe His Lys Gly Glu Lys Phe Gln Ile Leu Gly Ala
            20                  25                  30

Thr Asp Ala Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 25
<211> LENGTH: 63
<212> TYPE: PRT
<213> ORGANISM: Artificial sequence
<220> FEATURE:
<223> OTHER INFORMATION: Fynomer #25
```

<400> SEQUENCE: 25

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Asn Glu
            20                  25                  30

Leu Asn Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 26
<211> LENGTH: 63
<212> TYPE: PRT
<213> ORGANISM: Artificial sequence
<220> FEATURE:
<223> OTHER INFORMATION: Fynomer #26

<400> SEQUENCE: 26

Gly Val Thr Leu Phe Val Ala Leu Tyr Asp Tyr Thr Ser Tyr Asn Ser
1               5                   10                  15

Ser Asp Leu Ser Phe His Lys Gly Glu Lys Phe Gln Ile Leu Arg Glu
            20                  25                  30

Ala Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 27
<211> LENGTH: 67
<212> TYPE: PRT
<213> ORGANISM: Artificial sequence
<220> FEATURE:
<223> OTHER INFORMATION: Fynomer #27

<400> SEQUENCE: 27

Gly Val Thr Leu Phe Val Ala Leu Tyr Asp Tyr Glu Ala Arg Arg Asp
1               5                   10                  15

His Ser Pro His Asp Leu Ser Phe His Lys Gly Glu Lys Phe Gln Ile
            20                  25                  30

Leu Asn Leu Tyr Gln Val Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65

<210> SEQ ID NO 28
<211> LENGTH: 66
<212> TYPE: PRT
<213> ORGANISM: Artificial sequence
<220> FEATURE:
<223> OTHER INFORMATION: Fynomer #28

<400> SEQUENCE: 28

Gly Val Thr Leu Phe Val Ala Leu Tyr Asp Tyr Glu Ala Arg Glu Ala
1               5                   10                  15

Leu Gly Gly Gln Asp Leu Ser Phe His Lys Gly Glu Lys Phe Gln Ile
            20                  25                  30

Leu Ser Pro Gln Thr Gly Asp Trp Trp Glu Ala Arg Ser Leu Thr Thr

```
                    35                  40                  45

Gly Glu Thr Gly Tyr Ile Pro Ser Asn Tyr Val Ala Pro Val Asp Ser
    50                  55                  60

Ile Gln
65

<210> SEQ ID NO 29
<211> LENGTH: 64
<212> TYPE: PRT
<213> ORGANISM: Artificial sequence
<220> FEATURE:
<223> OTHER INFORMATION: Fynomer #29

<400> SEQUENCE: 29

Gly Val Thr Leu Phe Val Ala Leu Tyr Asp Tyr Tyr Ser Val His Pro
1               5                   10                  15

Gly Asp Leu Ser Phe His Lys Gly Glu Lys Phe Gln Ile Leu Ser Asn
                20                  25                  30

Tyr Gln Val Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
    50                  55                  60

<210> SEQ ID NO 30
<211> LENGTH: 63
<212> TYPE: PRT
<213> ORGANISM: Artificial sequence
<220> FEATURE:
<223> OTHER INFORMATION: Fynomer #30

<400> SEQUENCE: 30

Gly Val Thr Leu Phe Val Ala Leu Tyr Asp Tyr Ser Tyr Asn Ser
1               5                   10                  15

Arg Asp Leu Ser Phe His Lys Gly Glu Lys Phe Gln Ile Leu Ala Gln
                20                  25                  30

His Asp Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60

<210> SEQ ID NO 31
<211> LENGTH: 63
<212> TYPE: PRT
<213> ORGANISM: Artificial sequence
<220> FEATURE:
<223> OTHER INFORMATION: Fynomer #31

<400> SEQUENCE: 31

Gly Val Thr Leu Phe Val Ala Leu Tyr Asp Tyr Thr Ser Tyr Asn Met
1               5                   10                  15

Arg Asp Leu Ser Phe His Lys Gly Glu Lys Phe Gln Ile Leu Gly Arg
                20                  25                  30

Gly Pro Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60

<210> SEQ ID NO 32
<211> LENGTH: 65
<212> TYPE: PRT
<213> ORGANISM: Artificial sequence
```

-continued

<220> FEATURE:
<223> OTHER INFORMATION: Fynomer #32

<400> SEQUENCE: 32

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gly Arg
            20                  25                  30

Pro Arg Asp Val Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 33
<211> LENGTH: 63
<212> TYPE: PRT
<213> ORGANISM: Artificial sequence
<220> FEATURE:
<223> OTHER INFORMATION: Fynomer #33

<400> SEQUENCE: 33

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu His Thr
            20                  25                  30

Thr Lys Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 34
<211> LENGTH: 65
<212> TYPE: PRT
<213> ORGANISM: Artificial sequence
<220> FEATURE:
<223> OTHER INFORMATION: Fynomer #34

<400> SEQUENCE: 34

Gly Val Thr Leu Phe Val Ala Leu Tyr Asp Tyr Thr Ser Tyr Asn Thr
1               5                   10                  15

Thr Asp Leu Ser Phe His Lys Gly Glu Lys Phe Gln Ile Leu His Trp
            20                  25                  30

Asn Gly Gly Ser Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 35
<211> LENGTH: 63
<212> TYPE: PRT
<213> ORGANISM: Artificial sequence
<220> FEATURE:
<223> OTHER INFORMATION: Fynomer #35

<400> SEQUENCE: 35

Gly Val Thr Leu Phe Val Ala Leu Tyr Asp Tyr Thr Ser Tyr Asn Thr
1               5                   10                  15

```
Thr Asp Leu Ser Phe His Lys Gly Glu Lys Phe Gln Ile Leu Asn Asn
            20                  25                  30

Thr Thr Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
 50                  55                  60
```

<210> SEQ ID NO 36
<211> LENGTH: 65
<212> TYPE: PRT
<213> ORGANISM: Artificial sequence
<220> FEATURE:
<223> OTHER INFORMATION: Fynomer #36

<400> SEQUENCE: 36

```
Gly Val Thr Leu Phe Val Ala Leu Tyr Asp Tyr Trp Ser Tyr Asn Ser
1               5                   10                  15

Arg Asp Leu Ser Phe His Lys Gly Glu Lys Phe Gln Ile Leu Asn Pro
            20                  25                  30

Glu Glu Thr Ser Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
 50                  55                  60

Gln
65
```

<210> SEQ ID NO 37
<211> LENGTH: 65
<212> TYPE: PRT
<213> ORGANISM: Artificial sequence
<220> FEATURE:
<223> OTHER INFORMATION: Fynomer #37

<400> SEQUENCE: 37

```
Gly Val Thr Leu Phe Val Ala Leu Tyr Asp Tyr Thr Ser Tyr Asn Pro
1               5                   10                  15

Arg Asp Leu Ser Phe His Lys Gly Glu Lys Phe Gln Ile Leu Asn Pro
            20                  25                  30

Arg Gln Arg Ile Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
 50                  55                  60

Gln
65
```

<210> SEQ ID NO 38
<211> LENGTH: 63
<212> TYPE: PRT
<213> ORGANISM: Artificial sequence
<220> FEATURE:
<223> OTHER INFORMATION: Fynomer #38

<400> SEQUENCE: 38

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Asn Arg
            20                  25                  30

Pro Met Gly Asp Trp Trp Glu Ala Arg Ser Leu Thr Thr Gly Glu Thr
        35                  40                  45
```

```
Gly Tyr Ile Pro Ser Asn Tyr Val Ala Pro Val Asp Ser Ile Gln
    50                  55                  60

<210> SEQ ID NO 39
<211> LENGTH: 65
<212> TYPE: PRT
<213> ORGANISM: Artificial sequence
<220> FEATURE:
<223> OTHER INFORMATION: Fynomer #39

<400> SEQUENCE: 39

Gly Val Thr Leu Phe Val Ala Leu Tyr Asp Tyr Thr Ser Tyr Asn Gln
1               5                   10                  15

His Asp Leu Ser Phe His Lys Gly Glu Lys Phe Gln Ile Leu Pro Thr
            20                  25                  30

Thr Asp Thr Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 40
<211> LENGTH: 63
<212> TYPE: PRT
<213> ORGANISM: Artificial sequence
<220> FEATURE:
<223> OTHER INFORMATION: Fynomer #40

<400> SEQUENCE: 40

Gly Val Thr Leu Phe Val Ala Leu Tyr Asp Tyr Thr Ser Tyr Asn Thr
1               5                   10                  15

Met Asp Leu Ser Phe His Lys Gly Glu Lys Phe Gln Ile Leu Arg Glu
            20                  25                  30

Thr Thr Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 41
<211> LENGTH: 63
<212> TYPE: PRT
<213> ORGANISM: Artificial sequence
<220> FEATURE:
<223> OTHER INFORMATION: Fynomer #41

<400> SEQUENCE: 41

Gly Val Thr Leu Phe Val Ala Leu Tyr Asp Tyr Thr Ser Tyr Asn Thr
1               5                   10                  15

His Asp Leu Ser Phe His Lys Gly Glu Lys Phe Gln Ile Leu Arg Gln
            20                  25                  30

Asn Asn Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 42
<211> LENGTH: 63
<212> TYPE: PRT
<213> ORGANISM: Artificial sequence
<220> FEATURE:
<223> OTHER INFORMATION: Fynomer #42
```

```
<400> SEQUENCE: 42

Gly Val Thr Leu Phe Val Ala Leu Tyr Asp Tyr Thr Ser Tyr Asn Ser
1               5                   10                  15

Thr Asp Leu Ser Phe His Lys Gly Glu Lys Phe Gln Ile Leu Ser Ala
            20                  25                  30

Pro Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 43
<211> LENGTH: 63
<212> TYPE: PRT
<213> ORGANISM: Artificial sequence
<220> FEATURE:
<223> OTHER INFORMATION: Fynomer #43

<400> SEQUENCE: 43

Gly Val Thr Leu Phe Val Ala Leu Tyr Asp Tyr Thr Ser Tyr Asn Ala
1               5                   10                  15

Arg Asp Leu Ser Phe His Lys Gly Glu Lys Phe Gln Ile Leu Ser Ala
            20                  25                  30

Pro Thr Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 44
<211> LENGTH: 65
<212> TYPE: PRT
<213> ORGANISM: Artificial sequence
<220> FEATURE:
<223> OTHER INFORMATION: Fynomer #44

<400> SEQUENCE: 44

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Asp
            20                  25                  30

Ala Thr Leu Glu Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 45
<211> LENGTH: 65
<212> TYPE: PRT
<213> ORGANISM: Artificial sequence
<220> FEATURE:
<223> OTHER INFORMATION: Fynomer #45

<400> SEQUENCE: 45

Gly Val Thr Leu Phe Val Ala Leu Tyr Asp Tyr Thr Ser Tyr Asn Lys
1               5                   10                  15

Arg Asp Leu Ser Phe His Lys Gly Glu Lys Phe Gln Ile Leu Ser Glu
            20                  25                  30

Thr Ser Pro Glu Gly Asp Trp Trp Glu Ala Arg Ser Leu Thr Thr Gly
```

```
                       35                  40                  45

Glu Thr Gly Tyr Ile Pro Ser Asn Tyr Val Ala Pro Val Asp Ser Ile
    50                  55                  60

Gln
65

<210> SEQ ID NO 46
<211> LENGTH: 65
<212> TYPE: PRT
<213> ORGANISM: Artificial sequence
<220> FEATURE:
<223> OTHER INFORMATION: Fynomer #46

<400> SEQUENCE: 46

Gly Val Thr Leu Phe Val Ala Leu Tyr Asp Tyr Val Ser Tyr Asn Thr
1               5                   10                  15

Thr Asp Leu Ser Phe His Lys Gly Glu Lys Phe Gln Ile Leu Ser His
            20                  25                  30

Thr Thr Ser Gln Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
    50                  55                  60

Gln
65

<210> SEQ ID NO 47
<211> LENGTH: 63
<212> TYPE: PRT
<213> ORGANISM: Artificial sequence
<220> FEATURE:
<223> OTHER INFORMATION: Fynomer #47

<400> SEQUENCE: 47

Gly Val Thr Leu Phe Val Ala Leu Tyr Asp Tyr Thr Ser Tyr Asn Thr
1               5                   10                  15

Thr Asp Leu Ser Phe His Lys Gly Glu Lys Phe Gln Ile Leu Ser Met
            20                  25                  30

Ala Val Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60

<210> SEQ ID NO 48
<211> LENGTH: 65
<212> TYPE: PRT
<213> ORGANISM: Artificial sequence
<220> FEATURE:
<223> OTHER INFORMATION: Fynomer #48

<400> SEQUENCE: 48

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Asn
            20                  25                  30

Gly Pro Asp Pro Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
    50                  55                  60

Gln
65
```

<210> SEQ ID NO 49
<211> LENGTH: 63
<212> TYPE: PRT
<213> ORGANISM: Artificial sequence
<220> FEATURE:
<223> OTHER INFORMATION: Fynomer #49

<400> SEQUENCE: 49

Gly Val Thr Leu Phe Val Ala Leu Tyr Asp Tyr Thr Ser Tyr Asn Thr
1               5                   10                  15

Thr Asp Leu Ser Phe His Lys Gly Glu Lys Phe Gln Ile Leu Ser Asn
            20                  25                  30

Pro Pro Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 50
<211> LENGTH: 65
<212> TYPE: PRT
<213> ORGANISM: Artificial sequence
<220> FEATURE:
<223> OTHER INFORMATION: Fynomer #50

<400> SEQUENCE: 50

Gly Val Thr Leu Phe Val Ala Leu Tyr Asp Tyr Asn Ser Tyr Asn Lys
1               5                   10                  15

Arg Asp Leu Ser Phe His Lys Gly Glu Lys Phe Gln Ile Leu Ser Gln
            20                  25                  30

Ala Ala Glu Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 51
<211> LENGTH: 63
<212> TYPE: PRT
<213> ORGANISM: Artificial sequence
<220> FEATURE:
<223> OTHER INFORMATION: Fynomer #51

<400> SEQUENCE: 51

Gly Val Thr Leu Phe Val Ala Leu Tyr Asp Tyr Thr Ser Tyr Asn Thr
1               5                   10                  15

Lys Asp Leu Ser Phe His Lys Gly Glu Lys Phe Gln Ile Leu Ser Gln
            20                  25                  30

Ser Gly Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 52
<211> LENGTH: 65
<212> TYPE: PRT
<213> ORGANISM: Artificial sequence
<220> FEATURE:
<223> OTHER INFORMATION: Fynomer #52

<400> SEQUENCE: 52

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Tyr
                20                  25                  30

Pro Arg Thr Gln Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
        50                  55                  60

Gln
65

<210> SEQ ID NO 53
<211> LENGTH: 65
<212> TYPE: PRT
<213> ORGANISM: Artificial sequence
<220> FEATURE:
<223> OTHER INFORMATION: Fynomer #53

<400> SEQUENCE: 53

Gly Val Thr Leu Phe Val Ala Leu Tyr Asp Tyr Thr Ser Tyr Asn Glu
1               5                   10                  15

Arg Asp Leu Ser Phe His Lys Gly Glu Lys Phe Gln Ile Leu Thr Lys
                20                  25                  30

Thr Pro Arg Gln Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
        50                  55                  60

Gln
65

<210> SEQ ID NO 54
<211> LENGTH: 65
<212> TYPE: PRT
<213> ORGANISM: Artificial sequence
<220> FEATURE:
<223> OTHER INFORMATION: Fynomer #54

<400> SEQUENCE: 54

Gly Val Thr Leu Phe Val Ala Leu Tyr Asp Tyr Val Ser Tyr Asn Thr
1               5                   10                  15

Asn Asp Leu Ser Phe His Lys Gly Glu Lys Phe Gln Ile Leu Asp Ser
                20                  25                  30

Gln Glu Pro Asn Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
        50                  55                  60

Gln
65

<210> SEQ ID NO 55
<211> LENGTH: 65
<212> TYPE: PRT
<213> ORGANISM: Artificial sequence
<220> FEATURE:
<223> OTHER INFORMATION: Fynomer #55

<400> SEQUENCE: 55

Gly Val Thr Leu Phe Val Ala Leu Tyr Asp Tyr Thr Ser Tyr Asn Gln
1               5                   10                  15

His Asp Leu Ser Phe His Lys Gly Glu Lys Phe Gln Ile Leu Gly Gln
            20                  25                  30

Tyr Pro Lys Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 56
<211> LENGTH: 65
<212> TYPE: PRT
<213> ORGANISM: Artificial sequence
<220> FEATURE:
<223> OTHER INFORMATION: Fynomer #56

<400> SEQUENCE: 56

Gly Val Thr Leu Phe Val Ala Leu Tyr Asp Tyr Thr Ser Tyr Asn Asn
1               5                   10                  15

Thr Asp Leu Ser Phe His Lys Gly Glu Lys Phe Gln Ile Leu Lys Gln
            20                  25                  30

Gln Ala Gly Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 57
<211> LENGTH: 65
<212> TYPE: PRT
<213> ORGANISM: Artificial sequence
<220> FEATURE:
<223> OTHER INFORMATION: Fynomer #57

<400> SEQUENCE: 57

Gly Val Thr Leu Phe Val Ala Leu Tyr Asp Tyr Thr Ser Tyr Asn Asn
1               5                   10                  15

Thr Asp Leu Ser Phe His Lys Gly Glu Lys Phe Gln Ile Leu Asn Ala
            20                  25                  30

His Gln Ser Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 58
<211> LENGTH: 65
<212> TYPE: PRT
<213> ORGANISM: Artificial sequence
<220> FEATURE:
<223> OTHER INFORMATION: Fynomer #58

<400> SEQUENCE: 58

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Asn Pro
            20                  25                  30

Gln Ser Arg Thr Gly Asp Trp Trp Glu Ala Arg Ser Leu Thr Thr Gly 35                  40                  45
Glu Thr Gly Tyr Ile Pro Ser Asn Tyr Val Ala Pro Val Asp Ser Ile
    50                  55                  60

Gln
65

<210> SEQ ID NO 59
<211> LENGTH: 65
<212> TYPE: PRT
<213> ORGANISM: Artificial sequence
<220> FEATURE:
<223> OTHER INFORMATION: Fynomer #59

<400> SEQUENCE: 59

Gly Val Thr Leu Phe Val Ala Leu Tyr Asp Tyr Thr Ser Tyr Asn Ser
1               5                  10                  15

His Asp Leu Ser Phe His Lys Gly Glu Lys Phe Gln Ile Leu Pro Gly
                20                  25                  30

Gln Ser Met Thr Gly Asp Trp Trp Glu Ala Arg Ser Leu Thr Thr Gly
                35                  40                  45

Glu Thr Gly Tyr Ile Pro Ser Asn Tyr Val Ala Pro Val Asp Ser Ile
    50                  55                  60

Gln
65

<210> SEQ ID NO 60
<211> LENGTH: 65
<212> TYPE: PRT
<213> ORGANISM: Artificial sequence
<220> FEATURE:
<223> OTHER INFORMATION: Fynomer #60

<400> SEQUENCE: 60

Gly Val Thr Leu Phe Val Ala Leu Tyr Asp Tyr Thr Ser Tyr Asn Ala
1               5                  10                  15

His Asp Leu Ser Phe His Lys Gly Glu Lys Phe Gln Ile Leu Pro Arg
                20                  25                  30

Gln Asp Thr Ala Gly Asp Trp Trp Glu Ala Arg Ser Leu Thr Thr Gly
                35                  40                  45

Glu Thr Gly Tyr Ile Pro Ser Asn Tyr Val Ala Pro Val Asp Ser Ile
    50                  55                  60

Gln
65

<210> SEQ ID NO 61
<211> LENGTH: 63
<212> TYPE: PRT
<213> ORGANISM: Artificial sequence
<220> FEATURE:
<223> OTHER INFORMATION: Fynomer #61

<400> SEQUENCE: 61

Gly Val Thr Leu Phe Val Ala Leu Tyr Asp Tyr Thr Ser Tyr Asn Thr
1               5                  10                  15

Arg Asp Leu Ser Phe His Lys Gly Glu Lys Phe Gln Ile Leu Gln Ala
                20                  25                  30

Leu Gly Gly Asp Trp Trp Glu Ala Arg Ser Leu Thr Thr Gly Glu Thr
                35                  40                  45

Gly Tyr Ile Pro Ser Asn Tyr Val Ala Pro Val Asp Ser Ile Gln
    50                  55                  60

<210> SEQ ID NO 62
<211> LENGTH: 65
<212> TYPE: PRT
<213> ORGANISM: Artificial sequence
<220> FEATURE:
<223> OTHER INFORMATION: Fynomer #62

<400> SEQUENCE: 62

Gly Val Thr Leu Phe Val Ala Leu Tyr Asp Tyr Thr Ser Tyr Asn Glu
1               5                   10                  15

Phe Asp Leu Ser Phe His Lys Gly Glu Lys Phe Gln Ile Leu Gln Gly
            20                  25                  30

Thr Gln Leu Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 63
<211> LENGTH: 63
<212> TYPE: PRT
<213> ORGANISM: Artificial sequence
<220> FEATURE:
<223> OTHER INFORMATION: Fynomer #63

<400> SEQUENCE: 63

Gly Val Thr Leu Phe Val Ala Leu Tyr Asp Tyr Thr Ser Tyr Asn Asp
1               5                   10                  15

Arg Asp Leu Ser Phe His Lys Gly Glu Lys Phe Gln Ile Leu Gln His
            20                  25                  30

Lys Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 64
<211> LENGTH: 63
<212> TYPE: PRT
<213> ORGANISM: Artificial sequence
<220> FEATURE:
<223> OTHER INFORMATION: Fynomer #64

<400> SEQUENCE: 64

Gly Val Thr Leu Phe Val Ala Leu Tyr Asp Tyr Tyr Ser Tyr Asn Asn
1               5                   10                  15

Thr Asp Leu Ser Phe His Lys Gly Glu Lys Phe Gln Ile Leu Gln Lys
            20                  25                  30

Arg Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 65
<211> LENGTH: 63
<212> TYPE: PRT
<213> ORGANISM: Artificial sequence
<220> FEATURE:
<223> OTHER INFORMATION: Fynomer #65

<400> SEQUENCE: 65

```
Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Gln Lys
            20                  25                  30

Ser Gln Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60
```

<210> SEQ ID NO 66
<211> LENGTH: 65
<212> TYPE: PRT
<213> ORGANISM: Artificial sequence
<220> FEATURE:
<223> OTHER INFORMATION: Fynomer #66

<400> SEQUENCE: 66

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gln Pro
            20                  25                  30

Asn Ser Ala Gln Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
    50                  55                  60

Gln
65
```

<210> SEQ ID NO 67
<211> LENGTH: 63
<212> TYPE: PRT
<213> ORGANISM: Artificial sequence
<220> FEATURE:
<223> OTHER INFORMATION: Fynomer #67

<400> SEQUENCE: 67

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gln Pro
            20                  25                  30

Gln Val Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60
```

<210> SEQ ID NO 68
<211> LENGTH: 63
<212> TYPE: PRT
<213> ORGANISM: Artificial sequence
<220> FEATURE:
<223> OTHER INFORMATION: Fynomer #68

<400> SEQUENCE: 68

```
Gly Val Thr Leu Phe Val Ala Leu Tyr Asp Tyr Tyr Ser Tyr Asn Lys
1               5                   10                  15

Thr Asp Leu Ser Phe His Lys Gly Glu Lys Phe Gln Ile Leu Gln Gln
            20                  25                  30

His Glu Gly Asp Trp Trp Glu Ala Arg Ser Leu Thr Thr Gly Glu Thr
            35                  40                  45
```

```
Gly Tyr Ile Pro Ser Asn Tyr Val Ala Pro Val Asp Ser Ile Gln
    50                  55                  60
```

<210> SEQ ID NO 69
<211> LENGTH: 64
<212> TYPE: PRT
<213> ORGANISM: Artificial sequence
<220> FEATURE:
<223> OTHER INFORMATION: Fynomer #69

<400> SEQUENCE: 69

```
Gly Val Thr Leu Phe Val Ala Leu Tyr Asp Tyr Thr Ser Tyr Asn Leu
1               5                   10                  15

Arg Asp Leu Ser Phe His Lys Gly Glu Lys Phe Gln Ile Leu Gln Gln
            20                  25                  30

Asn Leu Asp Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 70
<211> LENGTH: 63
<212> TYPE: PRT
<213> ORGANISM: Artificial sequence
<220> FEATURE:
<223> OTHER INFORMATION: Fynomer #70

<400> SEQUENCE: 70

```
Gly Val Thr Leu Phe Val Ala Leu Tyr Asp Tyr Thr Ser Tyr Asn Leu
1               5                   10                  15

Arg Asp Leu Ser Phe His Lys Gly Glu Lys Phe Gln Ile Leu Gln Ser
            20                  25                  30

His Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 71
<211> LENGTH: 64
<212> TYPE: PRT
<213> ORGANISM: Artificial sequence
<220> FEATURE:
<223> OTHER INFORMATION: Fynomer #71

<400> SEQUENCE: 71

```
Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Gln Ser
            20                  25                  30

Arg Ala Ser Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60
```

<210> SEQ ID NO 72
<211> LENGTH: 64
<212> TYPE: PRT
<213> ORGANISM: Artificial sequence
<220> FEATURE:
<223> OTHER INFORMATION: Fynomer #72

<400> SEQUENCE: 72

Gly Val Thr Leu Phe Val Ala Leu Tyr Asp Tyr Thr Ser Tyr Asn Ala
1               5                   10                  15

Arg Asp Leu Ser Phe His Lys Gly Glu Lys Phe Gln Ile Leu Gln Thr
            20                  25                  30

Ser Leu Thr Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 73
<211> LENGTH: 64
<212> TYPE: PRT
<213> ORGANISM: Artificial sequence
<220> FEATURE:
<223> OTHER INFORMATION: Fynomer #73

<400> SEQUENCE: 73

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Gln Thr
            20                  25                  30

Thr Ala Met Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 74
<211> LENGTH: 65
<212> TYPE: PRT
<213> ORGANISM: Artificial sequence
<220> FEATURE:
<223> OTHER INFORMATION: Fynomer #74

<400> SEQUENCE: 74

Gly Val Thr Leu Phe Val Ala Leu Tyr Asp Tyr Thr Ser Tyr Asn Arg
1               5                   10                  15

Arg Asp Leu Ser Phe His Lys Gly Glu Lys Phe Gln Ile Leu Gln Val
            20                  25                  30

Asn Pro Met Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 75
<211> LENGTH: 64
<212> TYPE: PRT
<213> ORGANISM: Artificial sequence
<220> FEATURE:
<223> OTHER INFORMATION: Fynomer #75

<400> SEQUENCE: 75

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Gln
            20                  25                  30

Gln Arg Gly Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln

<210> SEQ ID NO 76
<211> LENGTH: 65
<212> TYPE: PRT
<213> ORGANISM: Artificial sequence
<220> FEATURE:
<223> OTHER INFORMATION: Fynomer #76

<400> SEQUENCE: 76

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Val
            20                  25                  30

Pro Gln Asp Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 77
<211> LENGTH: 64
<212> TYPE: PRT
<213> ORGANISM: Artificial sequence
<220> FEATURE:
<223> OTHER INFORMATION: Fynomer #77

<400> SEQUENCE: 77

Gly Val Thr Leu Phe Val Ala Leu Tyr Asp Tyr Thr Ser Tyr Asn Pro
1               5                   10                  15

Asn Asp Leu Ser Phe His Lys Gly Glu Lys Phe Gln Ile Leu Ser Gln
            20                  25                  30

Gln Asp Gly Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 78
<211> LENGTH: 65
<212> TYPE: PRT
<213> ORGANISM: Artificial sequence
<220> FEATURE:
<223> OTHER INFORMATION: Fynomer #78

<400> SEQUENCE: 78

Gly Val Thr Leu Phe Val Ala Leu Tyr Asp Tyr Thr Ser Tyr Asn Arg
1               5                   10                  15

Arg Asp Leu Ser Phe His Lys Gly Glu Lys Phe Gln Ile Leu Ser Ser
            20                  25                  30

Asn Arg Ala Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 79
<211> LENGTH: 65
<212> TYPE: PRT
<213> ORGANISM: Artificial sequence
<220> FEATURE:
<223> OTHER INFORMATION: Fynomer #79

<400> SEQUENCE: 79

Gly Val Thr Leu Phe Val Ala Leu Tyr Asp Tyr Thr Ser Tyr Asn Asn
1               5                   10                  15

Arg Asp Leu Ser Phe His Lys Gly Glu Lys Phe Gln Ile Leu Thr Pro
            20                  25                  30

Asp Ser Arg Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 80
<211> LENGTH: 64
<212> TYPE: PRT
<213> ORGANISM: Artificial sequence
<220> FEATURE:
<223> OTHER INFORMATION: Fynomer #80

<400> SEQUENCE: 80

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Thr Pro
            20                  25                  30

Pro Gln His Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 81
<211> LENGTH: 65
<212> TYPE: PRT
<213> ORGANISM: Artificial sequence
<220> FEATURE:
<223> OTHER INFORMATION: Fynomer #081

<400> SEQUENCE: 81

Gly Val Thr Leu Phe Val Ala Leu Tyr Asp Tyr Thr Ser Tyr Asn Asn
1               5                   10                  15

Thr Asp Leu Ser Phe His Lys Gly Glu Lys Phe Gln Ile Leu Thr Gln
            20                  25                  30

Asp Pro Leu His Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 82
<211> LENGTH: 63
<212> TYPE: PRT
<213> ORGANISM: Artificial sequence
<220> FEATURE:
<223> OTHER INFORMATION: Fynomer #82

<400> SEQUENCE: 82

Gly Val Thr Leu Phe Val Ala Leu Tyr Asp Tyr Thr Ser Tyr Asn Asp
1               5                   10                  15

Arg Asp Leu Ser Phe His Lys Gly Glu Lys Phe Gln Ile Leu Thr Gln
            20                  25                  30

Lys Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 83
<211> LENGTH: 65
<212> TYPE: PRT
<213> ORGANISM: Artificial sequence
<220> FEATURE:
<223> OTHER INFORMATION: Fynomer #83

<400> SEQUENCE: 83

Gly Val Thr Leu Phe Val Ala Leu Tyr Asp Tyr Ser Ser Tyr Asn Thr
1               5                   10                  15

Thr Asp Leu Ser Phe His Lys Gly Glu Lys Phe Gln Ile Leu Thr Gln
            20                  25                  30

Pro Pro Leu Ser Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 84
<211> LENGTH: 65
<212> TYPE: PRT
<213> ORGANISM: Artificial sequence
<220> FEATURE:
<223> OTHER INFORMATION: Fynomer #84

<400> SEQUENCE: 84

Gly Val Thr Leu Phe Val Ala Leu Tyr Asp Tyr Thr Ser Tyr Asn Thr
1               5                   10                  15

Gln Asp Leu Ser Phe His Lys Gly Glu Lys Phe Gln Ile Leu Asp Ser
            20                  25                  30

Glu Thr Gly Lys Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 85
<211> LENGTH: 65
<212> TYPE: PRT
<213> ORGANISM: Artificial sequence
<220> FEATURE:
<223> OTHER INFORMATION: Fynomer #85

<400> SEQUENCE: 85

Gly Val Thr Leu Phe Val Ala Leu Tyr Asp Tyr Thr Ser Tyr Asn Gln
1               5                   10                  15

Arg Asp Leu Ser Phe His Lys Gly Glu Lys Phe Gln Ile Leu Arg Lys
            20                  25                  30

Pro Lys Tyr Asn Gly Asp Trp Trp Glu Ala Arg Ser Leu Thr Thr Gly
        35                  40                  45

```
Glu Thr Gly Tyr Ile Pro Ser Asn Tyr Val Ala Pro Val Asp Ser Ile
         50                  55                  60
Gln
65
```

<210> SEQ ID NO 86
<211> LENGTH: 63
<212> TYPE: PRT
<213> ORGANISM: Artificial sequence
<220> FEATURE:
<223> OTHER INFORMATION: Fynomer #86

<400> SEQUENCE: 86

```
Gly Val Thr Leu Phe Val Ala Leu Tyr Asp Tyr Thr Ser Tyr Asn Gln
1               5                   10                  15

Arg Asp Leu Ser Phe His Lys Gly Glu Lys Phe Gln Ile Leu Ser Glu
             20                  25                  30

Pro Leu Gly Asp Trp Trp Glu Ala Arg Ser Leu Thr Thr Gly Glu Thr
         35                  40                  45

Gly Tyr Ile Pro Ser Asn Tyr Val Ala Pro Val Asp Ser Ile Gln
     50                  55                  60
```

<210> SEQ ID NO 87
<211> LENGTH: 64
<212> TYPE: PRT
<213> ORGANISM: Artificial sequence
<220> FEATURE:
<223> OTHER INFORMATION: Fynomer #87

<400> SEQUENCE: 87

```
Gly Val Thr Leu Phe Val Ala Leu Tyr Asp Tyr Thr Ser Tyr Asn Gln
1               5                   10                  15

Arg Asp Leu Ser Phe His Lys Gly Glu Lys Phe Gln Ile Leu Val His
             20                  25                  30

Asp Pro Ala Gly Asp Trp Trp Glu Ala Arg Ser Leu Thr Thr Gly Glu
         35                  40                  45

Thr Gly Tyr Ile Pro Ser Asn Tyr Val Ala Pro Val Asp Ser Ile Gln
     50                  55                  60
```

<210> SEQ ID NO 88
<211> LENGTH: 62
<212> TYPE: PRT
<213> ORGANISM: Artificial sequence
<220> FEATURE:
<223> OTHER INFORMATION: Fynomer #88

<400> SEQUENCE: 88

```
Gly Val Thr Leu Phe Val Ala Leu Tyr Asp Tyr Val Ser Trp Asn Thr
1               5                   10                  15

Leu Asp Leu Ser Phe His Lys Gly Glu Lys Phe Gln Ile Leu Arg Met
             20                  25                  30

Pro Gly Asp Trp Trp Glu Ala Arg Ser Leu Thr Thr Gly Glu Thr Gly
         35                  40                  45

Tyr Ile Pro Ser Asn Tyr Val Ala Pro Val Asp Ser Ile Gln
     50                  55                  60
```

<210> SEQ ID NO 89
<211> LENGTH: 64
<212> TYPE: PRT
<213> ORGANISM: Artificial sequence
<220> FEATURE:
<223> OTHER INFORMATION: Fynomer #89

<400> SEQUENCE: 89

Gly Val Thr Leu Phe Val Ala Leu Tyr Asp Tyr Glu Ala Arg Leu Tyr
1               5                   10                  15

Ser Leu Asp Leu Ser Phe His Lys Gly Glu Lys Phe Gln Ile Leu Asn
            20                  25                  30

Arg Arg Trp Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 90
<211> LENGTH: 64
<212> TYPE: PRT
<213> ORGANISM: Artificial sequence
<220> FEATURE:
<223> OTHER INFORMATION: Fynomer #90

<400> SEQUENCE: 90

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Ala Pro
            20                  25                  30

Pro Asn Gly Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 91
<211> LENGTH: 64
<212> TYPE: PRT
<213> ORGANISM: Artificial sequence
<220> FEATURE:
<223> OTHER INFORMATION: Fynomer #91

<400> SEQUENCE: 91

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Ala Arg
            20                  25                  30

Met Pro Pro Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 92
<211> LENGTH: 66
<212> TYPE: PRT
<213> ORGANISM: Artificial sequence
<220> FEATURE:
<223> OTHER INFORMATION: Fynomer #92

<400> SEQUENCE: 92

Gly Val Thr Leu Phe Val Ala Leu Tyr Asp Tyr Glu Ala Arg Phe Arg
1               5                   10                  15

Arg Asn Tyr Ser Asp Leu Ser Phe His Lys Gly Glu Lys Phe Gln Ile
            20                  25                  30

Leu Ser Ala Gln Gln Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser

-continued

```
            50                  55                  60

Ile Gln
 65

<210> SEQ ID NO 93
<211> LENGTH: 65
<212> TYPE: PRT
<213> ORGANISM: Artificial sequence
<220> FEATURE:
<223> OTHER INFORMATION: Fynomer #93

<400> SEQUENCE: 93

Gly Val Thr Leu Phe Val Ala Leu Tyr Asp Tyr Asp Arg Arg Tyr Gly
 1               5                  10                  15

Ala Asp Leu Ser Phe His Lys Gly Glu Lys Phe Gln Ile Leu Arg Asp
            20                  25                  30

Glu Ala Val Ser Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
 65

<210> SEQ ID NO 94
<211> LENGTH: 65
<212> TYPE: PRT
<213> ORGANISM: Artificial sequence
<220> FEATURE:
<223> OTHER INFORMATION: Fynomer #94

<400> SEQUENCE: 94

Gly Val Thr Leu Phe Val Ala Leu Tyr Asp Tyr Thr Ser Tyr Asn Thr
 1               5                  10                  15

Arg Asp Leu Ser Phe His Lys Gly Glu Lys Phe Gln Ile Leu His Asp
            20                  25                  30

Pro Pro Ser Asn Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
 65

<210> SEQ ID NO 95
<211> LENGTH: 64
<212> TYPE: PRT
<213> ORGANISM: Artificial sequence
<220> FEATURE:
<223> OTHER INFORMATION: Fynomer #95

<400> SEQUENCE: 95

Gly Val Thr Leu Phe Val Ala Leu Tyr Asp Tyr Glu Ala Arg Tyr Ala
 1               5                  10                  15

Pro Ala Asp Leu Ser Phe His Lys Gly Glu Lys Phe Gln Ile Leu Asn
            20                  25                  30

His Asp Arg Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 96
```

```
<211> LENGTH: 65
<212> TYPE: PRT
<213> ORGANISM: Artificial sequence
<220> FEATURE:
<223> OTHER INFORMATION: Fynomer #96

<400> SEQUENCE: 96
```

Gly Val Thr Leu Phe Val Ala Leu Tyr Asp Tyr Thr Ser Ser Tyr Pro
1               5                   10                  15

Gly Asp Leu Ser Phe His Lys Gly Glu Lys Phe Gln Ile Leu Ser Asn
            20                  25                  30

Asp Pro Val His Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

```
<210> SEQ ID NO 97
<211> LENGTH: 65
<212> TYPE: PRT
<213> ORGANISM: Artificial sequence
<220> FEATURE:
<223> OTHER INFORMATION: Fynomer #97

<400> SEQUENCE: 97
```

Gly Val Thr Leu Phe Val Ala Leu Tyr Asp Tyr Gln Thr Trp Thr Pro
1               5                   10                  15

Gly Asp Leu Ser Phe His Lys Gly Glu Lys Phe Gln Ile Leu Thr Gln
            20                  25                  30

Asp Glu Gln Gln Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

```
<210> SEQ ID NO 98
<211> LENGTH: 65
<212> TYPE: PRT
<213> ORGANISM: Artificial sequence
<220> FEATURE:
<223> OTHER INFORMATION: Fynomer #98

<400> SEQUENCE: 98
```

Gly Val Thr Leu Phe Val Ala Leu Tyr Asp Tyr Phe Thr Asn Thr Pro
1               5                   10                  15

Gly Asp Leu Ser Phe His Lys Gly Glu Lys Phe Gln Ile Leu Asn Thr
            20                  25                  30

Ser Tyr Leu Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

```
<210> SEQ ID NO 99
<211> LENGTH: 63
<212> TYPE: PRT
<213> ORGANISM: Artificial sequence
<220> FEATURE:
```

<223> OTHER INFORMATION: Fynomer #99

<400> SEQUENCE: 99

Gly Val Thr Leu Phe Val Ala Leu Tyr Asp Tyr Lys Thr His Asn Pro
1               5                   10                  15

Gly Asp Leu Ser Phe His Lys Gly Glu Lys Phe Gln Ile Leu Gln Gly
            20                  25                  30

Arg Val Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 100
<211> LENGTH: 65
<212> TYPE: PRT
<213> ORGANISM: Artificial sequence
<220> FEATURE:
<223> OTHER INFORMATION: Fynomer #100

<400> SEQUENCE: 100

Gly Val Thr Leu Phe Val Ala Leu Tyr Asp Tyr Gln Thr Tyr Thr Pro
1               5                   10                  15

Gly Asp Leu Ser Phe His Lys Gly Glu Lys Phe Gln Ile Leu Ser Lys
            20                  25                  30

Pro Pro Gln Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 101
<211> LENGTH: 65
<212> TYPE: PRT
<213> ORGANISM: Artificial sequence
<220> FEATURE:
<223> OTHER INFORMATION: Fynomer #101

<400> SEQUENCE: 101

Gly Val Thr Leu Phe Val Ala Leu Tyr Asp Tyr Glu Ala Arg Tyr Gln
1               5                   10                  15

Asp Leu Glu Asp Leu Ser Phe His Lys Gly Glu Lys Phe Gln Ile Leu
            20                  25                  30

Asn Gly Arg Arg Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 102
<211> LENGTH: 63
<212> TYPE: PRT
<213> ORGANISM: Artificial sequence
<220> FEATURE:
<223> OTHER INFORMATION: Fynomer #102

<400> SEQUENCE: 102

Gly Val Thr Leu Phe Val Ala Leu Tyr Asp Tyr Asp Arg His Tyr Thr
1               5                   10                  15

```
Phe Asp Leu Ser Phe His Lys Gly Glu Lys Phe Gln Ile Leu Gln Asn
                20                  25                  30

Lys Gln Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60

<210> SEQ ID NO 103
<211> LENGTH: 63
<212> TYPE: PRT
<213> ORGANISM: Artificial sequence
<220> FEATURE:
<223> OTHER INFORMATION: Fynomer #103

<400> SEQUENCE: 103

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Asp
                20                  25                  30

Ser Asp Gly Val Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60

<210> SEQ ID NO 104
<211> LENGTH: 65
<212> TYPE: PRT
<213> ORGANISM: Artificial sequence
<220> FEATURE:
<223> OTHER INFORMATION: Fynomer #104

<400> SEQUENCE: 104

Gly Val Thr Leu Phe Val Ala Leu Tyr Asp Tyr Glu Ala Arg Asp Arg
1               5                   10                  15

Pro Thr Asp Leu Ser Phe His Lys Gly Glu Lys Phe Gln Ile Leu Gly
                20                  25                  30

Asp Glu Gln Ile Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
        50                  55                  60

Gln
65

<210> SEQ ID NO 105
<211> LENGTH: 64
<212> TYPE: PRT
<213> ORGANISM: Artificial sequence
<220> FEATURE:
<223> OTHER INFORMATION: Fynomer #105

<400> SEQUENCE: 105

Gly Val Thr Leu Phe Val Ala Leu Tyr Asp Tyr Thr Thr Tyr Arg Lys
1               5                   10                  15

Gly Asp Leu Ser Phe His Lys Gly Glu Lys Phe Gln Ile Leu Asn Arg
                20                  25                  30

Val Ser Ile Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60
```

-continued

```
<210> SEQ ID NO 106
<211> LENGTH: 64
<212> TYPE: PRT
<213> ORGANISM: Artificial sequence
<220> FEATURE:
<223> OTHER INFORMATION: Fynomer #106

<400> SEQUENCE: 106

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Asn Arg
            20                  25                  30

Val Ser Ile Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 107
<211> LENGTH: 63
<212> TYPE: PRT
<213> ORGANISM: Artificial sequence
<220> FEATURE:
<223> OTHER INFORMATION: Fynomer #107

<400> SEQUENCE: 107

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gly Asp
            20                  25                  30

Asn Ile Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 108
<211> LENGTH: 63
<212> TYPE: PRT
<213> ORGANISM: Artificial sequence
<220> FEATURE:
<223> OTHER INFORMATION: Fynomer #108

<400> SEQUENCE: 108

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Asn Ser
            20                  25                  30

Ser Asp Gly Thr Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 109
<211> LENGTH: 64
<212> TYPE: PRT
<213> ORGANISM: Artificial sequence
<220> FEATURE:
<223> OTHER INFORMATION: Fynomer #109

<400> SEQUENCE: 109

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Trp Ser
```

```
                  20                  25                  30

Asp Ala Leu Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 110
<211> LENGTH: 63
<212> TYPE: PRT
<213> ORGANISM: Artificial sequence
<220> FEATURE:
<223> OTHER INFORMATION: Fynomer #110

<400> SEQUENCE: 110

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Met Ala
            20                  25                  30

Trp Ala Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 111
<211> LENGTH: 65
<212> TYPE: PRT
<213> ORGANISM: Artificial sequence
<220> FEATURE:
<223> OTHER INFORMATION: Fynomer #111

<400> SEQUENCE: 111

Gly Val Thr Leu Phe Val Ala Leu Tyr Asp Tyr Glu Ala Arg Glu Gly
1               5                   10                  15

Gly Asn Asp Leu Ser Phe His Lys Gly Glu Lys Phe Gln Ile Leu Asn
            20                  25                  30

Arg Val Ser Ile Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 112
<211> LENGTH: 66
<212> TYPE: PRT
<213> ORGANISM: Artificial sequence
<220> FEATURE:
<223> OTHER INFORMATION: Fynomer #112

<400> SEQUENCE: 112

Gly Val Thr Leu Phe Val Ala Leu Tyr Asp Tyr Glu Ala His Asp Gln
1               5                   10                  15

His Arg Pro Asp Leu Ser Phe His Lys Gly Glu Lys Phe Gln Ile Leu
            20                  25                  30

Asn Arg Val Ser Ile Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65
```

<210> SEQ ID NO 113
<211> LENGTH: 66
<212> TYPE: PRT
<213> ORGANISM: Artificial sequence
<220> FEATURE:
<223> OTHER INFORMATION: Fynomer #113

<400> SEQUENCE: 113

Gly Val Thr Leu Phe Val Ala Leu Tyr Asp Tyr Glu Ala Arg Leu Ser
1               5                   10                  15

Ser His Pro His Val Leu Ser Phe His Lys Gly Glu Lys Phe Gln Ile
            20                  25                  30

Leu Asn Ser Ser Ala Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65

<210> SEQ ID NO 114
<211> LENGTH: 64
<212> TYPE: PRT
<213> ORGANISM: Artificial sequence
<220> FEATURE:
<223> OTHER INFORMATION: Fynomer #114

<400> SEQUENCE: 114

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Leu Met
            20                  25                  30

His Pro Gly Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 115
<211> LENGTH: 64
<212> TYPE: PRT
<213> ORGANISM: Artificial sequence
<220> FEATURE:
<223> OTHER INFORMATION: Fynomer #115

<400> SEQUENCE: 115

Gly Val Thr Leu Phe Val Ala Leu Tyr Asp Tyr Glu Ala Arg His Ala
1               5                   10                  15

Pro Val Asp Leu Ser Phe His Lys Gly Glu Lys Phe Gln Ile Leu Gly
            20                  25                  30

Asp Asn Ile Gly Asp Trp Trp Glu Ala Arg Ser Leu Thr Thr Gly Glu
        35                  40                  45

Thr Gly Tyr Ile Pro Ser Asn Tyr Val Ala Pro Val Asp Ser Ile Gln
    50                  55                  60

<210> SEQ ID NO 116
<211> LENGTH: 64
<212> TYPE: PRT
<213> ORGANISM: Artificial sequence
<220> FEATURE:
<223> OTHER INFORMATION: Fynomer #116

<400> SEQUENCE: 116

```
Gly Val Thr Leu Phe Val Ala Leu Tyr Asp Tyr Glu Ala Arg Thr Lys
1               5                   10                  15

His Phe Asp Leu Ser Phe His Lys Gly Glu Lys Phe Gln Ile Leu Ser
                20                  25                  30

Gln Pro His Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60
```

<210> SEQ ID NO 117
<211> LENGTH: 64
<212> TYPE: PRT
<213> ORGANISM: Artificial sequence
<220> FEATURE:
<223> OTHER INFORMATION: Fynomer #117

<400> SEQUENCE: 117

```
Gly Val Thr Leu Phe Val Ala Leu Tyr Asp Tyr Glu Ala Arg His Glu
1               5                   10                  15

Asn Phe Asp Leu Ser Phe His Lys Gly Glu Lys Phe Gln Ile Leu Asn
                20                  25                  30

Arg Gly Ala Gly Asp Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60
```

<210> SEQ ID NO 118
<211> LENGTH: 65
<212> TYPE: PRT
<213> ORGANISM: Artificial sequence
<220> FEATURE:
<223> OTHER INFORMATION: Fynomer #118

<400> SEQUENCE: 118

```
Gly Val Thr Leu Phe Val Ala Leu Tyr Asp Tyr Glu Ala Arg Pro Asp
1               5                   10                  15

Ser His Asp Leu Ser Phe His Lys Gly Glu Lys Phe Gln Ile Leu Asn
                20                  25                  30

Arg Val Ser Ile Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
        50                  55                  60

Gln
65
```

<210> SEQ ID NO 119
<211> LENGTH: 63
<212> TYPE: PRT
<213> ORGANISM: Artificial sequence
<220> FEATURE:
<223> OTHER INFORMATION: Fynomer #119

<400> SEQUENCE: 119

```
Gly Val Thr Leu Phe Val Ala Leu Tyr Asp Tyr Glu Ala Arg Arg Thr
1               5                   10                  15

His Asp Leu Ser Phe His Lys Gly Glu Lys Phe Gln Ile Leu Ser Gln
                20                  25                  30

Pro His Gly Asp Trp Trp Glu Ala Arg Ser Leu Thr Thr Gly Glu Thr
            35                  40                  45
```

```
Gly Tyr Ile Pro Ser Asn Tyr Val Ala Pro Val Asp Ser Ile Gln
    50                  55                  60
```

<210> SEQ ID NO 120
<211> LENGTH: 65
<212> TYPE: PRT
<213> ORGANISM: Artificial sequence
<220> FEATURE:
<223> OTHER INFORMATION: Fynomer #120

<400> SEQUENCE: 120

```
Gly Val Thr Leu Phe Val Ala Leu Tyr Asp Tyr Glu Ala Arg Pro Met
1               5                   10                  15

Ser Ser Asp Leu Ser Phe His Lys Gly Glu Lys Phe Gln Ile Leu Asn
            20                  25                  30

Arg Val Ser Ile Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 121
<211> LENGTH: 63
<212> TYPE: PRT
<213> ORGANISM: Artificial sequence
<220> FEATURE:
<223> OTHER INFORMATION: Fynomer #121

<400> SEQUENCE: 121

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Phe
            20                  25                  30

Asn Pro Gly Asp Trp Trp Glu Ala Arg Ser Leu Thr Thr Gly Glu Thr
        35                  40                  45

Gly Tyr Ile Pro Ser Ser Tyr Val Ala Pro Val Asp Ser Ile Gln
    50                  55                  60
```

<210> SEQ ID NO 122
<211> LENGTH: 63
<212> TYPE: PRT
<213> ORGANISM: Artificial sequence
<220> FEATURE:
<223> OTHER INFORMATION: Fynomer #122

<400> SEQUENCE: 122

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Phe Pro
            20                  25                  30

Asp Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 123
<211> LENGTH: 63
<212> TYPE: PRT
<213> ORGANISM: Artificial sequence
<220> FEATURE:
<223> OTHER INFORMATION: Fynomer #123

<400> SEQUENCE: 123

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Gln
            20                  25                  30

Pro His Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 124
<211> LENGTH: 63
<212> TYPE: PRT
<213> ORGANISM: Artificial sequence
<220> FEATURE:
<223> OTHER INFORMATION: Fynomer #124

<400> SEQUENCE: 124

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Gly Lys
            20                  25                  30

Gly Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 125
<211> LENGTH: 63
<212> TYPE: PRT
<213> ORGANISM: Artificial sequence
<220> FEATURE:
<223> OTHER INFORMATION: Fynomer #125

<400> SEQUENCE: 125

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Ser Asp
            20                  25                  30

Gln His Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 126
<211> LENGTH: 63
<212> TYPE: PRT
<213> ORGANISM: Artificial sequence
<220> FEATURE:
<223> OTHER INFORMATION: Fynomer #126

<400> SEQUENCE: 126

Gly Val Thr Leu Phe Val Ala Leu Tyr Asp Tyr Thr Ser Tyr Asn Asp
1               5                   10                  15

Arg Asp Leu Ser Phe His Lys Gly Glu Lys Phe Gln Ile Leu Ser Ala
            20                  25                  30

Pro Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln

-continued

```
                50                  55                  60
```

<210> SEQ ID NO 127
<211> LENGTH: 63
<212> TYPE: PRT
<213> ORGANISM: Artificial sequence
<220> FEATURE:
<223> OTHER INFORMATION: Fynomer #127

<400> SEQUENCE: 127

```
Gly Val Thr Leu Phe Val Ala Leu Tyr Asp Tyr Thr Ser Tyr Asn Asp
1               5                   10                  15

Arg Asp Leu Ser Phe His Lys Gly Glu Lys Phe Gln Ile Leu Glu Tyr
            20                  25                  30

Thr Thr Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 128
<211> LENGTH: 65
<212> TYPE: PRT
<213> ORGANISM: Artificial sequence
<220> FEATURE:
<223> OTHER INFORMATION: Fynomer #128

<400> SEQUENCE: 128

```
Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Thr Thr
            20                  25                  30

Glu Ala Thr Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65
```

<210> SEQ ID NO 129
<211> LENGTH: 63
<212> TYPE: PRT
<213> ORGANISM: Artificial sequence
<220> FEATURE:
<223> OTHER INFORMATION: Fynomer #129

<400> SEQUENCE: 129

```
Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Gln Asn
            20                  25                  30

Ser Gln Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 130
<211> LENGTH: 63
<212> TYPE: PRT
<213> ORGANISM: Artificial sequence
<220> FEATURE:
<223> OTHER INFORMATION: Fynomer #130

```
<400> SEQUENCE: 130

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Gly Asn
                20                  25                  30

Thr Gln Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60

<210> SEQ ID NO 131
<211> LENGTH: 63
<212> TYPE: PRT
<213> ORGANISM: Artificial sequence
<220> FEATURE:
<223> OTHER INFORMATION: Fynomer #131

<400> SEQUENCE: 131

Gly Val Thr Leu Phe Val Ala Leu Tyr Asp Tyr Thr Ser Tyr Asn Ala
1               5                   10                  15

Gln Asp Leu Ser Phe His Lys Gly Glu Lys Phe Gln Ile Leu Gly Ala
                20                  25                  30

Arg Tyr Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60

<210> SEQ ID NO 132
<211> LENGTH: 63
<212> TYPE: PRT
<213> ORGANISM: Artificial sequence
<220> FEATURE:
<223> OTHER INFORMATION: Fynomer #132

<400> SEQUENCE: 132

Gly Val Thr Leu Phe Val Ala Leu Tyr Asp Tyr Thr Ser Tyr Asn Ala
1               5                   10                  15

Arg Asp Leu Ser Phe His Lys Gly Glu Lys Phe Gln Ile Leu Gly His
                20                  25                  30

His Ser Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60

<210> SEQ ID NO 133
<211> LENGTH: 63
<212> TYPE: PRT
<213> ORGANISM: Artificial sequence
<220> FEATURE:
<223> OTHER INFORMATION: Fynomer #133

<400> SEQUENCE: 133

Gly Val Thr Leu Phe Val Ala Leu Tyr Asp Tyr Thr Ser Tyr Asn Met
1               5                   10                  15

Arg Asp Leu Ser Phe His Lys Gly Glu Lys Phe Gln Ile Leu Asn Asn
                20                  25                  30

Ser Asp Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
    50                  55                  60
```

<210> SEQ ID NO 134
<211> LENGTH: 65
<212> TYPE: PRT
<213> ORGANISM: Artificial sequence
<220> FEATURE:
<223> OTHER INFORMATION: Fynomer #134

<400> SEQUENCE: 134

Gly Val Thr Leu Phe Val Ala Leu Tyr Asp Tyr Thr Ser Tyr Asn Asp
1               5                   10                  15

Arg Asp Leu Ser Phe His Lys Gly Glu Lys Phe Gln Ile Leu Ser Lys
            20                  25                  30

Asp Ser Ala Leu Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 135
<211> LENGTH: 63
<212> TYPE: PRT
<213> ORGANISM: Artificial sequence
<220> FEATURE:
<223> OTHER INFORMATION: Fynomer #135

<400> SEQUENCE: 135

Gly Val Thr Leu Phe Val Ala Leu Tyr Asp Tyr Thr Ser Tyr Asn Ser
1               5                   10                  15

Arg Asp Leu Ser Phe His Lys Gly Glu Lys Phe Gln Ile Leu Asn Arg
            20                  25                  30

Gly Ala Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 136
<211> LENGTH: 63
<212> TYPE: PRT
<213> ORGANISM: Artificial sequence
<220> FEATURE:
<223> OTHER INFORMATION: Fynomer #136

<400> SEQUENCE: 136

Gly Val Thr Leu Phe Val Ala Leu Tyr Asp Tyr Thr Ser Tyr Asn Thr
1               5                   10                  15

His Asp Leu Ser Phe His Lys Gly Glu Lys Phe Gln Ile Leu Lys Met
            20                  25                  30

Gln Ser Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 137
<211> LENGTH: 63
<212> TYPE: PRT
<213> ORGANISM: Artificial sequence
<220> FEATURE:
<223> OTHER INFORMATION: Fynomer #137

<400> SEQUENCE: 137

-continued

Gly Val Thr Leu Phe Val Ala Leu Tyr Asp Tyr Thr Ser Tyr Asn Arg
1               5                   10                  15

Arg Asp Leu Ser Phe His Lys Gly Glu Lys Phe Gln Ile Leu Glu Thr
                20                  25                  30

Gln Asn Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60

<210> SEQ ID NO 138
<211> LENGTH: 63
<212> TYPE: PRT
<213> ORGANISM: Artificial sequence
<220> FEATURE:
<223> OTHER INFORMATION: Fynomer #138

<400> SEQUENCE: 138

Gly Val Thr Leu Phe Val Ala Leu Tyr Asp Tyr Thr Ser Tyr Asn Ala
1               5                   10                  15

Arg Asp Leu Ser Phe His Lys Gly Glu Lys Phe Gln Ile Leu Gly Ser
                20                  25                  30

Thr Ala Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60

<210> SEQ ID NO 139
<211> LENGTH: 67
<212> TYPE: PRT
<213> ORGANISM: Artificial sequence
<220> FEATURE:
<223> OTHER INFORMATION: Fynomer #139

<400> SEQUENCE: 139

Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
                20                  25                  30

Leu Arg Ser Trp Pro Glu Gly Asp Trp Trp Glu Ala Arg Ser Leu Thr
            35                  40                  45

Thr Gly Glu Thr Gly Tyr Ile Pro Ser Asn Tyr Val Ala Pro Val Asp
        50                  55                  60

Ser Ile Gln
65

<210> SEQ ID NO 140
<211> LENGTH: 67
<212> TYPE: PRT
<213> ORGANISM: Artificial sequence
<220> FEATURE:
<223> OTHER INFORMATION: Fynomer #140

<400> SEQUENCE: 140

Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
                20                  25                  30

Leu Lys Thr Trp Glu Gly Gly Asp Trp Trp Glu Ala Arg Ser Leu Thr
            35                  40                  45

-continued

Thr Gly Glu Thr Gly Tyr Ile Pro Ser Asn Tyr Val Ala Pro Val Asp
    50                  55                  60

Ser Ile Gln
65

<210> SEQ ID NO 141
<211> LENGTH: 67
<212> TYPE: PRT
<213> ORGANISM: Artificial sequence
<220> FEATURE:
<223> OTHER INFORMATION: Fynomer #141

<400> SEQUENCE: 141

Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
            20                  25                  30

Leu Gln Ala Trp Gln Glu Gly Asp Trp Trp Glu Ala Arg Ser Leu Thr
        35                  40                  45

Thr Gly Glu Thr Gly Tyr Ile Pro Ser Asn Tyr Val Ala Pro Val Asp
    50                  55                  60

Ser Ile Gln
65

<210> SEQ ID NO 142
<211> LENGTH: 63
<212> TYPE: PRT
<213> ORGANISM: Artificial sequence
<220> FEATURE:
<223> OTHER INFORMATION: Fynomer #142

<400> SEQUENCE: 142

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Ala Ala Arg Ser Leu Thr Thr Gly Glu Ile
        35                  40                  45

Gly Tyr Ile Pro Ser Asn Tyr Val Ala Pro Val Asp Ser Ile Gln
    50                  55                  60

<210> SEQ ID NO 143
<211> LENGTH: 63
<212> TYPE: PRT
<213> ORGANISM: Artificial sequence
<220> FEATURE:
<223> OTHER INFORMATION: Fynomer #143

<400> SEQUENCE: 143

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Arg Ala Arg Ser Leu Thr Thr Gly Glu Ile
        35                  40                  45

Gly Leu Ile Pro Ser Asn Tyr Val Ala Pro Val Asp Ser Ile Gln
    50                  55                  60

<210> SEQ ID NO 144
<211> LENGTH: 63
<212> TYPE: PRT

<213> ORGANISM: Artificial sequence
<220> FEATURE:
<223> OTHER INFORMATION: Fynomer #144

<400> SEQUENCE: 144

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Thr Ala Arg Ser Leu Thr Thr Gly Glu Val
        35                  40                  45

Gly Phe Ile Pro Ser Asn Tyr Val Ala Pro Val Asp Ser Ile Gln
    50                  55                  60

<210> SEQ ID NO 145
<211> LENGTH: 63
<212> TYPE: PRT
<213> ORGANISM: Artificial sequence
<220> FEATURE:
<223> OTHER INFORMATION: Fynomer #145

<400> SEQUENCE: 145

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Ile Trp Trp Gln Ala Arg Ser Leu Thr Thr Gly Glu Thr
        35                  40                  45

Gly Phe Ile Pro Ser Asn Tyr Val Ala Pro Val Asp Ser Ile Gln
    50                  55                  60

<210> SEQ ID NO 146
<211> LENGTH: 65
<212> TYPE: PRT
<213> ORGANISM: Artificial sequence
<220> FEATURE:
<223> OTHER INFORMATION: Fynomer #146

<400> SEQUENCE: 146

Gly Val Thr Leu Phe Val Ala Leu Tyr Asp Tyr Gln Ala Tyr Gly Met
1               5                   10                  15

Tyr Asp Leu Ser Phe His Lys Gly Glu Lys Phe Gln Ile Leu Pro Pro
            20                  25                  30

Tyr Pro Thr Gly Gly Tyr Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 147
<211> LENGTH: 64
<212> TYPE: PRT
<213> ORGANISM: Artificial sequence
<220> FEATURE:
<223> OTHER INFORMATION: Fynomer #147

<400> SEQUENCE: 147

Gly Val Thr Leu Phe Val Ala Leu Tyr Asp Tyr Gln Ala Tyr Gly Met
1               5                   10                  15

Tyr Asp Leu Ser Phe His Lys Gly Glu Lys Phe Gln Ile Leu Gln Val

```
                    20                  25                  30

Leu Asp Asn Gly Tyr Trp Trp Glu Ala Arg Ser Leu Thr Thr Gly Glu
            35                  40                  45

Thr Gly Tyr Ile Pro Ser Asn Tyr Val Ala Pro Val Asp Ser Ile Gln
        50                  55                  60

<210> SEQ ID NO 148
<211> LENGTH: 65
<212> TYPE: PRT
<213> ORGANISM: Artificial sequence
<220> FEATURE:
<223> OTHER INFORMATION: Fynomer #148

<400> SEQUENCE: 148

Gly Val Thr Leu Phe Val Ala Leu Tyr Asp Tyr Gln Ala Tyr Gly Met
1               5                   10                  15

Tyr Asp Leu Ser Phe His Lys Gly Glu Lys Phe Gln Ile Leu Thr Ala
                20                  25                  30

Leu Pro Asp Arg Gly Tyr Trp Trp Glu Ala Arg Ser Leu Thr Thr Gly
            35                  40                  45

Glu Thr Gly Tyr Ile Pro Ser Asn Tyr Val Ala Pro Val Asp Ser Ile
        50                  55                  60

Gln
65

<210> SEQ ID NO 149
<211> LENGTH: 63
<212> TYPE: PRT
<213> ORGANISM: Artificial sequence
<220> FEATURE:
<223> OTHER INFORMATION: Fynomer #149

<400> SEQUENCE: 149

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Asp
                20                  25                  30

Asp Asp Gly Val Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60

<210> SEQ ID NO 150
<211> LENGTH: 65
<212> TYPE: PRT
<213> ORGANISM: Artificial sequence
<220> FEATURE:
<223> OTHER INFORMATION: Fynomer #150

<400> SEQUENCE: 150

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ser Phe
                20                  25                  30

Gln Ser Ala Gly Gly Val Trp Trp Glu Ala Arg Ser Leu Thr Thr Gly
            35                  40                  45

Glu Thr Gly Tyr Ile Pro Ser Asn Tyr Val Ala Pro Val Asp Ser Ile
        50                  55                  60

Gln
65
```

<210> SEQ ID NO 151
<211> LENGTH: 63
<212> TYPE: PRT
<213> ORGANISM: Artificial sequence
<220> FEATURE:
<223> OTHER INFORMATION: Fynomer #151

<400> SEQUENCE: 151

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Ala Arg
            20                  25                  30

Asp Asn Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 152
<211> LENGTH: 66
<212> TYPE: PRT
<213> ORGANISM: Artificial sequence
<220> FEATURE:
<223> OTHER INFORMATION: Fynomer #152

<400> SEQUENCE: 152

Gly Val Thr Leu Phe Val Ala Leu Tyr Asp Tyr Glu Ala Arg Asp Ser
1               5                   10                  15

Met Gly Gly Gln Asp Leu Ser Phe His Lys Gly Glu Lys Phe Gln Ile
            20                  25                  30

Leu Trp Asn Thr Gly Gly Asp Trp Trp Glu Ala Arg Ser Leu Thr Thr
        35                  40                  45

Gly Glu Thr Gly Tyr Ile Pro Ser Asn Tyr Val Ala Pro Val Asp Ser
    50                  55                  60

Ile Gln
65

<210> SEQ ID NO 153
<211> LENGTH: 305
<212> TYPE: PRT
<213> ORGANISM: Artificial sequence
<220> FEATURE:
<223> OTHER INFORMATION: Fc fusion of Fynomer C12 (Fynomer #1; SEQ ID
      NO:1)

<400> SEQUENCE: 153

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

```
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
210                 215                 220

Pro Gly Lys Gly Gly Gly Gly Ser Gly Gly Gly Gly Ser Gly Gly Gly
225                 230                 235                 240

Gly Ser Gly Val Thr Leu Phe Val Ala Leu Tyr Asp Tyr Thr Ser Tyr
                245                 250                 255

Asn Thr Arg Asp Leu Ser Phe His Lys Gly Glu Lys Phe Gln Ile Leu
            260                 265                 270

Arg Met Glu Asp Gly Val Trp Trp Glu Ala Arg Ser Leu Thr Thr Gly
            275                 280                 285

Glu Thr Gly Tyr Ile Pro Ser Asn Tyr Val Ala Pro Val Asp Ser Ile
            290                 295                 300

Gln
305

<210> SEQ ID NO 154
<211> LENGTH: 449
<212> TYPE: PRT
<213> ORGANISM: Artificial sequence
<220> FEATURE:
<223> OTHER INFORMATION: anti HER2 antibody 1, heavy chain

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 155
<211> LENGTH: 214
<212> TYPE: PRT
<213> ORGANISM: Artificial sequence
<220> FEATURE:
<223> OTHER INFORMATION: anti HER2 antibody 1, light chain

<400> SEQUENCE: 155

Asp Ile Gln Met Thr Gln Ser Pro Ser Ser Leu Ser Ala Ser Val Gly
1               5                   10                  15
Asp Arg Val Thr Ile Thr Cys Lys Ala Ser Gln Asp Val Ser Ile Gly
            20                  25                  30
Val Ala Trp Tyr Gln Gln Lys Pro Gly Lys Ala Pro Lys Leu Leu Ile
            35                  40                  45
Tyr Ser Ala Ser Tyr Arg Tyr Thr Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 156
<211> LENGTH: 527
<212> TYPE: PRT
<213> ORGANISM: Artificial sequence
<220> FEATURE:
<223> OTHER INFORMATION: C-terminal heavy chain fusion protein of
      Fynomer C12 (Fynomer #1; SEQ ID NO:1) with anti HER2 antibody 1,
      heavy chain (SEQ ID NO:154)

<400> SEQUENCE: 156

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
                 20                  25                  30

Thr Met Asp Trp Val Arg Gln Ala Pro Gly Lys Gly Leu Glu Trp Val
             35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
                195                 200                 205
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Gly Ser Gly Gly Gly Gly Ser Gly Gly Gly Gly Ser
    450                 455                 460

Gly Val Thr Leu Phe Val Ala Leu Tyr Asp Tyr Ser Tyr Asn Thr
465                 470                 475                 480

Arg Asp Leu Ser Phe His Lys Gly Glu Lys Phe Gln Ile Leu Arg Met
                485                 490                 495

Glu Asp Gly Val Trp Trp Glu Ala Arg Ser Leu Thr Thr Gly Glu Thr
            500                 505                 510

Gly Tyr Ile Pro Ser Asn Tyr Val Ala Pro Val Asp Ser Ile Gln
        515                 520                 525

<210> SEQ ID NO 157
<211> LENGTH: 292
<212> TYPE: PRT
<213> ORGANISM: Artificial sequence
<220> FEATURE:
<223> OTHER INFORMATION: C-terminal light chain fusion protein of
      Fynomer C12 (Fynomer #1; SEQ ID NO:1) with anti HER2 antibody 1,
      light chain (SEQ ID NO:155)

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30
```

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gly Val Thr Leu Phe Val Ala Leu Tyr Asp Tyr
225                 230                 235                 240

Thr Ser Tyr Asn Thr Arg Asp Leu Ser Phe His Lys Gly Glu Lys Phe
                245                 250                 255

Gln Ile Leu Arg Met Glu Asp Gly Val Trp Trp Glu Ala Arg Ser Leu
            260                 265                 270

Thr Thr Gly Glu Thr Gly Tyr Ile Pro Ser Asn Tyr Val Ala Pro Val
        275                 280                 285

Asp Ser Ile Gln
    290

<210> SEQ ID NO 158
<211> LENGTH: 527
<212> TYPE: PRT
<213> ORGANISM: Artificial sequence
<220> FEATURE:
<223> OTHER INFORMATION: N-terminal heavy chain fusion of Fynomer C12
    (Fynomer #1; SEQ ID NO:1) with anti HER2 antibody 1, heavy chain
    (SEQ ID NO:154)

<400> SEQUENCE: 158

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Gly Ser Gly Gly Gly Gly Ser Glu Val
65                  70                  75                  80

```
Gln Leu Val Glu Ser Gly Gly Gly Leu Val Gln Pro Gly Gly Ser Leu
                85                  90                  95

Arg Leu Ser Cys Ala Ala Ser Gly Phe Thr Phe Thr Asp Tyr Thr Met
            100                 105                 110

Asp Trp Val Arg Gln Ala Pro Gly Lys Gly Leu Glu Trp Val Ala Asp
        115                 120                 125

Val Asn Pro Asn Ser Gly Ser Ile Tyr Asn Gln Arg Phe Lys Gly
    130                 135                 140

Arg Phe Thr Leu Ser Val Asp Arg Ser Lys Asn Thr Leu Tyr Leu Gln
145                 150                 155                 160

Met Asn Ser Leu Arg Ala Glu Asp Thr Ala Val Tyr Tyr Cys Ala Arg
                165                 170                 175

Asn Leu Gly Pro Ser Phe Tyr Phe Asp Tyr Trp Gly Gln Gly Thr Leu
            180                 185                 190

Val Thr Val Ser Ser Ala Ser Thr Lys Gly Pro Ser Val Phe Pro Leu
        195                 200                 205

Ala Pro Ser Ser Lys Ser Thr Ser Gly Gly Thr Ala Ala Leu Gly Cys
    210                 215                 220

Leu Val Lys Asp Tyr Phe Pro Glu Pro Val Thr Val Ser Trp Asn Ser
225                 230                 235                 240

Gly Ala Leu Thr Ser Gly Val His Thr Phe Pro Ala Val Leu Gln Ser
                245                 250                 255

Ser Gly Leu Tyr Ser Leu Ser Ser Val Val Thr Val Pro Ser Ser Ser
            260                 265                 270

Leu Gly Thr Gln Thr Tyr Ile Cys Asn Val Asn His Lys Pro Ser Asn
        275                 280                 285

Thr Lys Val Asp Lys Lys Val Glu Pro Lys Ser Cys Asp Lys Thr His
    290                 295                 300

Thr Cys Pro Pro Cys Pro Ala Pro Glu Leu Leu Gly Gly Pro Ser Val
305                 310                 315                 320

Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
        355                 360                 365

Thr Lys Pro Arg Glu Glu Gln Tyr Asn Ser Thr Tyr Arg Val Val Ser
    370                 375                 380

Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
                405                 410                 415

Ser Lys Ala Lys Gly Gln Pro Arg Glu Pro Gln Val Tyr Thr Leu Pro
            420                 425                 430

Pro Ser Arg Glu Glu Met Thr Lys Asn Gln Val Ser Leu Thr Cys Leu
        435                 440                 445

Val Lys Gly Phe Tyr Pro Ser Asp Ile Ala Val Glu Trp Glu Ser Asn
    450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
                485                 490                 495

Trp Gln Gln Gly Asn Val Phe Ser Cys Ser Val Met His Glu Ala Leu
```

500                 505                 510
His Asn His Tyr Thr Gln Lys Ser Leu Ser Leu Ser Pro Gly Lys
        515                 520                 525

<210> SEQ ID NO 159
<211> LENGTH: 292
<212> TYPE: PRT
<213> ORGANISM: Artificial sequence
<220> FEATURE:
<223> OTHER INFORMATION: N-terminal light chain fusion protein of
      Fynomer C12 (Fynomer #1; SEQ ID NO:1) with anti HER2 antibody 1,
      light chain (SEQ ID NO:155)

<400> SEQUENCE: 159

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Gly Ser Gly Gly Gly Gly Ser Asp Ile
65                  70                  75                  80

Gln Met Thr Gln Ser Pro Ser Ser Leu Ser Ala Ser Val Gly Asp Arg
                85                  90                  95

Val Thr Ile Thr Cys Lys Ala Ser Gln Asp Val Ser Ile Gly Val Ala
            100                 105                 110

Trp Tyr Gln Gln Lys Pro Gly Lys Ala Pro Lys Leu Leu Ile Tyr Ser
        115                 120                 125

Ala Ser Tyr Arg Tyr Thr Gly Val Pro Ser Arg Phe Ser Gly Ser Gly
    130                 135                 140

Ser Gly Thr Asp Phe Thr Leu Thr Ile Ser Ser Leu Gln Pro Glu Asp
145                 150                 155                 160

Phe Ala Thr Tyr Tyr Cys Gln Gln Tyr Tyr Ile Tyr Pro Tyr Thr Phe
                165                 170                 175

Gly Gln Gly Thr Lys Val Glu Ile Lys Arg Thr Val Ala Ala Pro Ser
            180                 185                 190

Val Phe Ile Phe Pro Pro Ser Asp Glu Gln Leu Lys Ser Gly Thr Ala
        195                 200                 205

Ser Val Val Cys Leu Leu Asn Asn Phe Tyr Pro Arg Glu Ala Lys Val
    210                 215                 220

Gln Trp Lys Val Asp Asn Ala Leu Gln Ser Gly Asn Ser Gln Glu Ser
225                 230                 235                 240

Val Thr Glu Gln Asp Ser Lys Asp Ser Thr Tyr Ser Leu Ser Ser Thr
                245                 250                 255

Leu Thr Leu Ser Lys Ala Asp Tyr Glu Lys His Lys Val Tyr Ala Cys
            260                 265                 270

Glu Val Thr His Gln Gly Leu Ser Ser Pro Val Thr Lys Ser Phe Asn
        275                 280                 285

Arg Gly Glu Cys
    290

<210> SEQ ID NO 160
<211> LENGTH: 450
<212> TYPE: PRT
<213> ORGANISM: Artificial sequence
<220> FEATURE:
<223> OTHER INFORMATION: anti HER2 antibody 2, heavy chain

<400> SEQUENCE: 160

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Tyr Ser Lys Leu Thr Val Asp
              405                 410                 415

Lys Ser Arg Trp Gln Gln Gly Asn Val Phe Ser Cys Ser Val Met His
              420                 425                 430

Glu Ala Leu His Asn His Tyr Thr Gln Lys Ser Leu Ser Leu Ser Pro
              435                 440                 445

Gly Lys
    450

<210> SEQ ID NO 161
<211> LENGTH: 292
<212> TYPE: PRT
<213> ORGANISM: Artificial sequence
<220> FEATURE:
<223> OTHER INFORMATION: N-terminal light chain fusion protein of
      Fynomer C12 (Fynomer #1; SEQ ID NO:1) with anti HER2 antibody 2,
      light chain (SEQ ID NO:163)

<400> SEQUENCE: 161

Gly Val Thr Leu Phe Val Ala Leu Tyr Asp Tyr Thr Ser Tyr Asn Thr
1               5                   10                  15

Arg Asp Leu Ser Phe His Lys Gly Glu Lys Phe Gln Ile Leu Arg Met
            20                  25                  30

Glu Asp Gly Val Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Ser Gly Gly Gly Ser Gly Ser Asp Ile
65                  70                  75                  80

Gln Met Thr Gln Ser Pro Ser Ser Leu Ser Ala Ser Val Gly Asp Arg
                85                  90                  95

Val Thr Ile Thr Cys Arg Ala Ser Gln Asp Val Asn Thr Ala Val Ala
            100                 105                 110

Trp Tyr Gln Gln Lys Pro Gly Lys Ala Pro Lys Leu Leu Ile Tyr Ser
        115                 120                 125

Ala Ser Phe Leu Tyr Ser Gly Val Pro Ser Arg Phe Ser Gly Ser Arg
    130                 135                 140

Ser Gly Thr Asp Phe Thr Leu Thr Ile Ser Ser Leu Gln Pro Glu Asp
145                 150                 155                 160

Phe Ala Thr Tyr Tyr Cys Gln Gln His Tyr Thr Thr Pro Pro Thr Phe
                165                 170                 175

Gly Gln Gly Thr Lys Val Glu Ile Lys Arg Thr Val Ala Ala Pro Ser
            180                 185                 190

Val Phe Ile Phe Pro Pro Ser Asp Glu Gln Leu Lys Ser Gly Thr Ala
        195                 200                 205

Ser Val Val Cys Leu Leu Asn Asn Phe Tyr Pro Arg Glu Ala Lys Val
    210                 215                 220

Gln Trp Lys Val Asp Asn Ala Leu Gln Ser Gly Asn Ser Gln Glu Ser
225                 230                 235                 240

Val Thr Glu Gln Asp Ser Lys Asp Ser Thr Tyr Ser Leu Ser Ser Thr
                245                 250                 255

Leu Thr Leu Ser Lys Ala Asp Tyr Glu Lys His Lys Val Tyr Ala Cys
            260                 265                 270

Glu Val Thr His Gln Gly Leu Ser Ser Pro Val Thr Lys Ser Phe Asn
        275                 280                 285

```
Arg Gly Glu Cys
    290

<210> SEQ ID NO 162
<211> LENGTH: 17
<212> TYPE: PRT
<213> ORGANISM: Artificial sequence
<220> FEATURE:
<223> OTHER INFORMATION: myc-hexahistidine tag (SEQ ID NO: 162)

<400> SEQUENCE: 162

Gly Glu Gln Lys Leu Ile Ser Glu Glu Asp Leu His His His His His
1               5                   10                  15

His

<210> SEQ ID NO 163
<211> LENGTH: 214
<212> TYPE: PRT
<213> ORGANISM: Artificial sequence
<220> FEATURE:
<223> OTHER INFORMATION: anti HER2 antibody 2, light chain

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 164
<211> LENGTH: 63
<212> TYPE: PRT
<213> ORGANISM: Artificial sequence
<220> FEATURE:
<223> OTHER INFORMATION: wild-type SH3 domain of the Fyn kinase (Fyn
      SH3)
```

-continued

<400> SEQUENCE: 164

Gly Val Thr Leu Phe Val Ala Leu Tyr Asp Tyr Glu Ala Arg Thr Glu
1               5                   10                  15

Asp Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 165
<211> LENGTH: 1362
<212> TYPE: DNA
<213> ORGANISM: Artificial sequence
<220> FEATURE:
<223> OTHER INFORMATION: Anti-HER2 antibody 1 (heavy chain) (coding for
      amino acids shown in SEQ ID NO: 154)

<400> SEQUENCE: 165

```
gaggtgcagc tggtcgaatc tggtgggggc ctggtgcagc ctgggggctc cctgagactg      60
tcctgtgccg catccggttt tacatttacc gactacacaa tggattgggt gcgacaggca     120
cccgggaagg gtctggagtg ggtggctgac gtgaacccta ttccggcgg aagcatctac      180 aaccagaggt tcaagggccg gtttactctg tctgtggaca ggagtaaaaa cacctgtat     240 ctgcagatga attccctgag agccgaagat acagctgtct actattgcgc tcgcaatctg     300
ggtccatcat tctactttga ctattggggg cagggaactc tggtgactgt ctcatccgct     360
agcacaaagg gccctagtgt gtttcctctg gctccctctt ccaaatccac ttctggtggc     420
actgctgctc tgggatgcct ggtgaaggat tactttcctg aacctgtgac tgtctcatgg     480
aactctggtg ctctgacttc tggtgtccac actttccctg ctgtgctgca gtctagtgga     540
ctgtactctc tgtcatctgt ggtcactgtg ccctcttcat ctctgggaac ccagacctac     600
atttgtaatg tgaaccacaa accatccaac actaaagtgg acaaaaaagt ggaacccaaa     660
tcctgtgaca aaacccacac ctgcccacct tgtcctgccc ctgaactgct gggaggacct     720
tctgtgtttc tgttccccc caaaccaaag ataccctga tgatctctag aacccctgag      780
gtgacatgtg tggtggtgga tgtgtctcat gaggaccctg aggtcaaatt caactggtac     840
gtggatggag tggaagtcca caatgccaaa accaagccta gagaggaaca gtacaattca     900
acctacagag tggtcagtgt gctgactgtg ctgcatcagg attggctgaa tggcaaggaa     960
tacaagtgta aagtctcaaa caaggccctg cctgctccaa ttgagaaaac aatctcaaag    1020
gccaagggac agcctaggga acccagtc tacaccctgc caccttcaag agaggaaatg     1080
accaaaaacc aggtgtccct gacatgcctg gtcaaaggct ctacccttc tgacattgct     1140 gtggagtggg agtcaaatgg acagcctgag aacaactaca aacaacccc ccctgtgctg     1200 gattctgatg gctctttctt tctgtactcc aaactgactg tggacaagtc tagatgcag     1260 cagggggaatg tcttttcttg ctctgtcatg catgaggctc tgcataacca ctacactcag    1320
aaatccctgt ctctgtctcc tggcaaatga tagtaaaagc tt                       1362
```

<210> SEQ ID NO 166
<211> LENGTH: 657
<212> TYPE: DNA
<213> ORGANISM: Artificial sequence
<220> FEATURE:
<223> OTHER INFORMATION: Anti-HER2 antibody 1 (light chain) (coding for
      amino acids shown in SEQ ID NO:155)

<400> SEQUENCE: 166

```
gatatccaga tgacccagag ccctagtagt ctgagcgcaa gcgtcgggga ccgtgtgacc      60
attacctgta aagcaagcca ggatgtgtct atcggtgtgg catggtatca gcagaagccc     120
ggcaaagccc ctaagctgct gatctactct gctagttaca gatatactgg agtcccaagt    180
cggttctcag gctccggaag cgggaccgac tttacccctga caatctcctc cctgcaaccc    240
gaggatttcg ccacatacta ttgccagcag tactacatct atccttatac attcgggcag    300
gggacaaaag tggaaatcaa acggactgtg gcggcgcctt ctgtgttcat tttcccccca   360
tctgatgaac agctgaaatc tggcactgct tctgtggtct gtctgctgaa caacttctac    420
cctagagagg ccaaagtcca gtggaaagtg gacaatgctc tgcagagtgg gaattcccag    480
gaatctgtca ctgagcagga ctctaaggat agcacatact ccctgtcctc tactctgaca    540
ctgagcaagg ctgattacga gaaacacaaa gtgtacgcct gtgaagtcac acatcagggg    600
ctgtctagtc ctgtgaccaa atccttcaat aggggagagt gctgatagta aaagctt       657
```

<210> SEQ ID NO 167
<211> LENGTH: 891
<212> TYPE: DNA
<213> ORGANISM: Artificial sequence
<220> FEATURE:
<223> OTHER INFORMATION: N-terminal fusion of C12 to light chain of anti-HER2 antibody 1 (coding for amino acids shown in SEQ ID NO: 159)

<400> SEQUENCE: 167

```
ggggtgactc tgttcgtcgc tctgtatgat tacacttcct ataacaccag agacctgagc     60
ttccacaagg gcgagaaatt tcagatcctg aggatggagg atggagtgtg gtgggaagcc    120
cggtctctga ccacagggga gacaggttac attccttcaa actacgtcgc tcccgtggac    180
agcattcagg gtggtggggg atccggcgga ggaggaagtg gcggaggagg aagtgatatc    240
cagatgaccc agagccctag tagtctgagc gcaagcgtcg ggaccgtgt gaccattacc    300
tgtaaagcaa gccaggatgt gtctatcggt gtggcatggt atcagcagaa gcccggcaaa    360
gcccctaagc tgctgatcta ctctgctagt tacagatata ctggagtccc aagtcggttc    420
tcaggctccg gaagcgggac cgactttacc ctgacaatct cctccctgca acccgaggat    480
ttcgccacat actattgcca gcagtactac atctatcctt atacattcgg gcaggggaca    540
aaagtggaaa tcaaacggac tgtggcggcg ccttctgtgt tcatttttccc cccatctgat    600
gaacagctga atctggcac tgcttctgtg gtctgtctgc tgaacaactt ctaccctaga    660
gaggccaaag tccagtggaa agtggacaat gctctgcaga gtgggaattc ccaggaatct    720
gtcactgagc aggactctaa ggatagcaca tactccctgt cctctactct gacactgagc    780
aaggctgatt acgagaaaca caaagtgtac gcctgtgaag tcacacatca ggggctgtct    840
agtcctgtga ccaaatcctt caataggga gagtgctgat agtaaaagct t               891
```

<210> SEQ ID NO 168
<211> LENGTH: 1365
<212> TYPE: DNA
<213> ORGANISM: Artificial sequence
<220> FEATURE:
<223> OTHER INFORMATION: Anti-HER2 antibody 2 (heavy chain) (coding for amino acids shown in SEQ ID NO: 160)

<400> SEQUENCE: 168

```
gaagtccagc tggtcgaatc tggtggtggc ctggtccagc ctggtggatc actgagactg      60
```

```
tcctgtgctg cttctggttt caacatcaag acacctaca tccattgggt cagacaggca      120
cctggcaagg gactggaatg ggtcgcccga atctaccctc aaacggcta cactcgctac      180 gccgactccg tcaagggacg ctttaccatc tccgccgaca cctctaaaaa caccgcctac      240
ctgcagatga atagtctgag ggccgaggat actgctgtgt actactgctc acgatgggga      300
ggcgacggct tttacgctat ggattactgg ggacagggaa ctctggtcac tgtgtctagc      360
gctagcacaa agggccctag tgtgtttcct ctggctccct cttccaaatc cacttctggt      420
ggcactgctg ctctgggatg cctggtgaag gattactttc ctgaacctgt gactgtctca      480
tggaactctg gtgctctgac ttctggtgtc cacactttcc ctgctgtgct gcagtctagt      540
ggactgtact ctctgtcatc tgtggtcact gtgccctctt catctctggg aacccagacc      600
tacatttgta atgtgaacca caaaccatcc aacactaaag tggacaaaaa agtgaaccc       660 aaatcctgtg acaaaaccca cacctgccca ccttgtcctg ccctgaact gctgggagga       720 ccttctgtgt tctgttccc ccccaaacca aaggataccc tgatgatctc tagaacccct       780
gaggtgacat gtgtggtggt ggatgtgtct catgaggacc ctgaggtcaa attcaactgg      840
tacgtggatg gagtggaagt ccacaatgcc aaaaccaagc ctagagagga acagtacaat      900
tcaacctaca gagtggtcag tgtgctgact gtgctgcatc aggattggct gaatggcaag      960
gaatacaagt gtaaagtctc aaacaaggcc ctgcctgctc aattgagaa acaatctca      1020 aaggccaagg gacagcctag ggaaccccag gtctacaccc tgccaccttc aagagaggaa    1080
atgaccaaaa accaggtgtc cctgacatgc ctggtcaaag gcttctaccc ttctgacatt    1140
gctgtggagt gggagtcaaa tggacagcct gagaacaact acaaaacaac cccccctgtg    1200
ctggattctg atggctcttt ctttctgtac tccaaactga ctgtggacaa gtctagatgg    1260
cagcagggga atgtcttttc ttgctctgtc atgcatgagg ctctgcataa ccactacact    1320
cagaaatccc tgtctctgtc tcctggcaaa tgatagtaaa agctt                   1365
```

<210> SEQ ID NO 169  
<211> LENGTH: 657  
<212> TYPE: DNA  
<213> ORGANISM: Artificial sequence  
<220> FEATURE:  
<223> OTHER INFORMATION: Anti-HER2 antibody 2 (light chain) (coding for amino acids shown in SEQ ID NO: 163)

<400> SEQUENCE: 169

```
gacatccaga tgacacagtc tccctcttcc ctgtccgctt ctgtgggcga tcgagtgaca       60
atcacctgta gggctagtca ggatgtgaat actgctgttg cttggtacca gcagaaacca      120
ggaaaagccc ctaaactgct gatctactct gcctcattcc tgtactctgg ggtgccttct      180
cgattcagtg gttctagatc tggcaccgat ttcacactga ccatttcttc actgcaacct      240
gaggattttg ccacctacta ctgtcagcag cactacacaa cacctcccac atttggccag      300
ggcacaaaag tggagatcaa acggaccgtg gcggcgcctt ctgtgttcat tttcccccca      360
tctgatgaac agctgaaatc tggcactgct tctgtggtct gtctgctgaa caacttctac      420
cctagagagg ccaaagtcca gtggaaagtg gacaatgctc tgcagagtgg aattcccag      480 gaatctgtca ctgagcagga ctctaaggat agcacatact ccctgtcctc tactctgaca      540
ctgagcaagg ctgattacga gaaacacaaa gtgtacgcct gtgaagtcac acatcagggg     600
ctgtctagtc ctgtgaccaa atccttcaat aggggagagt gctgatagta aaagctt        657
```

-continued

```
<210> SEQ ID NO 170
<211> LENGTH: 891
<212> TYPE: DNA
<213> ORGANISM: Artificial sequence
<220> FEATURE:
<223> OTHER INFORMATION: N-terminal C12 fusion to anti-HER2 antibody 2
      light chain (coding for amino acids shown in SEQ ID NO: 161)

<400> SEQUENCE: 170
ggggtgactc tgttcgtcgc tctgtatgat tacacttcct ataacaccag agacctgagc      60
ttccacaagg gcgagaaatt tcagatcctg aggatggagg atggagtgtg gtgggaagcc    120
cggtctctga ccacagggga gacaggttac attccttcaa actacgtcgc tcccgtggac    180
agcattcagg gtggtggggg atccggcgga ggaggaagtg gcgaggagg aagtgacatc      240 cagatgacac agtctccctc ttccctgtcc gcttctgtgg gcgatcgagt gacaatcacc    300
tgtagggcta gtcaggatgt gaatactgct gttgcttggt accagcagaa accaggaaaa    360
gcccctaaac tgctgatcta ctctgcctca ttcctgtact ctggggtgcc ttctcgattc    420
agtggttcta gatctggcac cgatttcaca ctgaccattt cttcactgca acctgaggat    480
tttgccacct actactgtca gcagcactac acaacacctc ccacatttgg ccagggcaca    540
aaagtggaga tcaaacggac cgtggcgcg ccttctgtgt tcattttccc cccatctgat      600
gaacagctga atctggcac tgcttctgtg gtctgtctgc tgaacaactt ctaccctaga    660
gaggccaaag tccagtggaa agtggacaat gctctgcaga gtgggaattc ccaggaatct    720
gtcactgagc aggactctaa ggatagcaca tactccctgt cctctactct gacactgagc    780
aaggctgatt acgagaaaca caaagtgtac gcctgtgaag tcacacatca ggggctgtct    840
agtcctgtga ccaaatcctt caatagggga gagtgctgat agtaaaagct t             891

<210> SEQ ID NO 171
<211> LENGTH: 1255
<212> TYPE: PRT
<213> ORGANISM: Homo sapiens

<400> SEQUENCE: 171

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
```

```
                165                 170                 175
Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590
```

```
Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
    690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
    770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
    850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu  Asp Ser Thr Phe Tyr Arg Ser Leu
        995                 1000                1005
```

-continued

```
Leu Glu Asp Asp Asp Met Gly Asp Leu Val Asp Ala Glu Glu Tyr
1010                1015                1020

Leu Val Pro Gln Gln Gly Phe Phe Cys Pro Asp Pro Ala Pro Gly
1025                1030                1035

Ala Gly Gly Met Val His His Arg His Arg Ser Ser Ser Thr Arg
1040                1045                1050

Ser Gly Gly Gly Asp Leu Thr Leu Gly Leu Glu Pro Ser Glu Glu
1055                1060                1065

Glu Ala Pro Arg Ser Pro Leu Ala Pro Ser Glu Gly Ala Gly Ser
1070                1075                1080

Asp Val Phe Asp Gly Asp Leu Gly Met Gly Ala Ala Lys Gly Leu
1085                1090                1095

Gln Ser Leu Pro Thr His Asp Pro Ser Pro Leu Gln Arg Tyr Ser
1100                1105                1110

Glu Asp Pro Thr Val Pro Leu Pro Ser Glu Thr Asp Gly Tyr Val
1115                1120                1125

Ala Pro Leu Thr Cys Ser Pro Gln Pro Glu Tyr Val Asn Gln Pro
1130                1135                1140

Asp Val Arg Pro Gln Pro Pro Ser Pro Arg Glu Gly Pro Leu Pro
1145                1150                1155

Ala Ala Arg Pro Ala Gly Ala Thr Leu Glu Arg Pro Lys Thr Leu
1160                1165                1170

Ser Pro Gly Lys Asn Gly Val Val Lys Asp Val Phe Ala Phe Gly
1175                1180                1185

Gly Ala Val Glu Asn Pro Glu Tyr Leu Thr Pro Gln Gly Gly Ala
1190                1195                1200

Ala Pro Gln Pro His Pro Pro Pro Ala Phe Ser Pro Ala Phe Asp
1205                1210                1215

Asn Leu Tyr Tyr Trp Asp Gln Asp Pro Pro Glu Arg Gly Ala Pro
1220                1225                1230

Pro Ser Thr Phe Lys Gly Thr Pro Thr Ala Glu Asn Pro Glu Tyr
1235                1240                1245

Leu Gly Leu Asp Val Pro Val
1250                1255

<210> SEQ ID NO 172
<211> LENGTH: 217
<212> TYPE: PRT
<213> ORGANISM: Homo sapiens

<400> SEQUENCE: 172

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110
```

```
Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
            165                 170                 175

Asn Gln Leu Ala Leu Thr Leu Ile Asp Thr Asn Arg Ser Arg Ala Cys
        180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg
    210                 215

<210> SEQ ID NO 173
<211> LENGTH: 10
<212> TYPE: PRT
<213> ORGANISM: Artificial Sequence
<220> FEATURE:
<223> OTHER INFORMATION: RT-loop

<400> SEQUENCE: 173

Asp Tyr Glu Ala Arg Thr Glu Asp Asp Leu
1               5                   10

<210> SEQ ID NO 174
<211> LENGTH: 6
<212> TYPE: PRT
<213> ORGANISM: Artificial Sequence
<220> FEATURE:
<223> OTHER INFORMATION: Scr loop

<400> SEQUENCE: 174

Leu Asn Ser Ser Glu Gly
1               5

<210> SEQ ID NO 175
<211> LENGTH: 68
<212> TYPE: PRT
<213> ORGANISM: Artificial Sequence
<220> FEATURE:
<223> OTHER INFORMATION: Formula I
<220> FEATURE:
<221> NAME/KEY: VARIANT
<222> LOCATION: (12)..(18)
<223> OTHER INFORMATION: Xaa is G, V, T, L, F, A, Y, D, S, H, K, E, Q,
      I, Q, R, M, P, or N
<220> FEATURE:
<221> NAME/KEY: VARIANT
<222> LOCATION: (12)..(12)
<223> OTHER INFORMATION: Xaa is T, E, D, Q, Y, V, W, N, S, or K
<220> FEATURE:
<221> NAME/KEY: VARIANT
<222> LOCATION: (13)..(13)
<223> OTHER INFORMATION: Xaa is S, A, R, or T
<220> FEATURE:
<221> NAME/KEY: VARIANT
<222> LOCATION: (14)..(14)
<223> OTHER INFORMATION: Xaa is Y, R, H, T, N, V, W, or S
<220> FEATURE:
<221> NAME/KEY: VARIANT
<222> LOCATION: (15)..(15)
<223> OTHER INFORMATION: Xaa is N, D, M, Y, R, P, E, L, H, T, G, or F
<220> FEATURE:
<221> NAME/KEY: VARIANT
<222> LOCATION: (16)..(16)
```

-continued

```
<223> OTHER INFORMATION: Xaa is T, S, P, Q, R, K, G, Q, A, D, M, N, L,
      F, Y, or E
<220> FEATURE:
<221> NAME/KEY: VARIANT
<222> LOCATION: (17)..(17)
<223> OTHER INFORMATION: Xaa is R, M, K, D, F, T, G, H, S, P, N, Q, Y,
      L, A, or P
<220> FEATURE:
<221> NAME/KEY: VARIANT
<222> LOCATION: (18)..(18)
<223> OTHER INFORMATION: Xaa is D, G, V, L, H, N, R, F, S, or A
<220> FEATURE:
<221> NAME/KEY: VARIANT
<222> LOCATION: (19)..(21)
<223> OTHER INFORMATION: Xaa is G, V, T, L, F, A, Y, D, S, H, K, E, Q,
      I, Q, R, P, N, or C
<220> FEATURE:
<221> NAME/KEY: VARIANT
<222> LOCATION: (19)..(19)
<223> OTHER INFORMATION: Xaa is G, S, E, D, P, Y, or is absent
<220> FEATURE:
<221> NAME/KEY: VARIANT
<222> LOCATION: (20)..(20)
<223> OTHER INFORMATION: Xaa is Q, D, S, H, or is absent
<220> FEATURE:
<221> NAME/KEY: VARIANT
<222> LOCATION: (21)..(21)
<223> OTHER INFORMATION: Xaa is D, V, or is absent
<220> FEATURE:
<221> NAME/KEY: VARIANT
<222> LOCATION: (34)..(36)
<223> OTHER INFORMATION: Xaa is G, V, T, L, F, A, Y, D, S, H, K, E, Q,
      I, Q, R, M, P, or N
<220> FEATURE:
<221> NAME/KEY: VARIANT
<222> LOCATION: (34)..(34)
<223> OTHER INFORMATION: Xaa is R, K, Q, N, S, G, W, M, H, L, F, E, T,
      P, A, D, or V
<220> FEATURE:
<221> NAME/KEY: VARIANT
<222> LOCATION: (35)..(35)
<223> OTHER INFORMATION: Xaa is M, R, E, G, N, D, S, A, Q, F, P, K, Y,
      T, H, V, L, or W
<220> FEATURE:
<221> NAME/KEY: VARIANT
<222> LOCATION: (36)..(36)
<223> OTHER INFORMATION: Xaa is E, W, P, R, K, S, V, N, D, H, G, T, Q,
      A, Y, L, or M
<220> FEATURE:
<221> NAME/KEY: VARIANT
<222> LOCATION: (37)..(39)
<223> OTHER INFORMATION: Xaa is G, V, T, L, F, A, Y, D, S, H, K, E, Q,
      I, Q, R, P, N, or C
<220> FEATURE:
<221> NAME/KEY: VARIANT
<222> LOCATION: (37)..(37)
<223> OTHER INFORMATION: Xaa is D, R, Q, S, A, N, P, I, H, T, Y, E, L,
      K, M, V, I, W, or is absent
<220> FEATURE:
<221> NAME/KEY: VARIANT
<222> LOCATION: (38)..(38)
<223> OTHER INFORMATION: Xaa is G, S, I, L, A, V, T, E, D, Q, R, P, K,
      M, H, Y, or is absent
<220> FEATURE:
<221> NAME/KEY: VARIANT
<222> LOCATION: (39)..(39)
<223> OTHER INFORMATION: Xaa is K, G, R, A, T, V, S, I, E, Q, P, D, N,
      H, or is absent
<220> FEATURE:
<221> NAME/KEY: VARIANT
<222> LOCATION: (41)..(41)
<223> OTHER INFORMATION: Xaa is G, V, T, L, F, A, Y, D, S, H, K, E, Q,
      I, Q, R, M, P, or N
<220> FEATURE:
<221> NAME/KEY: VARIANT
<222> LOCATION: (41)..(41)
<223> OTHER INFORMATION: Xaa is V, D, T, I, or Y
<220> FEATURE:
<221> NAME/KEY: VARIANT
```

```
<222> LOCATION: (44)..(44)
<223> OTHER INFORMATION: Xaa is G, V, T, L, F, A, Y, D, S, H, K, E, Q,
      I, Q, R, M, P, or N
<220> FEATURE:
<221> NAME/KEY: VARIANT
<222> LOCATION: (44)..(44)
<223> OTHER INFORMATION: Xaa is E, A, R, T, or Q
<220> FEATURE:
<221> NAME/KEY: VARIANT
<222> LOCATION: (53)..(53)
<223> OTHER INFORMATION: Xaa is G, V, T, L, F, A, Y, D, S, H, K, E, Q,
      I, Q, R, M, P, or N
<220> FEATURE:
<221> NAME/KEY: VARIANT
<222> LOCATION: (53)..(53)
<223> OTHER INFORMATION: Xaa is T, I, or V
<220> FEATURE:
<221> NAME/KEY: VARIANT
<222> LOCATION: (55)..(55)
<223> OTHER INFORMATION: Xaa is G, V, T, L, F, A, Y, D, S, H, K, E, Q,
      I, Q, R, M, P, or N
<220> FEATURE:
<221> NAME/KEY: VARIANT
<222> LOCATION: (55)..(55)
<223> OTHER INFORMATION: Xaa is Y, L, or F
<220> FEATURE:
<221> NAME/KEY: VARIANT
<222> LOCATION: (58)..(58)
<223> OTHER INFORMATION: Xaa is G, V, T, L, F, A, Y, D, S, H, K, E, Q,
      I, Q, R, M, P, or N
<220> FEATURE:
<221> NAME/KEY: VARIANT
<222> LOCATION: (59)..(59)
<223> OTHER INFORMATION: Xaa is N or S

<400> SEQUENCE: 175

Gly Val Thr Leu Phe Val Ala Leu Tyr Asp Tyr Xaa Xaa Xaa Xaa Xaa
1               5                   10                  15

Xaa Xaa Xaa Xaa Xaa Leu Ser Phe His Lys Gly Glu Lys Phe Gln Ile
                20                  25                  30

Leu Xaa Xaa Xaa Xaa Xaa Xaa Gly Xaa Trp Trp Xaa Ala Arg Ser Leu
            35                  40                  45

Thr Thr Gly Glu Xaa Gly Xaa Ile Pro Ser Xaa Tyr Val Ala Pro Val
    50                  55                  60

Asp Ser Ile Gln
65

<210> SEQ ID NO 176
<211> LENGTH: 7
<212> TYPE: PRT
<213> ORGANISM: Artificial Sequence
<220> FEATURE:
<223> OTHER INFORMATION: Resides 12 to 21 of Formula I

<400> SEQUENCE: 176

Thr Ser Tyr Asn Thr Arg Asp
1               5

<210> SEQ ID NO 177
<211> LENGTH: 4
<212> TYPE: PRT
<213> ORGANISM: Artificial Sequence
<220> FEATURE:
<223> OTHER INFORMATION: Residues 34 to 39 of Formula I

<400> SEQUENCE: 177

Arg Met Glu Asp
1
```